(12) United States Patent
Gupta et al.

(10) Patent No.: US 11,813,052 B2
(45) Date of Patent: Nov. 14, 2023

(54) SYSTEMS AND METHODS FOR INTRA-OPERATIVE PELVIC REGISTRATION

(71) Applicant: MAKO Surgical Corp., Weston, FL (US)

(72) Inventors: Sunil Gupta, Fort Lauderdale, FL (US); Ta-Cheng Chang, Weston, FL (US); Zenan Zhang, Fort Lauderdale, FL (US); Kevin Bechtold, Fort Lauderdale, FL (US); Matthew Thompson, Fort Lauderdale, FL (US); Eric Branch, Weston, FL (US); Varun Chandra, Fort Lauderdale, FL (US); Zhu Wu, Fort Lauderdale, FL (US)

(73) Assignee: MAKO SURGICAL CORP., Weston, FL (US)

( * ) Notice: Subject to any disclaimer, the term of this patent is extended or adjusted under 35 U.S.C. 154(b) by 116 days.

(21) Appl. No.: 17/573,264

(22) Filed: Jan. 11, 2022

(65) Prior Publication Data
US 2022/0125334 A1 Apr. 28, 2022

Related U.S. Application Data

(63) Continuation of application No. 16/653,207, filed on Oct. 15, 2019, now Pat. No. 11,246,508, which is a
(Continued)

(51) Int. Cl.
*A61B 5/107* (2006.01)
*A61B 5/06* (2006.01)
(Continued)

(52) U.S. Cl.
CPC .............. *A61B 5/107* (2013.01); *A61B 5/055* (2013.01); *A61B 5/06* (2013.01); *A61B 5/1071* (2013.01);
(Continued)

(58) Field of Classification Search
CPC .............. A61B 19/50; A61B 2019/501; A61B 2019/502; A61B 2019/504;
(Continued)

(56) References Cited

U.S. PATENT DOCUMENTS

| 4,841,975 A | * | 6/1989 | Woolson | ............... | A61B 17/154 |
| | | | | | 600/587 |
| 4,936,862 A | * | 6/1990 | Walker | ............... | G05B 19/4207 |
| | | | | | 700/98 |

(Continued)

FOREIGN PATENT DOCUMENTS

| CA | 3034071 A1 | 3/2018 |
| DE | 10311454 A1 | 10/2004 |

(Continued)

OTHER PUBLICATIONS

Australian Patent Examination Report No. 1, AU 2017319515, dated Mar. 13, 2019.

(Continued)

*Primary Examiner* — Eric S Gibson
(74) *Attorney, Agent, or Firm* — Polsinelli PC

(57) ABSTRACT

A system for intra-operatively registering a pelvis comprising an acetabulum with a computer model of the pelvis in a coordinate system. The system may include: a) a surgical navigation system including a tracking device; and b) at least one computing device in communication with the surgical navigation system. The at least one computing device: i) receiving first data points from first intra-operatively collected points on an articular surface of the acetabulum, the first data points collected with the tracking device; ii) receiving a second data point from a second intra-operatively collected point on the pelvis, the second data point collected with the tracking device, the second data point corresponding in location to a second virtual data point on the computer model; and iii) determining an intra- (Continued)

operative center of rotation of the femur relative to the pelvis from the first data points.

17 Claims, 26 Drawing Sheets

Related U.S. Application Data continuation of application No. 16/329,157, filed as application No. PCT/US2017/049466 on Aug. 30, 2017, now Pat. No. 10,485,450.

(60) Provisional application No. 62/381,214, filed on Aug. 30, 2016.

(51) Int. Cl.
*A61B 5/00* (2006.01)
*G06T 7/73* (2017.01)
*G06T 7/33* (2017.01)
*A61B 5/11* (2006.01)
*A61B 5/055* (2006.01)
*A61B 34/30* (2016.01)
*A61B 34/20* (2016.01)
*A61B 90/00* (2016.01)

(52) U.S. Cl.
CPC ............ *A61B 5/1127* (2013.01); *A61B 5/743* (2013.01); *A61B 5/7435* (2013.01); *A61B 34/20* (2016.02); *A61B 34/30* (2016.02); *G06T 7/33* (2017.01); *G06T 7/73* (2017.01); *A61B 2034/2055* (2016.02); *A61B 2034/2068* (2016.02); *A61B 2090/364* (2016.02); *G06T 2207/10024* (2013.01); *G06T 2207/10081* (2013.01); *G06T 2207/30008* (2013.01); *G06T 2207/30052* (2013.01)

(58) Field of Classification Search
CPC . A61B 2019/507; A61B 5/107; A61B 5/4528; A61B 5/4571; A61B 5/4851
See application file for complete search history.

(56) References Cited

U.S. PATENT DOCUMENTS

| | | | |
|---|---|---|---|
| 5,534,005 A | 7/1996 | Tokish, Jr. et al. | |
| 5,871,018 A * | 2/1999 | Delp .................. | A61B 17/154 128/898 |
| 5,920,395 A * | 7/1999 | Schulz ................ | A61B 34/20 600/407 |
| 5,987,349 A * | 11/1999 | Schulz ................ | A61B 5/0073 356/614 |
| 5,995,738 A * | 11/1999 | DiGioia, III ......... | A61F 2/4657 703/11 |
| 6,245,109 B1 * | 6/2001 | Mendes .................. | A61F 2/468 623/18.11 |
| 6,442,416 B1 * | 8/2002 | Schultz ................ | A61B 8/5238 606/130 |
| 6,447,448 B1 * | 9/2002 | Ishikawa .............. | A61B 5/036 600/377 |
| 6,662,036 B2 * | 12/2003 | Cosman ................ | A61B 6/5247 600/417 |
| 6,711,431 B2 * | 3/2004 | Sarin ..................... | A61F 2/4657 606/130 |
| 6,711,432 B1 * | 3/2004 | Krause ................ | A61B 90/36 600/426 |
| 7,033,360 B2 * | 4/2006 | Cinquin ................ | A61F 2/4657 606/88 |
| 7,060,102 B2 * | 6/2006 | Thompson ........... | A61F 2/3609 623/23.35 |
| 7,383,164 B2 * | 6/2008 | Aram ..................... | A61F 2/38 606/1 |
| 7,606,613 B2 * | 10/2009 | Simon .................... | G16H 40/63 600/414 |
| 7,611,541 B2 * | 11/2009 | Thompson ............ | A61F 2/3609 623/23.35 |
| 7,618,419 B2 * | 11/2009 | Lavallee ................ | A61B 90/36 606/86 R |
| 7,769,429 B2 * | 8/2010 | Hu ........................ | A61F 2/468 600/437 |
| 7,780,681 B2 * | 8/2010 | Sarin ..................... | A61B 34/20 606/130 |
| 7,835,778 B2 | 11/2010 | Foley et al. | |
| 7,885,705 B2 * | 2/2011 | Murphy ................ | A61B 90/06 606/85 |
| 7,955,280 B2 * | 6/2011 | Radinsky .............. | A61B 5/103 600/595 |
| 8,010,180 B2 * | 8/2011 | Quaid ................... | A61B 34/71 600/426 |
| 8,014,984 B2 * | 9/2011 | Iannotti ................ | G16H 50/50 623/19.13 |
| 8,034,057 B2 * | 10/2011 | Penenberg ............ | A61F 2/4657 606/91 |
| 8,078,254 B2 * | 12/2011 | Murphy ................ | A61F 2/4657 600/407 |
| 8,152,816 B2 * | 4/2012 | Tuma .................... | A61B 90/36 382/131 |
| 8,257,360 B2 * | 9/2012 | Richard ................ | A61B 90/06 606/88 |
| 8,439,926 B2 * | 5/2013 | Bojarski ............ | A61B 17/1659 606/88 |
| 8,444,651 B2 * | 5/2013 | Kunz .................. | A61B 17/1757 606/87 |
| 8,449,551 B2 * | 5/2013 | Amiot ................... | A61F 2/4657 606/86 R |
| 8,480,754 B2 * | 7/2013 | Bojarski ............... | A61F 2/5046 623/20.14 |
| 8,529,630 B2 * | 9/2013 | Bojarski ............... | A61B 17/17 623/20.14 |
| 8,565,853 B2 * | 10/2013 | Frigg ..................... | A61B 34/20 600/407 |
| 8,571,628 B2 * | 10/2013 | Kang .................... | A61B 34/71 600/407 |
| 8,603,180 B2 * | 12/2013 | White ................. | A61B 17/1642 623/22.11 |
| 8,617,171 B2 * | 12/2013 | Park ..................... | A61B 17/1675 606/88 |
| 8,626,267 B2 * | 1/2014 | Lavallee ................ | A61B 90/39 600/424 |
| 8,635,082 B2 * | 1/2014 | Woods .................. | G16H 50/20 705/2 |
| 8,693,634 B2 * | 4/2014 | Ramamurthi ........ | A61B 6/5247 378/62 |
| 8,702,712 B2 * | 4/2014 | Jordan .................. | A61B 17/15 606/88 |
| 8,721,721 B2 * | 5/2014 | Linder-Ganz ......... | A61F 2/4684 606/88 |
| 8,737,700 B2 * | 5/2014 | Park ...................... | A61B 5/055 382/128 |
| 9,167,989 B2 * | 10/2015 | Odermatt ............... | G16H 50/50 |
| 10,485,450 B2 * | 11/2019 | Gupta .................... | A61B 5/055 |
| 10,959,857 B2 | 3/2021 | Wu et al. | |
| 11,246,508 B2 * | 2/2022 | Gupta ...................... | G06T 7/33 |
| 2003/0004518 A1 * | 1/2003 | Perren ................ | A61B 17/6483 606/102 |
| 2003/0225415 A1 * | 12/2003 | Richard ................ | A61B 90/36 600/587 |
| 2004/0092944 A1 * | 5/2004 | Penenberg ............ | A61B 34/20 606/91 |
| 2004/0167654 A1 | 8/2004 | Grimm et al. | |
| 2004/0171924 A1 * | 9/2004 | Mire ...................... | A61B 34/20 600/407 |
| 2004/0181149 A1 * | 9/2004 | Langlotz ............... | A61B 34/20 600/431 |
| 2004/0243148 A1 * | 12/2004 | Wasielewski ......... | A61B 5/062 977/932 |
| 2005/0149050 A1 * | 7/2005 | Stifter ................... | A61B 90/36 600/587 |

(56) References Cited

U.S. PATENT DOCUMENTS

| | | | |
|---|---|---|---|
| 2005/0281465 A1* | 12/2005 | Marquart | A61B 34/20 382/195 |
| 2006/0122541 A1* | 6/2006 | Tuma | A61B 5/4528 600/587 |
| 2006/0264731 A1* | 11/2006 | Murphy | A61F 2/4657 600/407 |
| 2006/0287613 A1* | 12/2006 | Amiot | A61F 2/4657 600/587 |
| 2006/0293614 A1* | 12/2006 | Radinsky | A61B 5/4528 600/587 |
| 2007/0005145 A1* | 1/2007 | Banks | A61B 5/6846 600/595 |
| 2007/0066917 A1* | 3/2007 | Hodorek | A61B 90/36 600/595 |
| 2007/0173815 A1* | 7/2007 | Murase | A61B 17/15 606/53 |
| 2007/0085085 A1 | 8/2007 | Couture et al. | |
| 2007/0209220 A1* | 9/2007 | Murphy | A61B 5/103 33/512 |
| 2007/0219561 A1 | 9/2007 | Lavallee et al. | |
| 2007/0249967 A1* | 10/2007 | Buly | A61B 5/1121 600/595 |
| 2008/0010706 A1 | 1/2008 | Moses et al. | |
| 2008/0039717 A1* | 2/2008 | Frigg | A61C 19/04 600/424 |
| 2008/0146969 A1* | 6/2008 | Kurtz | A61B 17/56 600/595 |
| 2008/0234833 A1* | 9/2008 | Bandoh | A61F 2/30942 623/18.11 |
| 2008/0255584 A1* | 10/2008 | Beverland | A61B 5/103 703/11 |
| 2008/0287781 A1* | 11/2008 | Revie | A61B 90/36 382/131 |
| 2008/0294258 A1* | 11/2008 | Revie | A61B 5/6878 623/18.11 |
| 2008/0312663 A1* | 12/2008 | Haimerl | G06T 7/0012 128/898 |
| 2008/0319449 A1* | 12/2008 | Tuma | A61B 90/36 382/131 |
| 2009/0043556 A1 | 2/2009 | Axelson et al. | |
| 2009/0105714 A1* | 4/2009 | Kozak | A61B 34/20 600/587 |
| 2010/0030231 A1* | 2/2010 | Revie | A61B 90/36 382/128 |
| 2010/0041985 A1* | 2/2010 | Simon | A61B 6/463 378/62 |
| 2010/0081971 A1* | 4/2010 | Allison | A61F 7/00 606/1 |
| 2010/0152859 A1* | 6/2010 | Thompson | A61F 2/3609 623/20.35 |
| 2011/0013148 A1* | 1/2011 | Friese | A61B 34/10 353/30 |
| 2011/0160738 A1* | 6/2011 | McIntosh | A61B 34/20 606/102 |
| 2011/0264009 A1* | 10/2011 | Walter | A61F 2/4657 600/595 |
| 2012/0116412 A1* | 5/2012 | Penenberg | A61F 2/4609 606/102 |
| 2013/0053855 A1* | 2/2013 | Bertram, III | A61B 17/1764 606/89 |
| 2013/0072821 A1* | 3/2013 | Odermatt | A61B 5/06 600/595 |
| 2013/0114866 A1* | 5/2013 | Kasodekar | A61B 5/1071 382/128 |
| 2013/0158557 A1* | 6/2013 | Komistek | A61B 17/15 623/22.21 |
| 2013/0226190 A1* | 8/2013 | Mckinnon | A61F 2/46 606/102 |
| 2013/0324890 A1* | 12/2013 | Youssef | G01C 21/1654 600/595 |
| 2013/0332128 A1* | 12/2013 | Miles | G16H 50/50 703/6 |
| 2014/0188240 A1* | 7/2014 | Lang | A61F 2/3662 29/592 |
| 2014/0277542 A1* | 9/2014 | Stein | A61F 2/4657 623/20.32 |
| 2014/0358151 A1 | 12/2014 | Murphy et al. | |
| 2016/0008087 A1* | 1/2016 | Odermatt | A61B 34/10 703/1 |
| 2017/0258526 A1 | 9/2017 | Lang | |
| 2018/0071031 A1 | 3/2018 | Berend et al. | |
| 2019/0201155 A1* | 7/2019 | Gupta | G06T 7/33 |
| 2020/0054247 A1* | 2/2020 | Gupta | A61B 5/1071 |
| 2022/0125334 A1* | 4/2022 | Gupta | A61B 5/1071 |

FOREIGN PATENT DOCUMENTS

| | | |
|---|---|---|
| WO | WO 02/061688 A2 | 8/2002 |
| WO | WO 2006/079211 A1 | 8/2006 |
| WO | WO 2009/025783 A1 | 2/2009 |
| WO | WO-2009106812 A1 * | 9/2009 ............. A61B 34/10 |
| WO | WO 2015/120892 A2 | 8/2015 |
| WO | WO 2017/204832 A1 | 11/2017 |
| WO | WO 2018/045086 A1 | 3/2018 |

OTHER PUBLICATIONS

Canadian Office Action, CA3024840, dated Dec. 9, 2019.
China Office Action, CN 201680087996.1, dated Dec. 18, 2019.
China Office Action, CN 201780066725.2, dated Feb. 26, 2020.
EP Search Report and Opinion, EP17847501.8, dated Feb. 3, 2020.
EP Search Report, EP16903352.9, dated Dec. 13, 2019.
Extended European Search Report, EP19761216.1 dated May 3, 2022.
International Search Report and Written Opinion, PCT/US2017/049466, dated Dec. 11, 2017.
International Search Report and Written Opinion, PCT/US2019/019633, dated May 14, 2019.
International Search Report and Written Opinion, PCT/US2020/021173, dated Jul. 8, 2020.
International Search Report and Written Opinion, PCT/US2021/072042, dated Jan. 31, 2022.
Audette et al. "An algorithmic overview of surface registration techniques for medical imaging." Medical Image Analysis, vol. 4, No. 3, Sep. 1, 2000, pp. 201-217.
Besl et al., "A Method for Registration of 3-D Shapes," IEEE Transactions on Pattern Analysis and Machine Intelligence (PAMI), 14(2):239-256, Feb. 1992.
Chang CJ et al. Registration of 2D C-arm and 3D CT images for a C-arm image-assisted navigation system for spinal surgery. *Applied bionics and biomechanics*, 2015.
Dong-Soo Kwon et al. The mechanism and registration method of a surgical robot for hip arthroplasty. Proceeding/2002 IEEE International Conference on Robotics and Automation: May 11-15, 2002, Washington, D.C., IEEE Service Center, Piscataway, NJ, vol. 2, May 11, 2002, p. 1889.
Ito K et al. Direct assessment of 3D foot bone kinematics using biplanar X-ray fluoroscopy and an automatic model registration method. *Journal of Foot and Ankle Research* Dec. 2015;8(1):21.
Kim Y et al. Novel methods for 3D postoperative analysis of total knee arthroplasty using 2D-3D image registration. *Clinical Biomechanics* 26, No. 4 (2011):384-391.
Lea et al., "Registration and immobilization in robot-assisted surgery", Journal of Image Guided Surgery, pp. 1-10, 1995.
Rohlfing et al., "Chapter 11 *Quo Vadis*, Atlas-Based Segmentation?", in Handbook of Biomedical Image Analysis vol. III: Registration Models 435, 435-486 (Jasjit S. Suri et al. eds., Kluwer Academic/Plenum Publishers, NY 2005).
Vigneron L, Delport H, De Boot S. Accuracy assessment of 2D X-ray to 3D CT registration for measuring 3D postoperative implant position [white paper], 2014. http://www.materialise.com/en/resources/white-papers/accuracy-assessment-of-2d-x-ray-to-3d-ct-registration-for-measuring-3d.
Wang C et al. The impact of high-heeled shoes on ankle complex during walking in young women—In vivo kinematic study based on 3D to 2D registration technique. *Journal of Electromyography and Kinesiology* 28 (2016):7-16.

(56) References Cited

OTHER PUBLICATIONS

Xie et al. "Segmentation by surface-to-image registration." proceedings of SPIE, vol. 6144, Mar. 2, 2006, pp. 614405-1-614405-7.

* cited by examiner

| Landmark / Region | Capture Method | Used By | Approach Dependent | Captured In |
|---|---|---|---|---|
| Center of Rotation | Region | Initial / Fine | No | Pre-Op Images / Intra-Op Registration |
| Acetabulum Rim | Point | Initial / Fine | Yes | Pre-Op Images / Intra-Op Registration |
| Acetabulum Articular Surface | Point | Initial / Fine | Yes | Pre-Op Images / Intra-Op Registration |
| ASIS (Operative Side) | Point | Initial / Fine | No | Pre-Op Images / Intra-Op Registration |
| Acetabulum Rim Region | Region | Fine | Yes | Pre-Op Images / Intra-Op Registration |

FIG. 8B

SYSTEMS AND METHODS FOR INTRA-OPERATIVE PELVIC REGISTRATION

CROSS-REFERENCE TO RELATED APPLICATIONS

The present application is a continuation application of U.S. application Ser. No. 16/653,207 filed Oct. 15, 2019, which application is a continuation of U.S. application Ser. No. 16/329,157, filed Feb. 27, 2019, now U.S. Pat. No. 10,485,450, which application is a national phase application of PCT/US2017/049466, filed Aug. 30, 2017, which application claims the benefit of and priority to U.S. Provisional Patent Application No. 62/381,214, filed Aug. 30, 2016, and entitled "INTRA-OPERATIVE PELVIC REGISTRATION." All the above-identified applications are hereby incorporated by reference in their entirety.

The present application incorporates by reference the following applications in their entireties: U.S. patent application Ser. No. 12/894,071, filed Sep. 29, 2010, entitled "SURGICAL SYSTEM FOR POSITIONING PROSTHETIC COMPONENT AND/OR FOR CONSTRAINING MOVEMENT OF SURGICAL TOOL"; U.S. patent application Ser. No. 13/234,190, filed Sep. 16, 2011, entitled "SYSTEMS AND METHOD FOR MEASURING PARAMETERS IN JOINT REPLACEMENT SURGERY"; U.S. patent application Ser. No. 11/357,197, filed Feb. 21, 2006, entitled "HAPTIC GUIDANCE SYSTEM AND METHOD"; U.S. patent application Ser. No. 12/654,519, filed Dec. 22, 2009, entitled "TRANSMISSION WITH FIRST AND SECOND TRANSMISSION ELEMENTS"; U.S. patent application Ser. No. 12/644,964, filed Dec. 22, 2009, entitled "DEVICE THAT CAN BE ASSEMBLED BY COUPLING"; and U.S. patent application Ser. No. 11/750,807, filed May 18, 2007, entitled "SYSTEM AND METHOD FOR VERIFYING CALIBRATION OF A SURGICAL DEVICE".

TECHNICAL FIELD

The present disclosure relates generally to surgical systems for orthopedic joint replacement surgery and, more particularly, to methods of intra-operative pelvic registration.

BACKGROUND

Robotic systems are often used in applications that require a high degree of accuracy and/or precision, such as surgical procedures or other complex tasks. Such systems may include various types of robots, such as autonomous, tele-operated, and interactive.

Interactive robotic systems may be preferred for some types of surgery, such as joint replacement surgery, because they enable a surgeon to maintain direct, hands-on control of the surgical procedure while still achieving a high degree of accuracy and/or precision. For example, in knee replacement surgery, a surgeon can use an interactive, haptically guided robotic arm in a passive manner to sculpt bone to receive a joint implant, such as a knee implant. To sculpt bone, the surgeon manually grasps and manipulates the robotic arm to move a cutting tool (e.g., a rotating burr) that is coupled to the robotic arm to cut a pocket in the bone. As long as the surgeon maintains a tip of the burr within a predefined virtual cutting boundary or haptic boundary defined, for example, by a haptic object, the robotic arm moves freely with low friction and low inertia such that the surgeon perceives the robotic arm as essentially weightless and can move the robotic arm as desired. If the surgeon attempts to move the tip of the burr to cut outside the virtual cutting boundary, however, the robotic arm provides haptic feedback (e.g., forced resistance) that prevents or inhibits the surgeon from moving the tip of the burr beyond the virtual cutting boundary. In this manner, the robotic arm enables highly accurate, repeatable bone cuts. When the surgeon manually implants a knee implant (e.g., a patellofemoral component) on a corresponding bone cut the implant will generally be accurately aligned due to the configuration of and interface between the cut bone and the knee implant.

The above-described interactive robotic system may also be used in hip replacement surgery, which may require the use of multiple surgical tools having different functions (e.g., reaming, impacting), different configurations (e.g., straight, offset), and different weights. A system designed to accommodate a variety of tools is described in U.S. patent application Ser. No. 12/894,071, filed Sep. 29, 2010, entitled "SURGICAL SYSTEM FOR POSITIONING PROSTHETIC COMPONENT AND/OR FOR CONSTRAINING MOVEMENT OF SURGICAL TOOL", which is hereby incorporated by reference in its entirety.

During a hip replacement surgery, as well as other robotically assisted or fully autonomous surgical procedures, the patient bone is intra-operatively registered with a corresponding virtual or computer bone model to correlate the pose (i.e., position and rotational orientation) of the actual, physical bone with the virtual bone model. The patient bone (physical space) is also tracked relative to the surgical robot, haptic device, or surgical tool with at least one degree of freedom (e.g., rotating burr). In this way, the virtual cutting or haptic boundaries controlled and defined on the virtual bone model via a computer can be applied to the patient bone (physical space) such that the haptic device is constrained in its physical movement (e.g., burring) when working on the patient bone (physical space).

Intra-operative registration of the pelvis can be challenging because of the complex geometry of the pelvis and, in particular, the concave nature of the acetabulum. While certain methods exist in the art for registration of a patient pelvis, there is need in the art for registration methods that increase accuracy while decreasing registration time.

BRIEF SUMMARY

Aspects of the present disclosure may involve a system for registering patient data gathered intra-operatively of a first bone with a computer model of the first bone in a coordinate system. The first bone may include a concave portion and forming a joint with a second bone may include a convex portion. The system may include a) a surgical navigation system may include a tracking device and at least one tool configured to be tracked in its movement by the tracking device. The system may further include b) at least one computing device in communication with the surgical navigation system, the at least one computing device storing the computer model of the first bone in the coordinate system. The at least one computing device may perform the following steps: i) receiving first data points of the patient data from first intra-operatively collected points on an articular surface of the concave portion, the first data points collected using the at least one tool, the first data points corresponding in location to a first articular region on the computer model; ii) receiving a second data point from a second intra-operatively collected point on the first bone, the second data point collected using the at least one tool, the second data point corresponding in location to a second virtual data point on the computer model; iii) determining an intra-operative center of rotation from the first data points, the intra-operative center of rotation corresponding to a physical center of rotation of the second bone relative to the first bone; iv) aligning the intra-operative center of rotation with a virtual center of rotation of the computer model in the coordinate system; v) comparing a first distance between the virtual center of rotation and the second virtual data point and a second distance between the intra-operative center of rotation and the second data point; and vi) running a transformation with the patient data and the computer model so as to have them correspond with respect to position and orientation.

In certain instances, the first bone may include an ilium, the concave portion may include an acetabulum, and the second bone may include a femur, and wherein the second data point may be located on a rim of the acetabulum, an articular surface of the acetabulum, or an anterior superior iliac spine.

In certain instances, the system may further include: vii) receiving a third data point of the patient data from a third intra-operatively collected point on the first bone, the third data point collected with the at least one tool, the third data point being in a different location on the first bone than the second data point and corresponding in location to a third virtual data point on the computer model; and viii) comparing a third distance between the virtual center of rotation and the third virtual data point and a fourth distance between the intra-operative center of rotation and the third data point.

In certain instances, the first bone may include an ilium, the concave portion may include an acetabulum, and the second bone may include a femur, and wherein the second data points may be located on one of a rim of the acetabulum, an articular surface of the acetabulum, or an anterior superior iliac spine, and wherein the third data point may be located on one of a rim of the acetabulum, an articular surface of the acetabulum, or an anterior superior iliac spine.

In certain instances, the first bone may include a scapula, the concave portion may include a glenoid cavity, and the second bone may include a humerus, and wherein the second data points may be located on one of a rim of the glenoid cavity, an articular surface of the glenoid cavity, or another portion of the scapula, and wherein the third data point may be located on one of a rim of the glenoid cavity, an articular surface of the glenoid cavity, or another portion of the scapula.

In certain instances, step iii) further may include computing a spherical surface formed by the first data points.

In certain instances, the system may further include computing an intra-operative radius of the spherical surface, the intra-operative radius extending from the intra-operative center of rotation to generally the first data points.

In certain instances, the system may further include comparing the intra-operative radius to a virtual radius extending from the virtual center of rotation of the computer model to the first articular region on the computer model.

In certain instances, registration may be acceptable if a difference between the intra-operative radius and the virtual radius may be about 3 mm or less.

In certain instances, the at least one tool may include at least one of a free-hand navigation probe, and an arm of a surgical robot.

In certain instances, the joint may include one of a hip joint, a shoulder joint, a knee joint, an elbow joint, or an ankle joint.

Aspects of the present disclosure may involve one or more tangible computer-readable storage media storing computer-executable instructions for performing a computer process on a computing system. The computer process may include a) receiving a plurality of first data points of patient data points captured on a first patient bone in a first location using a tracking device of a navigation system, the first patient bone may include a concave portion forming a joint with a convex portion of a second patient bone, the plurality of first data points representing a first virtual surface profile of the first patient bone at the first location. The computer process may further include b) receiving a second data point of patient data points captured on the first patient bone in a second location using the tracking device, the second location being different than the first location. The computer process may further include c) determining a first center of rotation from the plurality of first data points, the first center of rotation being representative of a physical center of rotation of the second patient bone relative to the first patient bone. The computer process may further include include d) locationally matching the first center of rotation with a virtual center of rotation of a computer model of the first patient bone, wherein the plurality of first data points, the second data point, the first center of in the coordinate system, the computer model, and the virtual center of rotation being in a common coordinate system. The computer process may further include e) locationally matching the second data point and a second virtual data point of the computer model to register the patient data points with the computer model with respect to position and orientation, the second virtual data point located on the computer model in a location corresponding to the second location on the first patient bone.

In certain instances, the joint may include one of a hip joint, a shoulder joint, a knee joint, an elbow joint, or an ankle joint.

In certain instances, the first location may include an articular surface.

In certain instances, step c) further may include computing a spherical surface formed by the plurality of first data points.

In certain instances, the one or more tangible computer-readable storage media may further include computing a first radius of the spherical surface, the first radius extending from the first center of rotation to the plurality of first data points.

In certain instances, the one or more tangible computer-readable storage media may further include comparing the first radius to a virtual radius extending from the virtual center of rotation of the computer model.

In certain instances, the information in step e) may include a first length between the second data point and the first center of rotation.

In certain instances, the first length may be compared with a virtual distance between the second virtual data point and the virtual center of rotation.

In certain instances, the second data point may be located on a rim of the concave portion or an articular surface of the concave portion.

In certain instances, the second data point may be located on a rim of the concave portion or an articular surface of the concave portion, the computer process further may include:

f) receiving a third data point of the patient data points captured on the first patient bone using the tracking device, the third data point corresponding in location to a third virtual data point on the computer model, the third data point being different than the second data point and the plurality of first data points; and g) locationally matching the third data point and the third virtual data point to register the first patient bone with the computer model.

In certain instances, the third data point may be an anatomical landmark remote from the joint.

In certain instances, remote from the joint may include a distance of at least 10 cm.

In certain instances, the first patient bone may be an ilium and the anatomical landmark may be an anterior superior iliac spine.

In certain instances, the second information in step g) further may include comparing a first vector extending between the first center of rotation to the third data point and a second vector extending between the virtual center of rotation to the third virtual data point.

In certain instances, an angular difference between the first vector and the second vector in at least one plane may be used to determine registration accuracy.

In certain instances, the third data point, second data point, and the plurality of data points are acceptable if the third data point, the second data point, and the first center of rotation are not collinear.

In certain instances, the computer model may be generated from at least one of pre-operative images of the first patient bone, and intra-operative data gathering of the first patient bone.

Aspects of the present disclosure may involve a computerized method of intra-operatively registering patient data associated with a first bone with a computer model of the first bone in a coordinate system. The first bone may include a concave portion and forming a joint with a second bone may include a convex portion. The computerized method may include a) receiving first data points of the patient data from first intra-operatively collected points on an articular surface of the concave portion of the first bone, the first data points collected with a tracking device of a navigation system. The computerized method may further include b) receiving a second data point of the patient data from a second intra-operatively collected point on the first bone, the second data point collected with the tracking device, the second data point corresponding in location to a second virtual data point on the computer model. The computerized method may further include c) determining an intra-operative center of rotation of the second bone relative to the first bone from the first data points. The computerized method may further include d) locationally matching the intra-operative center of rotation with a virtual center of rotation of the computer model in the coordinate system. The computerized method may further include e) comparing a first distance between the virtual center of rotation and the second virtual data point and a second distance between the intra-operative center of rotation and the second data point.

In certain instances, the second data point may be located on a rim of the concave portion, an articular surface of the concave portion, or an another portion of the first bone.

In certain instances, the computerized method may further include: f) receiving a third data point of the patient data from a third intra-operatively collected point on the first bone, the third data point collected with the tracking device, the third data point being in a different location on the first bone than the second data point and corresponding in location to a third virtual data point on the computer model; and g) comparing a third distance between the virtual center of rotation and the third virtual data point and a fourth distance between the intra-operative center of rotation and the third data point.

In certain instances, the joint may include one of a hip joint, a shoulder joint, a knee joint, an elbow joint, or an ankle joint.

In certain instances, step c) further may include computing a spherical surface formed by the first data points.

In certain instances, the computerized method may further include computing an intra-operative radius of the spherical surface, the intra-operative radius extending from the intra-operative center of rotation to the first data points.

In certain instances, the computerized method may further include comparing the intra-operative radius to a virtual radius extending from the virtual center of rotation of the computer model.

Aspects of the present disclosure may involve a computerized method of registering first patient data associated with a first patient bone and a computer model of the first patient bone in a coordinate system with respect to translation and rotation. The first patient bone may include a concave portion forming a joint with a convex portion of a second patient bone. The computerized method may include a) locking the translation between the first patient data and the computer model of the first patient bone by: i) receiving a plurality of first data points of the first patient data, the plurality of first data points corresponding to first points collected on the first patient bone in a first location, the first points collected with a tracking device of a navigation system; ii) determining an intra-operative center of rotation of the convex portion of the second patient bone relative to the concave portion of the first patient bone from the plurality of first data points; and iii) aligning the intra-operative center of rotation with a virtual center of rotation of the computer model of the first patient bone in the coordinate system.

In certain instances, the computerized method may further include: b) locking the rotation between the first data points and the computer model of the first patient bone by: i) capturing a second data point of the first data points on the first patient bone using the tracking device, the second data point being in a different location than the plurality of first data points and corresponding in location to a second virtual data point on the computer model; and ii) using information associated with the second data point and the second virtual data point to lock the rotation of the first data points with the computer model.

In certain instances, the joint may include a hip joint, a shoulder joint, a knee joint, an elbow joint, or an ankle joint.

In certain instances, the first location may include an articular surface.

In certain instances, step c) further may include computing a spherical surface formed by the plurality of first data points.

In certain instances, the computerized method may further include computing an intra-operative radius of the spherical surface, the intra-operative radius extending from the intra-operative center of rotation to the plurality of first data points.

In certain instances, the computerized method may further include comparing the intra-operative radius to a virtual radius extending from the virtual center of rotation of the computer model.

In certain instances, the first patient bone may include an ilium having an acetabulum, the second patient bone may include a femur, and the joint may include a hip joint, and wherein the first location may be on an articular surface of the acetabulum, and the different location may be on a rim of the acetabulum, the articular surface of the acetabulum, an anterior superior iliac spine of the ilium, or an anterior superior iliac spine of a non-operative ilium.

Aspects of the present disclosure may involve a system for guided landmark capture during a registration procedure involving registering intra-operative data associated with a first bone of a patient with a computer model of the first bone. The system may include a) a surgical navigation system may include a tracking device and at least one tool configured to be tracked in its movement by the tracking device. The system may further include b) a display device. The system may further include c) at least one computing device in electrical communication with the display device and the surgical navigation system, the at least one computing device may include: an input; an output; a memory; and a central processing unit ("CPU") in electrical communication with the input, the output and the memory, the memory may include software for operating a graphical user interface ("GUI"), the at least one computing device configured to: i) display the GUI, and the computer model of the first bone on the display device, the GUI may include a virtual point displayed on the computer model of the first bone, the virtual point corresponding to a physical point on the first bone for intra-operatively capturing with the at least one tool, the GUI may further include a graphic at least partially surrounding the virtual point, the graphic being spaced apart from the virtual point by a radius. The GUI may further be configured to ii) adjust a size of the radius of the graphic based on a change in distance between the at least one tool and the physical point on the first bone.

In certain instances, the size of the radius of the graphic decreases as the change in distance decreases.

In certain instances, the size of the radius of the graphic increases as the change in distance increases.

In certain instances, the graphic may include at least one of an arrow and a circle.

In certain instances, the graphic changes color when the physical point may be intra-operatively captured.

In certain instances, the change in the distance may be between a tip of the at least one tool and the physical point on the first bone.

In certain instances, the at least one tool may include at least one of a navigation probe, and a tip of a tool coupled with a robotic arm.

BRIEF DESCRIPTION OF THE DRAWINGS

FIG. 8B illustrates a table showing various characteristics of many of the steps of the pelvic registration method of FIG. 8A.

DETAILED DESCRIPTION

I. Overview

Figure 1A:
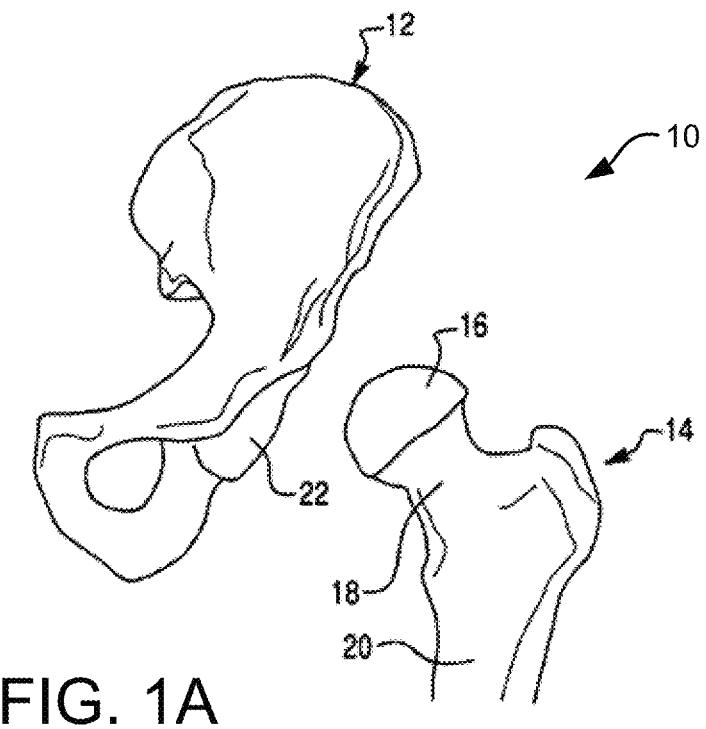
FIG. 1A is a perspective view of a femur and a pelvis.
Figure 1B:
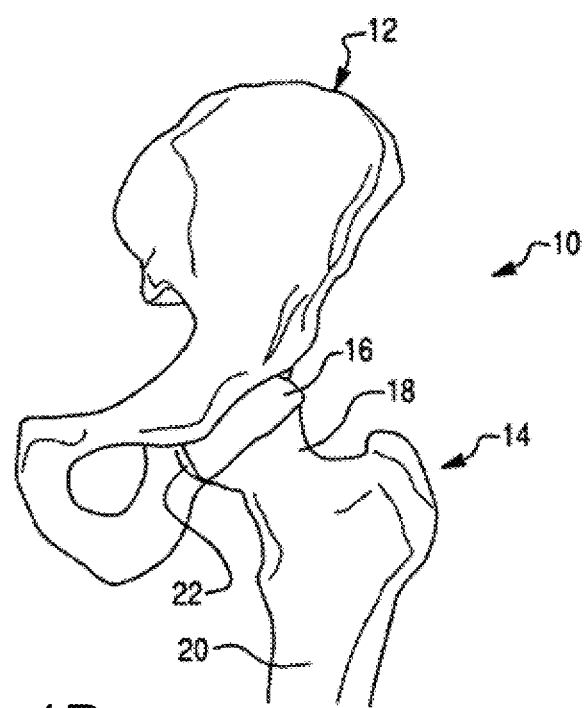
FIG. 1B is a perspective view of a hip joint formed by the femur and pelvis of FIG. 1A.

The hip joint is the joint between the femur and the pelvis and primarily functions to support the weight of the body in static (e.g., standing) and dynamic (e.g., walking) postures. FIG. 1A illustrates the bones of an operative side of a hip joint 10, which include a left pelvis or ilium 12 and a proximal end of a left femur 14. While a right pelvis and proximal end of a right femur is not shown in FIG. 1A, such a discussion herein is applicable to both the right and the left femur and pelvis without limitation. Continuing on, the proximal end of the femur 14 includes a femoral head 16 disposed on a femoral neck 18. The femoral neck 18 connects the femoral head 16 to a femoral shaft 20. As shown in FIG. 1B, the femoral head 16 fits into a concave socket in the pelvis 12 called the acetabulum 22, thereby forming the hip joint 10. The acetabulum 22 and femoral head 16 are both covered by articular cartilage that absorbs shock and promotes articulation of the joint 10.

Figure 2B:
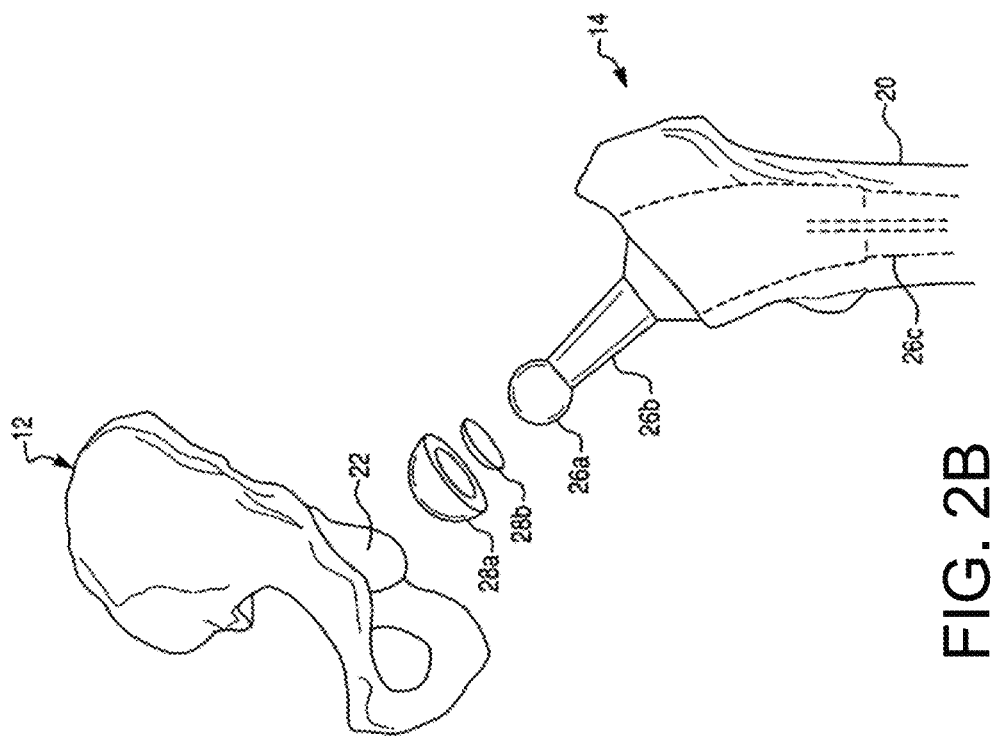
FIG. 2B is a perspective view illustrating placement of the femoral component and acetabular component of FIG. 2A in relation to the femur and pelvis of FIG. 1A, respectively.
Figure 2A:
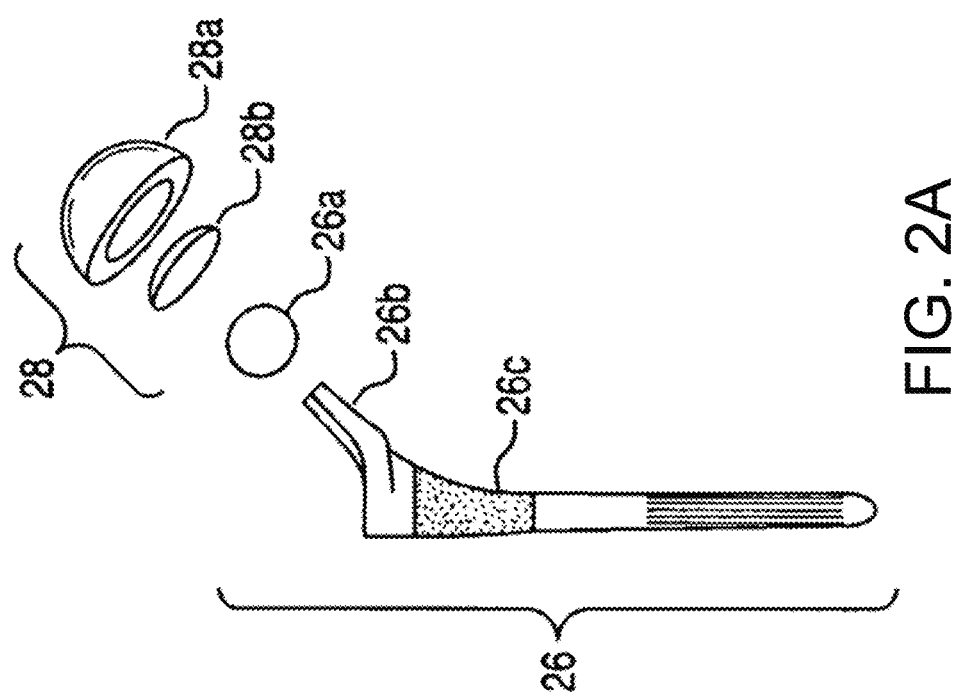
FIG. 2A is an exploded perspective view of a femoral component and an acetabular component for a total hip replacement procedure.

Over time, the hip joint 10 may degenerate (e.g., due to osteoarthritis) resulting in pain and diminished functionality. As a result, a hip replacement procedure, such as total hip arthroplasty or hip resurfacing, may be necessary. During hip replacement, a surgeon replaces portions of a patient's hip joint 10 with artificial components. In total hip arthroplasty, the surgeon removes the femoral head 16 and neck 18 and replaces the native bone with a prosthetic femoral component 26 comprising a head 26a, a neck 26b, and a stem 26c (shown in FIG. 2A). As shown in FIG. 2B, the stem 26c of the femoral component 26 is anchored in a cavity the surgeon creates in the intramedullary canal of the femur 14. Alternatively, if disease is confined to the surface of the femoral head 16, the surgeon may opt for a less invasive approach in which the femoral head is resurfaced (e.g., using a cylindrical reamer) and then mated with a prosthetic femoral head cup (not shown). Similarly, if the natural acetabulum 22 of the pelvis 12 is worn or diseased, the surgeon resurfaces the acetabulum 22 using a reamer and replaces the natural surface with a prosthetic acetabular component 28 comprising a hemispherical shaped cup 28a (shown in FIG. 2A) that may include a liner 28b. To install the acetabular component 28, the surgeon connects the cup 28a to a distal end of an impactor tool and implants the cup 28a into the reamed acetabulum 22 by repeatedly striking a proximal end of the impactor tool with a mallet. If the acetabular component 28 includes a liner 28b, the surgeon snaps the liner 28b into the cup 28a after implanting the cup 28a. Depending on the position in which the surgeon places the patient for surgery, the surgeon may use a straight or offset reamer to ream the acetabulum 22 and a straight or offset impactor to implant the acetabular cup 28a. For example, a surgeon that uses a postero-lateral approach may prefer straight reaming and impaction whereas a surgeon that uses an antero-lateral approach may prefer offset reaming and impaction.

II. Exemplary Robotic System

Figure 3A:
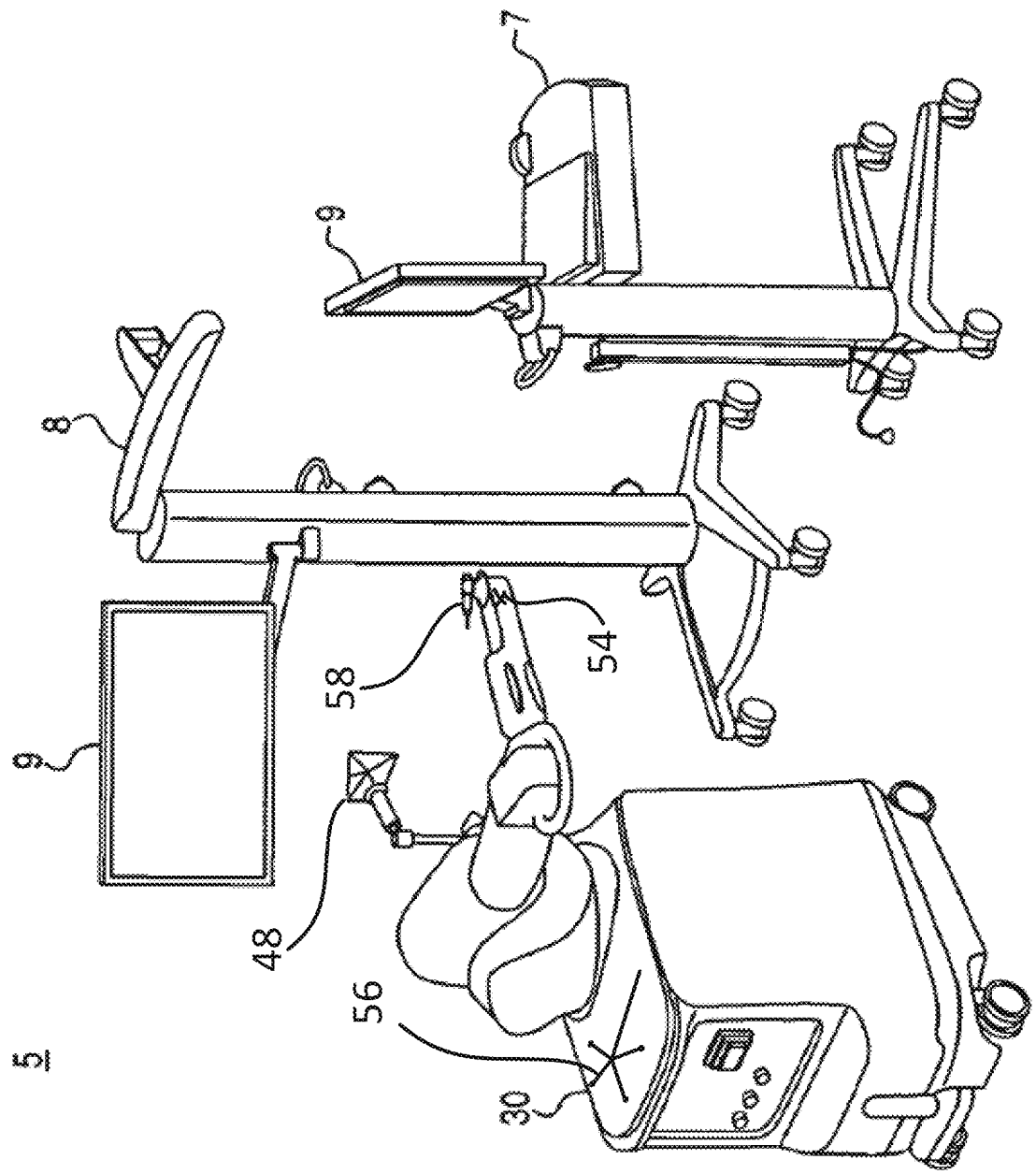
FIG. 3A is a perspective view of an embodiment of a surgical system.

A surgical system described herein may be utilized to perform hip replacement, as well as other surgical procedures. As shown in FIG. 3A, an embodiment of a surgical system 5 for surgical applications according to the present disclosure includes a computer assisted navigation system 7, a tracking device 8, a computer 15, a display device 9 (or multiple display devices 9), and a robotic arm 30.

Figure 3B:
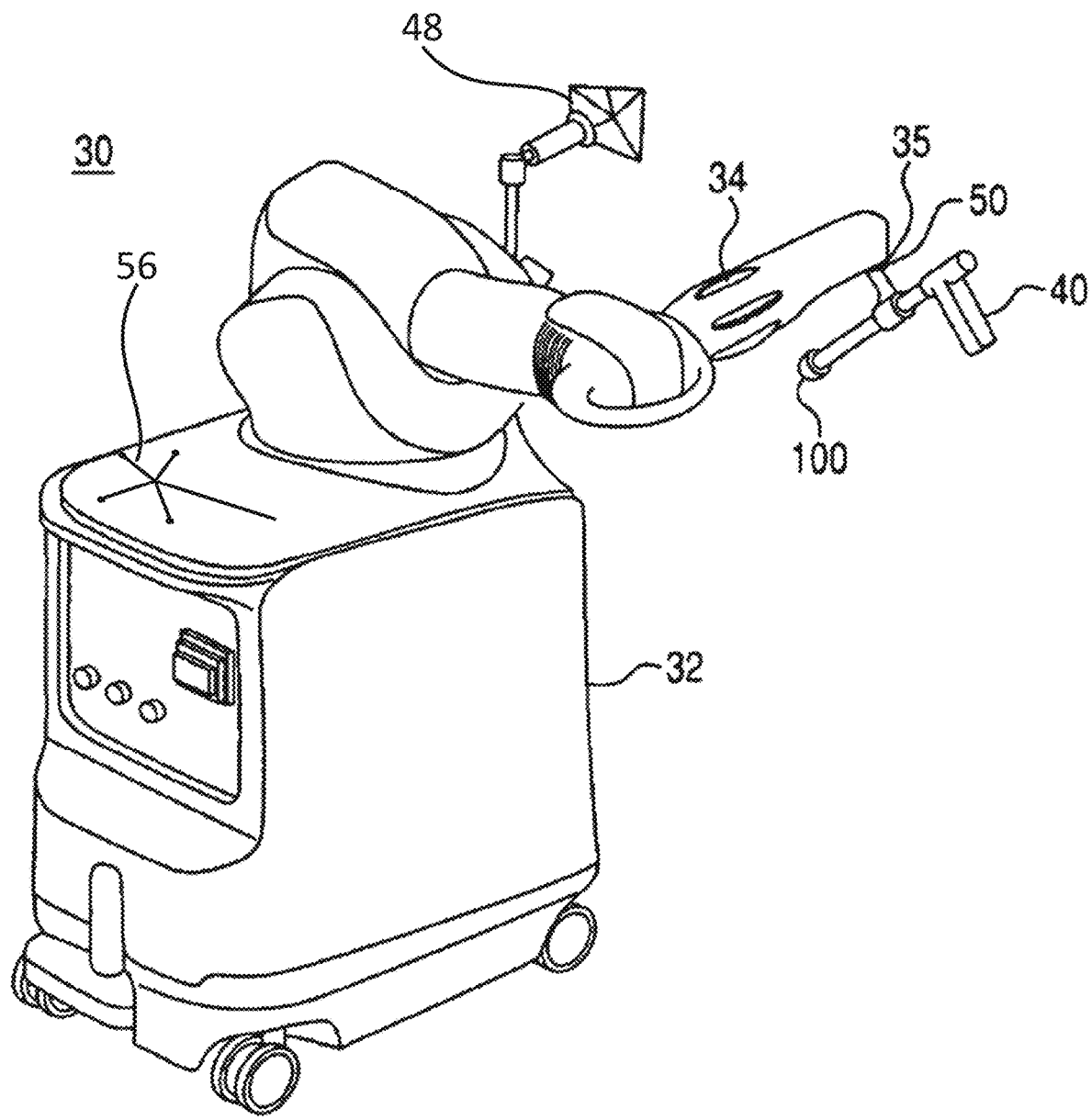
FIG. 3B is a perspective view of an embodiment of a robotic arm of the surgical system of FIG. 3A.

The robotic arm 30 can be used in an interactive manner by a surgeon to perform a surgical procedure on a patient, such as a hip replacement procedure. As shown in FIG. 3B, the robotic arm 30 includes a base 32, an articulated arm 34, a force system (not shown), and a controller (not shown). A surgical tool 58 (e.g., a rotary burring device as seen in FIG. 3A, an end effector 40 having an operating member as seen in FIG. 3B) is coupled to an end of the articulated arm 34, and the surgeon manipulates the surgical tool 58 by grasping and manually moving the articulated arm 34 and/or the surgical tool.

The force system and controller are configured to provide control or guidance to the surgeon during manipulation of the surgical tool. The force system is configured to provide at least some force to the surgical tool via the articulated arm 34, and the controller is programmed to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. patent application Ser. No. 11/357,197 (Pub. No. US 2006/0142657), filed Feb. 21, 2006, and/or U.S. patent application Ser. No. 12/654,519, filed Dec. 22, 2009, each of which is hereby incorporated by reference herein in its entirety. In a certain embodiment the surgical system is the RIO™ Robotic Arm Interactive Orthopedic System manufactured by MAKO Surgical Corp. of Fort Lauderdale, Fla. The force system and controller are preferably housed within the robotic arm 30.

The tracking device 8 is configured to track the relative locations of the surgical tool 58 (coupled to the robotic arm 30) and the patient's anatomy. The surgical tool 58 can be tracked directly by the tracking device 8. Alternatively, the pose of the surgical tool can be determined by tracking the location of the base 32 of the robotic arm 30 and calculating the pose of the surgical tool 58 based on joint encoder data from joints of the robotic arm 30 and a known geometric relationship between the surgical tool and the robotic arm 30. In particular, the tracking device 8 (e.g., an optical, mechanical, electromagnetic, or other known tracking system) tracks (or enables determination of) the pose (i.e., position and orientation) of the surgical tool and the patient's anatomy so the navigation system 7 knows the relative relationship between the tool and the anatomy.

In operation, a user (e.g., a surgeon) manually moves the robotic arm 30 to manipulate the surgical tool 58 (e.g., the rotary burring device, the end effector 40 having an operating member) to perform a surgical task on the patient, such as bone cutting or implant installation. As the surgeon manipulates the tool 58, the tracking device 8 tracks the location of the surgical tool and the robotic arm 30 provides haptic (or force) feedback to limit the surgeon's ability to move the tool 58 beyond a predefined virtual boundary that is registered (or mapped) to the patient's anatomy, which results in highly accurate and repeatable bone cuts and/or implant placement. The robotic arm 30 operates in a passive manner and provides haptic feedback when the surgeon attempts to move the surgical tool 58 beyond the virtual boundary. The haptic feedback is generated by one or more actuators (e.g., motors) in the robotic arm 30 and transmitted to the surgeon via a flexible transmission, such as a cable drive transmission. When the robotic arm 30 is not providing haptic feedback, the robotic arm 30 is freely moveable by the surgeon and preferably includes a virtual brake that can be activated as desired by the surgeon. During the surgical procedure, the navigation system 7 displays images related to the surgical procedure on one or both of the display devices 9.

To aid in tracking the various pieces of equipment within the system, the robotic arm 30 may include a device marker 48 to track a global or gross position of the robotic arm 30, a tool end marker 54 to track the distal end of the articulating arm 34, and a free-hand navigation probe 56 for use in the registration process. Each of these markers 48, 54, 56 (among others such as navigation markers positioned in the patient's bone) is trackable by the tracking device 8 with optical cameras, for example.

The computer 15 may include a display and an input device (e.g., keyboard, mouse) and is configured to communicate with the navigation system 7, the tracking device 8, the various display devices 9 in the system, and the robotic arm 30. Furthermore, the computer 15 may receive information related to a particular surgical procedure and perform various functions related to performance of the surgical procedure. For example, the computer 15 may have software as necessary to perform functions related to image analysis, surgical planning, registration, navigation, image guidance, and haptic guidance. A more detailed analysis of an example computing system having one or more computing units that may implement various systems and methods discussed herein, is described subsequently in reference to FIG. 14.

FIG. 3B depicts an end effector 40 particularly suited for use in robotic assisted hip arthroplasty. The end effector 40 is configured to be mounted to an end of the robotic arm 30. The end effector 40 includes a mounting portion 50, a housing, a coupling device, and a release member. The end effector 40 is configured to individually and interchangeably support and accurately position multiple operating members relative to the robotic arm 30. As seen in FIG. 3B, the end effector 40 is coupled to an operating member 100. The end effector 40 and related tools, systems, and methods are described in U.S. patent application Ser. No. 12/894,071, filed Sep. 29, 2010, which is hereby incorporated by reference in its entirety.

The mounting portion (or mount) 50 preferably couples the end effector 40 to the robotic arm 30. In particular, the mounting portion 50 extends from the housing and is configured to couple the end effector 40 to a corresponding mounting portion 35 of the robotic arm 30 using, for example, mechanical fasteners, such that the mounting portions are fixed relative to one another. The mounting portion 50 can be attached to the housing or formed integrally with the housing and is configured to accurately and repeatably position the end effector 40 relative to the robotic arm 30. In one embodiment, the mounting portion 50 is a semi-kinematic mount as described in U.S. patent application Ser. No. 12/644,964, filed Dec. 22, 2009, and hereby incorporated by reference herein in its entirety.

The end effector 40 in FIG. 3B is one example of a surgical tool that can be tracked and used by the surgical robotic arm 30. Other tools (e.g., drills, burrs) as known in the art can be attached to the robotic arm for a given surgical procedure.

III. Pre-operative Planning a Surgical Procedure

Prior to the surgical procedure, a preoperative CT (computed tomography) scan of the patient's pelvis 12 and femur 14 is generated with a medical imaging device. While the discussion will focus on CT scans, other imaging modalities (e.g., MRI) may be similarly be employed. Additionally and alternatively, X-ray images derived from the CT scan and/or the three dimensional models 512, 514 can be used for surgical planning, which may be helpful to surgeons who are accustomed to planning implant placement using actual X-ray images as opposed to CT based models. The CT scan may be performed by the surgeon or at an independent imaging facility. Additionally or alternatively, intra-operative imaging methods may be employed to generate a patient model of the bone. For example, various boney surfaces of interest may be probed with a tracked probe to generate a surface profile of the surface of interest. The surface profile may be used as the patient bone model. Accordingly, the present disclosure is applicable to all methods of generating a patient bone model or a portion thereof.

Figure 4:
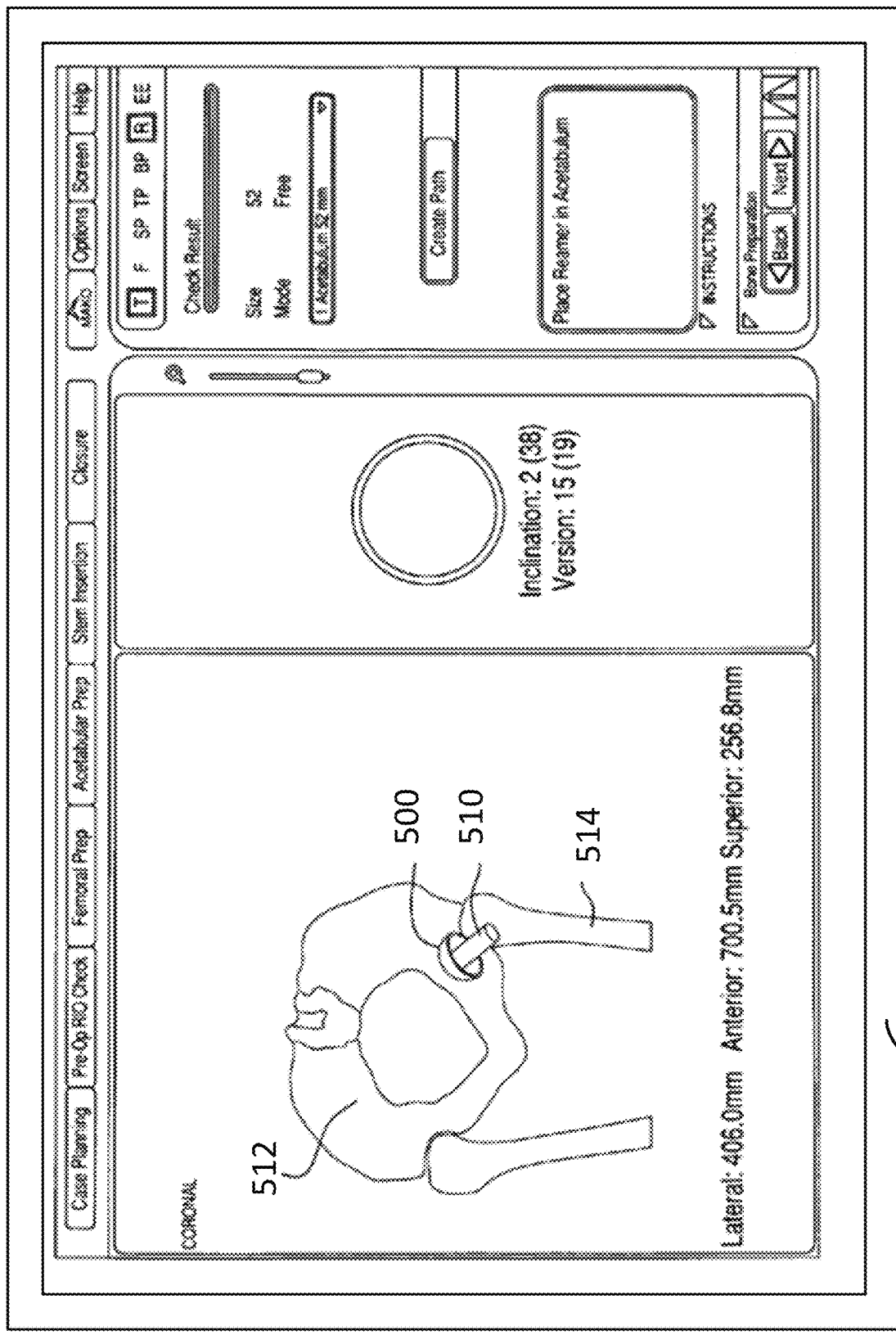
FIG. 4 illustrates an embodiment of a computer display for use during a surgical procedure.

As shown in FIG. 4, the CT scan or data from the CT scan is segmented and to obtain a three dimensional model 512 of the pelvis 12 and a three dimensional model 514 of the femur 14. The three dimensional models 512, 514 are used by the surgeon to construct a surgical plan. The surgeon generates a surgical plan by designating a desired pose (i.e., position and orientation) of the acetabular component and the femoral component relative to the models 512, 514 of the patient's anatomy. For example, a planned pose 500 of the acetabular cup can be designated and displayed on a computer display, such as the display device 9. During the surgical procedure, motion of the patient's anatomy and the surgical tool in physical space are tracked by the tracking device 8, and these tracked objects are registered to corresponding models in the navigation system 7 (image space). As a result, objects in physical space are correlated to corresponding models in image space. Therefore, the surgical system 5 knows the actual position of the surgical tool relative to the patient's anatomy and the planned pose 500, and this information is graphically displayed on the display device 9 during the surgical procedure.

In certain embodiments, the models 512, 514 may be of the full bone surfaces 12, 14 respectively. In certain embodiments, the models 512, 514 may be trimmed three dimensional models providing only critical regions of interest such as the acetabulum 22 and femoral head 16. That is, the trimmed three dimensional models represent only a portion of the full bone models 512, 514. In certain embodiments, the models 512, 514 may be the combination of multiple models. For example, model 512 may be the combination of individual three dimensional models of the operative pelvis, non-operative pelvis, and spine.

IV. Intra-operative Procedures

A.

Figure 5:
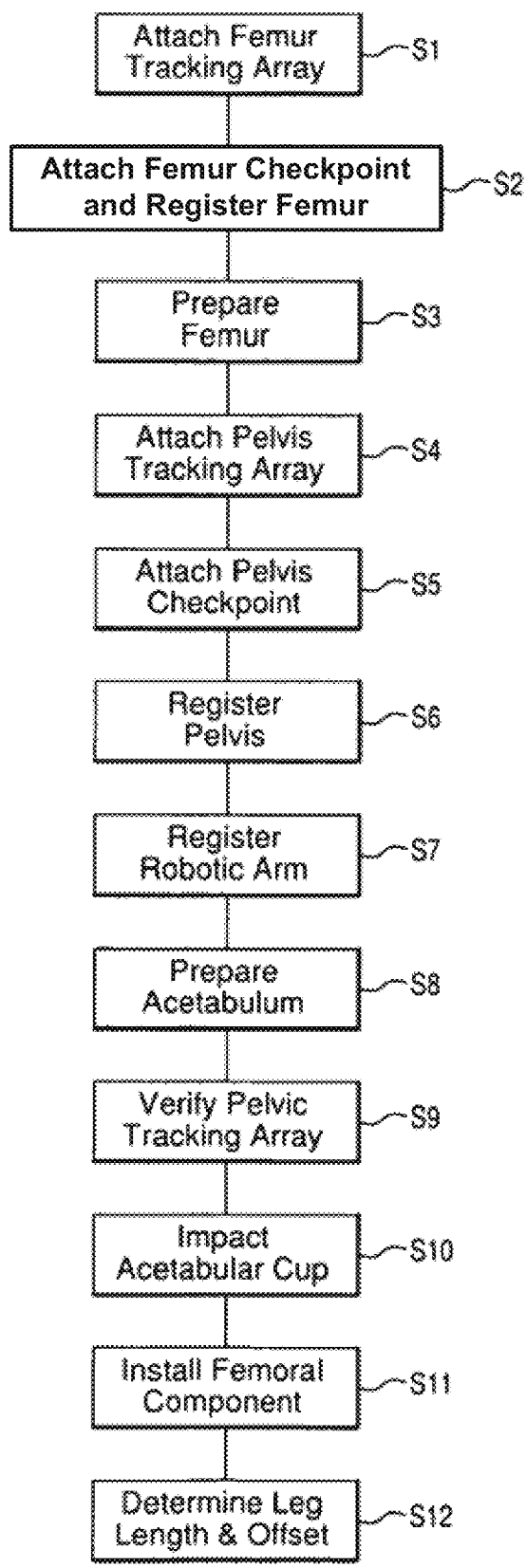
FIG. 5 illustrates an embodiment of steps of a hip replacement procedure.

FIG. 5 illustrates an embodiment of intra-operative steps of performing a total hip replacement. In this embodiment, steps S1-S7, S9, S11, and S12 can be performed with or without robotic assistance. In other embodiments, S1-S2 may not be required, S3-S5 could be done before S1-S2, and S7 could be done at any point before S8. Steps S8 and S10 are preferably performed using the robotic arm 30. For example, step S8 (reaming) can be performed using the robotic arm 30 of FIG. 3 with the end effector 40 coupled to the operating member 100, and step S10 (impacting) can be performed using the robotic arm 30 with the end effector 40 coupled to another operating member.

In step S1 of the surgical procedure, a tracking array is attached to the femur 14 to enable the tracking device 8 to track motion of the femur 14. In step S2, the femur 14 is registered (using any known registration technique) to correlate the pose of the femur 14 (physical space) with the three dimensional model 514 of the femur 14 in the navigation system 7 (image space). Additionally, the femur checkpoint is attached. In step S3, the femur 14 is prepared to receive a femoral implant (e.g., the femoral component 26) using a navigated femoral broach.

B. Tracking and Registration of Pelvis

1. Overview

In step S4 of FIG. 5, an acetabular tracking array is attached to the pelvis 12 to enable the tracking device 8 to track motion of the pelvis 12. In step S5, a checkpoint is attached to the pelvis 12 for use during the surgical procedure to verify that the acetabular tracking array has not moved in relation to the pelvis 12. The checkpoint can be, for example, a checkpoint as described in U.S. patent application Ser. No. 11/750,807 (Pub. No. US 2008/0004633), filed May 18, 2007, and hereby incorporated by reference herein in its entirety.

Figure 6:
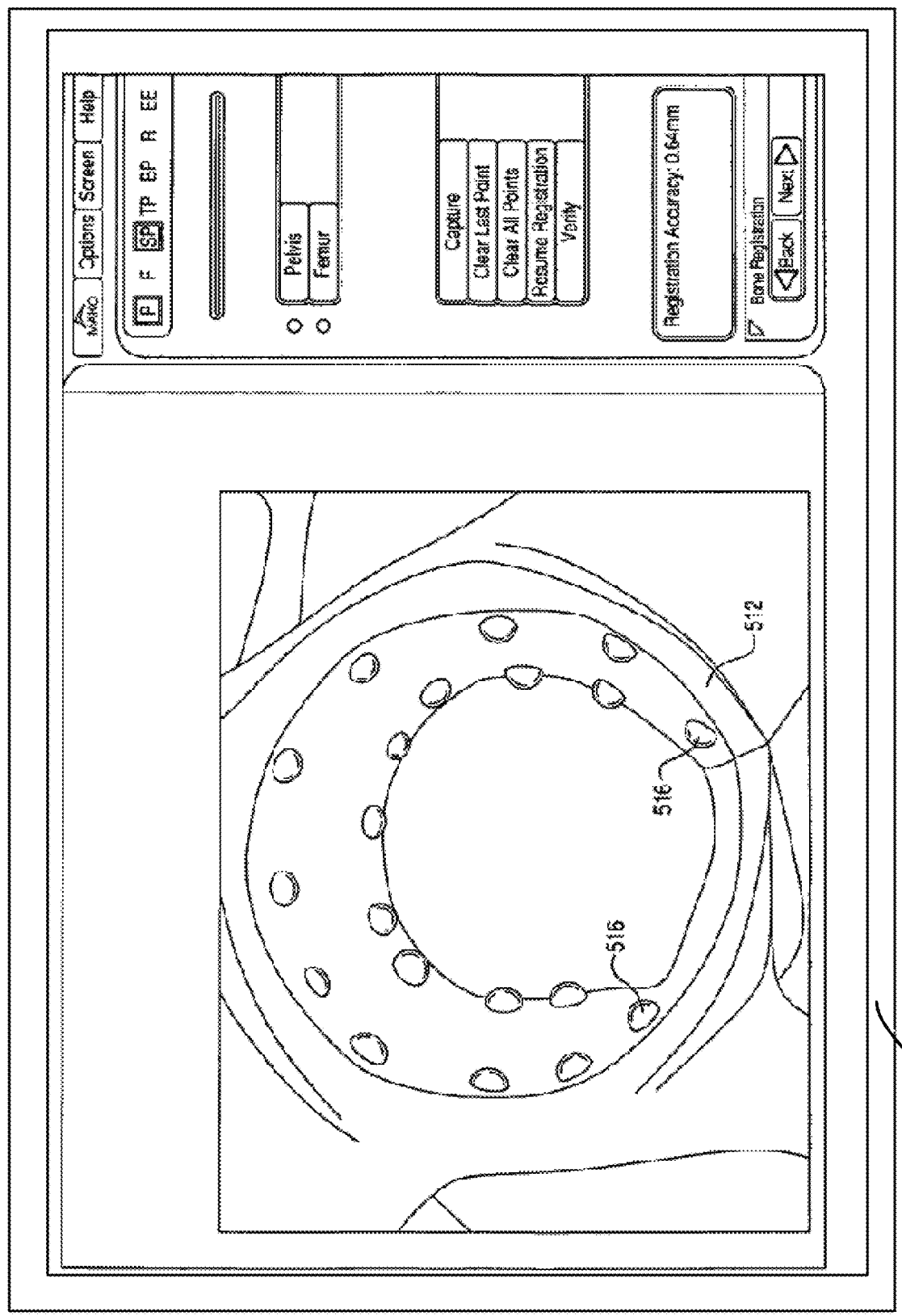
FIGS. 6 and 7 illustrate an embodiment of a pelvic registration method shown on a display screen.

In step S6, the pelvis 12 is registered to correlate the pose of the pelvis 12 (physical space) with the three dimensional model 512 of the pelvis 12 in the navigation system 7 (image space). In certain embodiments, as shown in FIG. 6, registration is accomplished using the tracked navigation probe 56 to collect points on the pelvis 12 (physical space) that are then matched to corresponding points on the three dimensional model 512 of the pelvis 12 (image space). In certain embodiments, registration may be accomplished using a tool that is coupled to the end effector 40 of the robotic arm 30. In certain embodiments, registration may be accomplished with any tool or device that is tracked with the navigation system 7. Two methods of registering the three dimensional model 512 of the pelvis (image space) and the pelvis 12 (physical space) are described in the subsequent sections of this application.

2. First Pelvic Registration Method

As shown in FIG. 6, the display device 9 may show the representation 512 of the pelvis 12, including one or more registration points 516. The registration points 516 help the surgeon understand where on the actual anatomy to collect points with the tracked probe. The registration points 516 can be color coded to further aid the surgeon. For example, a registration point 516 on the pelvis 12 to be collected next with the tracked probe can be colored yellow, while registration points 516 that have already been collected can be colored green and registration points 516 that will be subsequently collected can be colored red. After registration, the display device 9 can show the surgeon how well the registration algorithm fit the physically collected points to the representation 512 of the pelvis 12.

Figure 7:
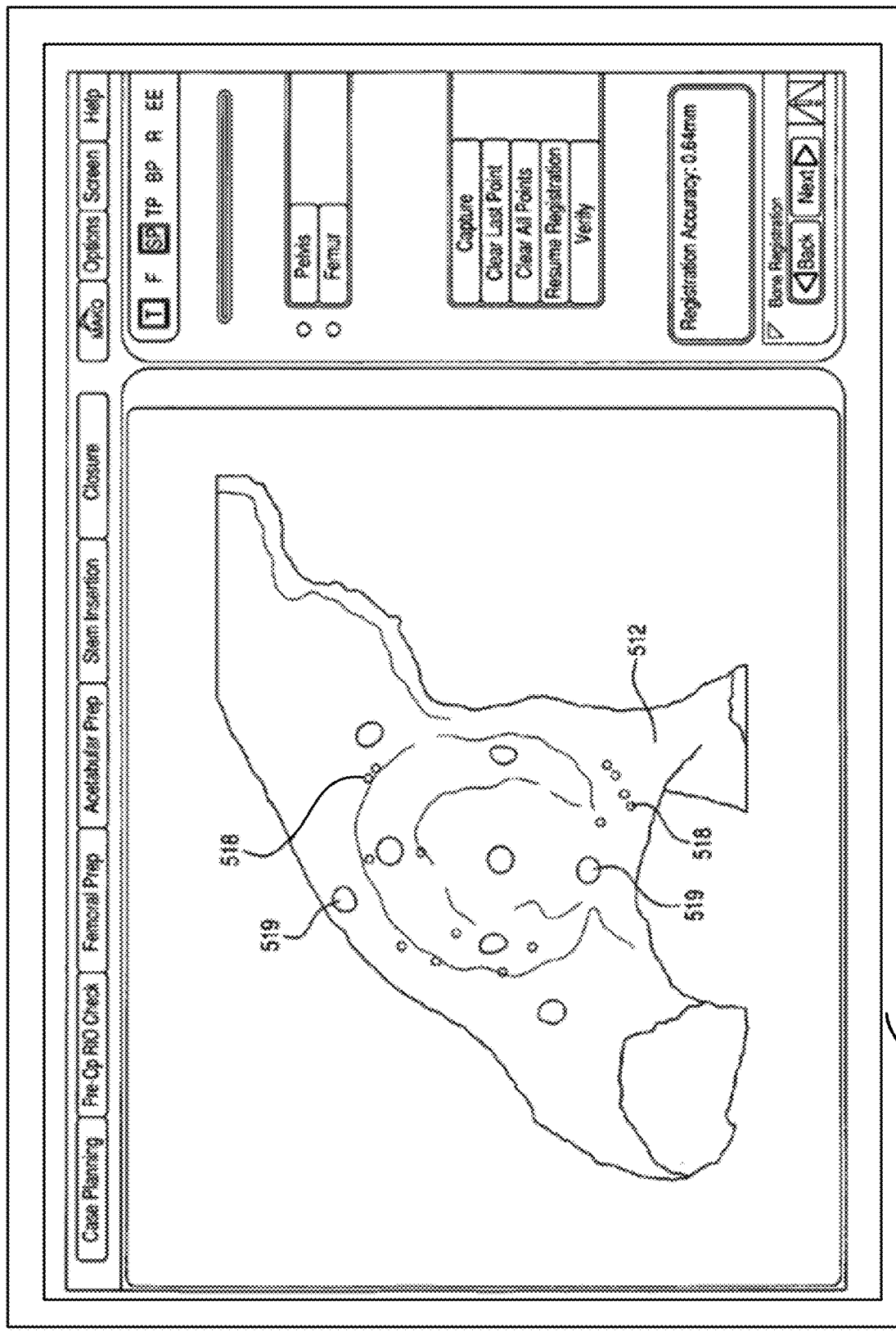

For example, as shown in FIG. 7, error points 518 can be displayed to illustrate how much error exists in the registration between the surface of the representation 512 and the corresponding surface of the physical pelvis 12. In one embodiment, the error points 518 can be color coded, for example, with error points 518 representing minimal error displayed in green and error points 518 representing increasing amounts of error displayed in blue, yellow, and red. As an alternative to color coding, error points 518 representing different degrees of error could have different shapes or sizes. Verification points 519 can also be displayed. The verification points 519 illustrate to the surgeon where to collect points with the tracked probe to verify the registration. When a registration point 519 is collected, the software of the navigation system 7 displays the error (e.g., numerically in millimeters) between the actual point collected on the anatomy and the registered location of the representation 512 in physical space. If the registration error is too high, the surgeon re-registers the pelvis 12 by repeating the registration process of step S6.

This type of registration method requires the surgeon to continually switch his or her focus from the display device 9 showing the representation 512 of the pelvis 12, including one or more registration points 516, to the patient's physical pelvis 12 in order to collect accurate points. Switching focus takes time, and accurately estimating where the registration points 516 are on the patient's physical pelvis 12 takes even more time. In such a registration method described in this section, it may take at least forty-three points to complete an accurate registration.

3. Second Pelvic Registration Method

This section describes another registration method for registering the patient pelvis 12 (physical space) with the three dimensional model 512 (image space) of the pelvis 12 using a tracked probe 56 or other tool (e.g., end of robotic arm 30). The method described in this section may reduce the total number of collected points as compared with the previously described registration method. For example, with the method described in this section, a surgeon may complete an accurate registration with thirty-two points or less. Additionally, much of the registration described in this section is a region-based point collection, as opposed to a point-based point collection. In a region-based point collection, the surgeon is permitted to collect points within a region of the patient's bone, as opposed to an exact point as identified on the three dimensional bone model 512. This permits the surgeon to focus on the patient's anatomy, and collect points within the permitted region on the bone without having to switch his or her focus to the display screen 9 and back to the patient's physical pelvis 12. Collecting points within a permitted region increases accuracy as it is easier for the surgeon to collect points within a region encompassing many possible locations of permissible points, as compared with a single permissible point.

The patient pelvis 12 is referred to as in the "physical space" because the surgeon is physically using the tracked probe 56 to contact the patient pelvis 12 intra-operatively where the position and orientation of the probe 56 is known and tracked by the tracking device 8 and the navigation system 7. The three dimensional model 512 of the pelvis 12 is referred to as in the "image space" because the model 512 is a computerized representation of the pelvis 12, which, in certain implementations, may be taken from pre-operative medical images (e.g., CT, MIl) of the patient pelvis 12. As stated previously, in certain implementations, the model 512 of the pelvis may be generated other ways, such as via intra-operatively tracking the pelvis over the bone surface to generate a bone surface profile, and in some embodiments a generic pelvis model may be presented.

In sum, use of the terms "physical space" and "image space" are utilized herein to clarify when reference is made to the patient's physical pelvis 12 or a three dimensional bone model 512, which is a representation of the patient pelvis 12 provided as a three dimensional image, respectively.

Figure 8A:
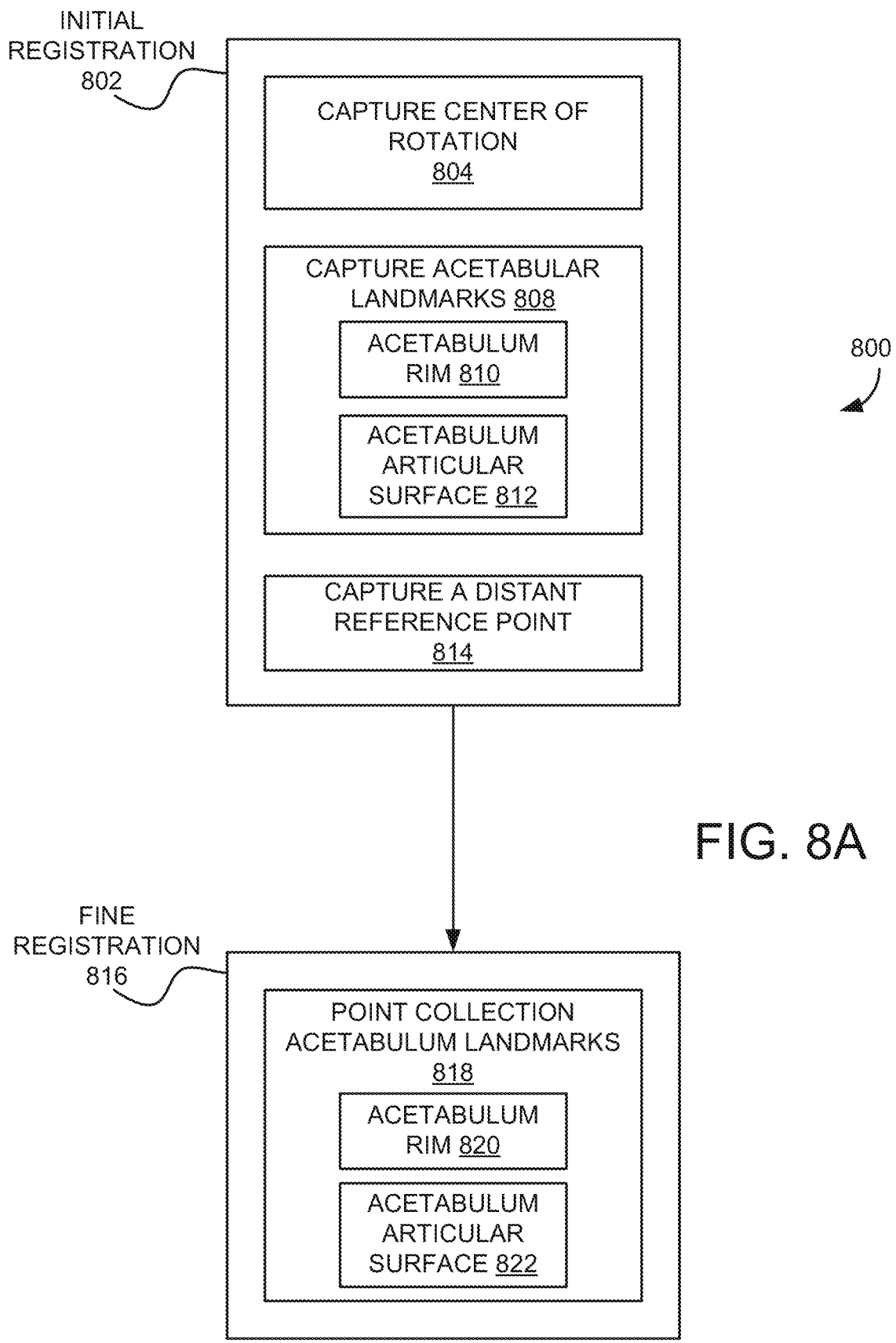
FIG. 8A illustrates an embodiment of steps of a pelvic registration method.

Reference is made to FIG. 8A, which shows a flowchart of the pelvic registration method 800. The method 800 may include an initial registration 802 to provide an initial mapping of the patient pelvis 12 (physical space) with the three dimensional model 512 (image space) with respect to position and orientation. The method 800 may also include a fine registration 816 for fine tuning of the position and orientation.

i. Initial Registration

As seen in FIG. 8A, the initial registration 802 includes a step of capturing the center of rotation 804, capturing acetabular landmarks 808, and capturing a distant reference point 814. Capturing the acetabular landmarks 808 may include a step of capturing points on the acetabular rim 810, and a step of capturing points on the surface of the acetabulum 812.

In discussing each step in the registration method 800, reference will be made to FIG. 8B, which is a chart depicting the steps of the initial and fine registration 802, 816, along with an overview of characteristics associated with each step. The Landmark/Region column indicates the portion of the pelvis that is at issue in each step of the method 800. The Capture Method column indicates whether the method of capturing points or data is a point-based collection method or a region-based collection method. The difference between the two methods will be discussed subsequently. The Used By column indicates whether the particular step of the method 800 may be used in initial or fine registration 802, 816. The Approach Dependent column indicates whether or not the system 5 will vary the procedure based on the particular surgical approach. For example, step 810 indicates that capturing points on the acetabular rim is approach dependent. Thus, the system 5 may indicate points for capturing during initial registration that are specific for the chosen surgical approach (e.g., direct anterior, antero-lateral, postero-lateral). In a direct anterior approach, for instance, the system 5 may identify points for capturing on the anterior acetabular rim since this particular area of the acetabulum is more accessible than others, such as the posterior acetabular rim.

Lastly, the Captured In column indicates where and when the points are captured. Each row indicates "Pre-Op/Intra-Op Registration". While all steps of the method 800 occur during intra-operative registration on the patient pelvis (physical space), the points captured during the intra-operative registration must be compared with pre-operatively identified landmarks that correspond with the intra-operatively captured points in order to orient or register the patient pelvis 12 (physical space) with the three dimensional bone model 512 of the patient pelvis 12 (image space). Thus, each of the landmarks in the Landmark/Region column are identified in the three dimensional bone model 512 which is generated based on pre-operatively images (e.g., CT, MRI) of the patient pelvis 12. These locations of pre-operative landmarks, relative to each other, are compared with the locations of the intra-operatively registered points to determine the accuracy of the registration process.

Figure 9A:
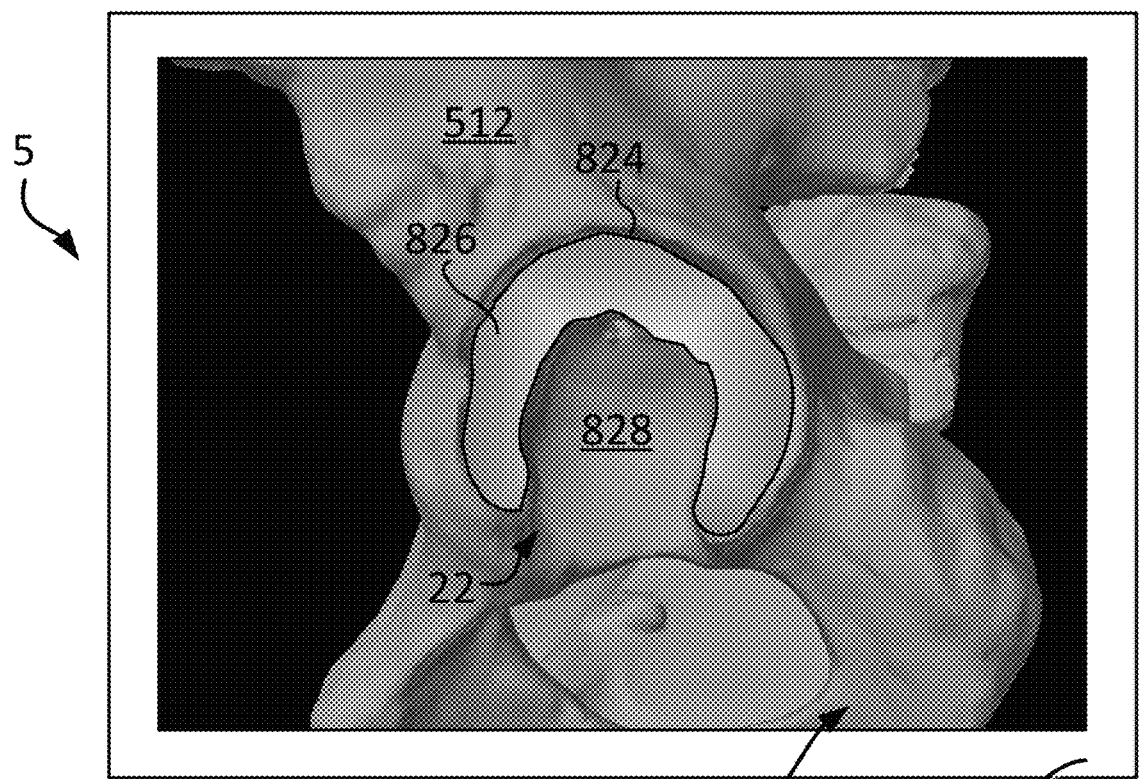
FIG. 9A is a lateral view of a three dimensional bone model of the patient pelvis showing a highlighted band along the articular surface of the acetabulum.

The discussion will now focus on the steps of the initial registration 802 and, in particular, the step of registering the center of rotation 804. For this, reference is made to FIGS. 9A-9B, which depict, respectively, a lateral view of the three dimensional model 512 of the pelvis 12 and a lateral view of the pelvis 12 (physical space). As seen in FIG. 9A, the three dimensional model 512 of the pelvis 12, as viewed on a display screen 9, includes a highlighted band 824 on the articular or lunate surface 826 of the acetabulum 22. The articular surface 826 is crescent-shaped and is typically covered by articular cartilage, which is not shown in the three dimensional model 512. The non-articular area of the acetabulum 22 is the acetabular fossa 828. The articular surface 826 of the acetabulum 22 is hemispherical in shape and abuts the femoral head (not shown) and allows it to rotate within the acetabulum 22.

Figure 9B:
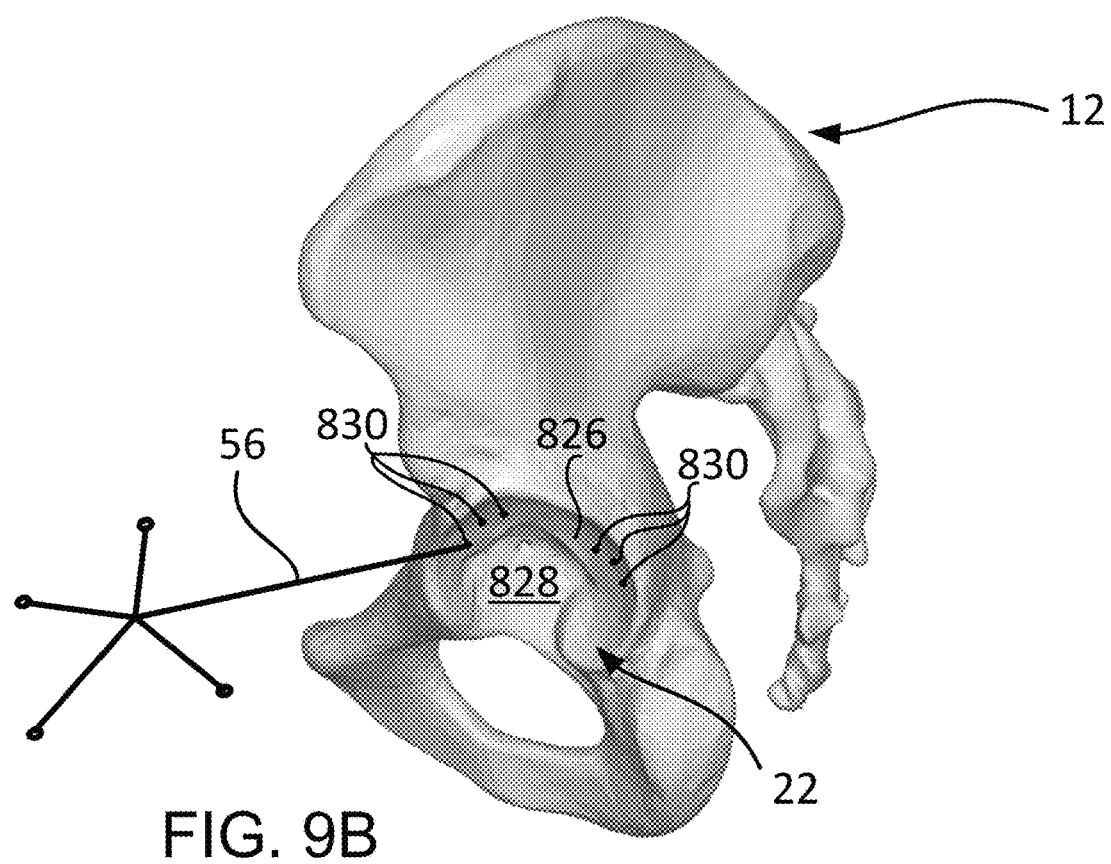
FIG. 9B is a lateral view of the patient pelvis intra-operatively with a distal tip of a navigational probe contacting a point on the articular surface of the acetabulum.

To register the center of rotation 804, as seen in FIG. 8, a surgeon may use the navigational probe 56 to capture, collect, or record data points (referred to as patient data) on the patient pelvis 12 (physical space), as seen in FIG. 9B, at multiple points along the articular surface 826 of the acetabulum 22 that corresponds to the highlighted band 824 on the three dimensional model 512 of the pelvis 12. An alternative embodiment could use a navigational probe 56 or the tracked femur 14 that allows a surgeon to rotate within the acetabulum 22 thereby establishing a dataset representing the center of rotation 804. Capturing, collecting, or recording data points means that the system 5 (e.g., computer 15) stores the location of the points relative to each other in a common coordinate system. An algorithm is then used to integrate the captured points into the coordinate system of the three dimensional bone model 512 to register or align the patient pelvis 12 (physical space) with the model 512. In this way and upon completion of registration, a representation of the distal end a surgical tool 58 of the robotic arm 30 of the surgical system 5 may be displayed on the display 9 relative to the three dimensional bone model 512 in a way that appropriately corresponds with the physical location and orientation of the distal end of the surgical tool 58 with respect to the actual patient pelvis 12 (physical space).

Capturing data points or patient data within the highlighted band 824 may be referred to as a region-based point collection as opposed to a point-based collection because acceptable points may be captured throughout the articular surface 826 corresponding to the highlighted band 824. In a point-based collection system, a specific point may be depicted on the three dimensional model 512 of the pelvis 12 and the surgeon may be queried to capture a data point at the specific point on the patient pelvis 12 (physical space) that corresponds to the specific point on the three dimensional model 512.

In a certain embodiment, the system 5 may require the distance between any two points 830 to be spaced apart from each other a certain amount. The system 5 may require the distance between any two points 830 to be greater than 5 mm. The system 5 may require the distance between any two points 830 to be less than 80 mm. The system 5 may have an algorithm that defines a required distance between any two points 830 based on other inputs (e.g. acetabulum 22 or acetabular component 28). The system 5 may vary the distance between any two points 830 during point capture. Such a requirement may facilitate the dispersion of captured points 830 so that all points 830 are not captured in one region of the articular surface 826, for example. In certain embodiments, the system 5 may not require a defined distance spacing between points 830. In certain embodiments, the collected point 830 that is not satisfied the minimum spacing distance requirement may be rejected as an outlier or still be used for the point-to-model surface matching in fine registration 816.

In a certain embodiment, the system 5 may require a maximum and/or a minimum number of points 830 to be collected on the articular surface 826. The system 5 may require at least ten points 830 be captured. Additionally or alternatively, the system 5 may require less than twenty points 830 be captured.

Figure 9C:
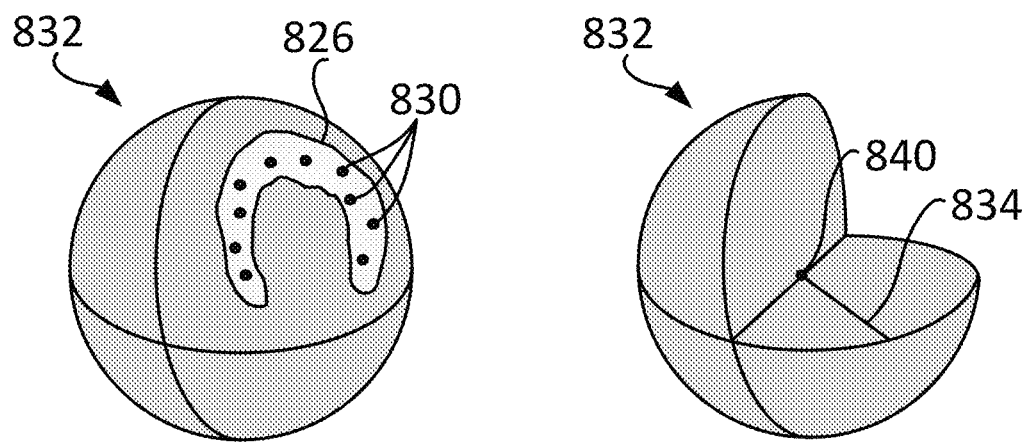
FIG. 9C depicts, on the left, a sphere generated by captured points on the articular surface of the acetabulum, and, on the right, a ¾ segment of the sphere in order to show the radius of the sphere.

Referring to FIG. 9C, the system 5 can use the captured points 830 on the highlighted band 824 to define a sphere 832 with a center point 840 and a radius 834 since the articular surface 826 of the acetabulum 22 is spherical. Stated differently, the system 5 can generate a sphere 832 using the location of the captured points 830 because their locations relative to each other along with a best-fit calculation of the points 830 can be fitted to a sphere 832. From the size of the sphere 832, the radius 834 (or diameter, volume, etc.) can be determined.

It is noted that the sphere 832 on the left in FIG. 9C illustrates the highlighted band 824 and the points 830 on a spherical surface of the sphere 832. The sphere 832 on the right illustrates a ¾ segment of the sphere 832 in order to depict the radius 834.

In a certain embodiment, the system 5 may optimize the number of points 830 by stopping point 830 collection when points 830 are more than the minimum number of points 830 but less than the maximum number of points 830. The system 5 may use an algorithm such as convergence metrics to determine the stopping criterion/criteria. In a certain embodiment, a convergence metric can be the difference between the radius 834 calculated using N collected points 830 and the radius 834 calculated using a subset of collected points 830, such as N−1 collected points 830. If the difference between the two radii 834 is smaller than a predefined threshold, the system 5 ends the point 830 collection early before the points 830 reach the maximum number of points 830. In a certain embodiment, the convergence metrics can be calculated every time when a new point 830 is collected.

Figure 9D:
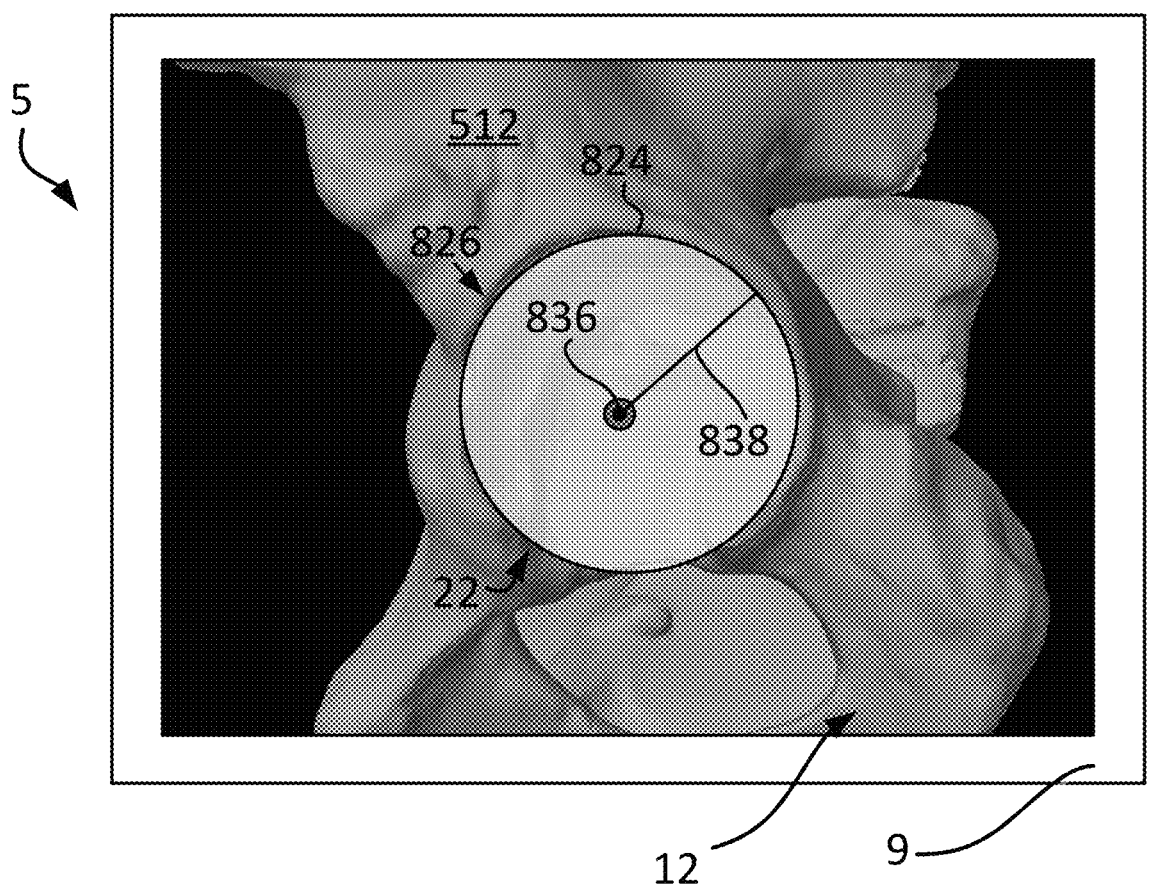
FIG. 9D depicts a later view of the three dimensional bone model with a point of center of rotation determined pre-operatively from medical imaging of the patient pelvis.

As seen in FIG. 9D, a center of rotation point 836 may be pre-operatively determined based on the three dimensional bone model 512 of the pelvis 12. A radius 838 may then be determined from the center of rotation point 836 to the articular surface 826 of the acetabulum. The center of rotation point 836 may be determined based on pre-operative scans of the patient pelvis 12 and femoral head 16.

The size of the sphere 832 or, more particular, the radius 834 of the sphere 832 as determined from the intra-operative capturing of the points 830, or patient data (physical space), as in FIG. 9C, may be compared with the radius 838 from the center of rotation point 836 as determined from the three-dimensional bone model 512 (image space), as seen in FIG. 9D. That is, the intra-operatively collected patient data (e.g., sphere 832 and radius 834 in FIG. 9C) may be compared with the pre-operatively determined values (e.g., radius 838 of FIG. 9D) to determine the variation there between.

More particularly, the system 5 may require a certain minimum difference between the two radii 834, 838 before the user of the system 5 may continue beyond step 804 of the initial registration 802. In certain embodiments, the system 5 may require the radii 834, 838 to be less than 5 mm different from each other. In certain embodiments, the system 5 may require the radii 834, 838 to be less than 4 mm different from each other. In certain embodiments, the system 5 may require the radii 834, 838 to be less than 3 mm different from each other. In certain embodiments, the system 5 may require the radii 834, 838 to be less than 2 mm different from each other. In certain embodiments, the system 5 may require the radii 834, 838 to be less than 1 mm different from each other.

If the difference between the radii 834, 838 is within allowable tolerances, the system 5 (e.g., computer 15) may merge the location of the center point 840 of the sphere 832 as determined from the intra-operative capturing of the points 830 with the center of rotation point 836 as determined from the three dimensional bone model 512. In this way, the translational orientation or aspect of registering the patient pelvis 12 (physical space) with the three dimensional bone model 512 of the pelvis 12 (image space) into a common coordinate system is fixed or locked into place. Stated differently, three degrees of freedom (i.e., translation in x, y, and z directions) may be fixed or preliminarily determined upon merging the center point 840 of the sphere 832 with the center of rotation point 836; thus, three degrees of freedom (i.e., rotation about the x, y, and z directions) are yet unknown.

In general, the system 5 is able to simplify the anatomy based on the CT scans to a patient specific geometrical feature. And then it generates a similar geometry based on the patient data from the captured points. The CT-based patient specific geometric feature is then compared with the intra-operatively captured geometric feature. The result of the comparison reflects the quality of points capturing and bone registration.

The subsequent steps of the registration process determine the rotational orientation of the patient pelvis 12 (physical space) with respect to the three dimensional bone model 512 of the pelvis (image space) such the robotic arm 30 of the system 5 will be oriented similarly in the image space and the physical space with respect to the bone model 512 of the pelvis and the patient pelvis, respectively.

Once the center of rotation 804 is calculated or captured, various other points of patient data such as acetabular landmarks may be captured 808, as shown in FIG. 8. As stated previously, the capturing of the acetabular landmarks 808 may be used to determine the rotational orientation of the pelvis 12 (physical space) with the three dimensional bone model 512 of the pelvis 12 (image space). And since the translational relationship between the physical space and the image space is known by being fixed at the center of rotation point 836, the various acetabular landmarks captured at step 808 may be used to check the distances between the landmarks and the center of rotation point 836.

Capturing patient data as points on the acetabular landmarks at step 808 are point-based and may be approach dependent. As described previously, point-based data capture means that a point is identified (e.g., highlighted with a dot) on the three dimensional bone model 512 of the pelvis 12 (image space) and the surgeon is queried to select the corresponding point on the patient pelvis (physical space) with the navigational probe 56. The system 5 (e.g., computer 15) can then compare the distances between, for example, the center of rotation point 836 and the highlighted point on the three dimensional bone model 512, and the center 840 of the sphere 832 and the intra-operatively captured point.

To begin the discussion of capturing acetabular landmarks at step 808, first is a description of antero-lateral and direct anterior approaches for capturing points on the acetabulum rim and articular surface at steps 810 and 812, at FIGS. 10A-10D. Second, is a description of postero-lateral approaches for capturing points on the acetabulum rim and articular surfaces at steps 810 and 812, illustrated in FIGS. 10E-10H. Though not described, the methods herein may be applied to other hip surgical approaches (e.g. direct superior) or to the capture of landmarks for registering other joints (e.g. shoulder, elbow, knee, ankle), as shown in FIGS. 15A-15D.

Figure 10A:
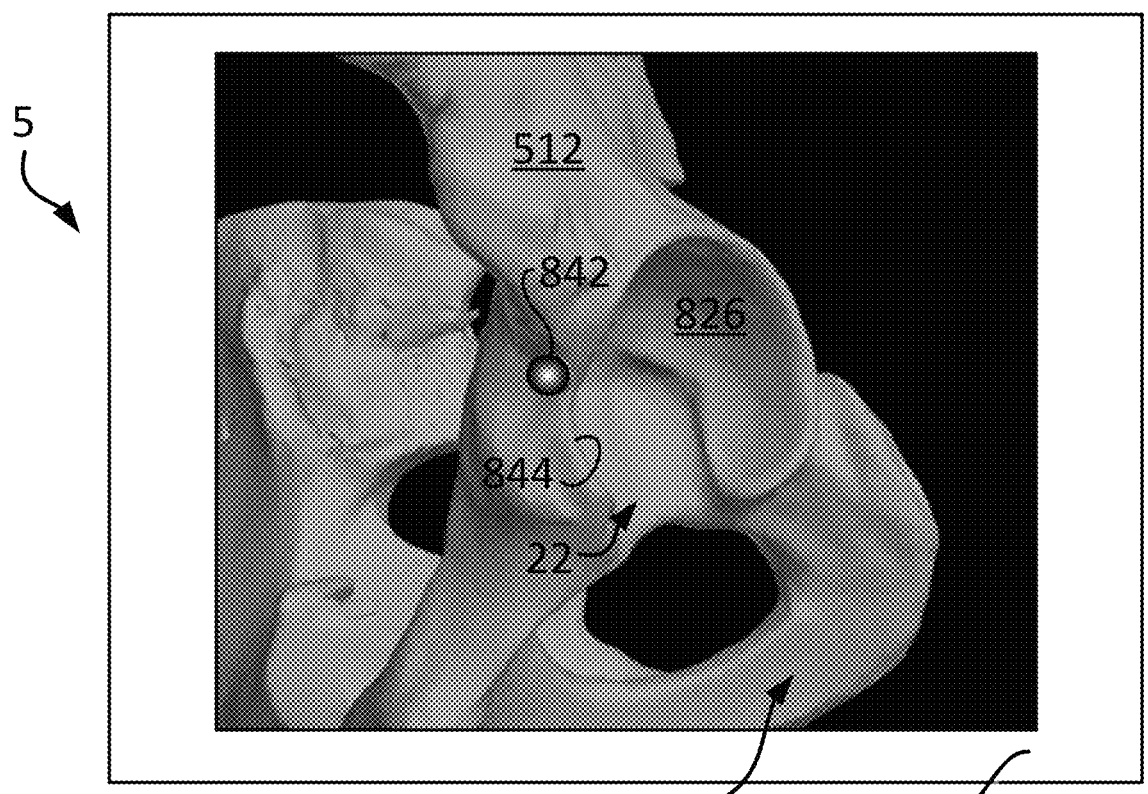
FIG. 10A is an antero-lateral view of the three dimensional bone model with a point highlighted on the anterior acetabular rim.
Figure 10B:
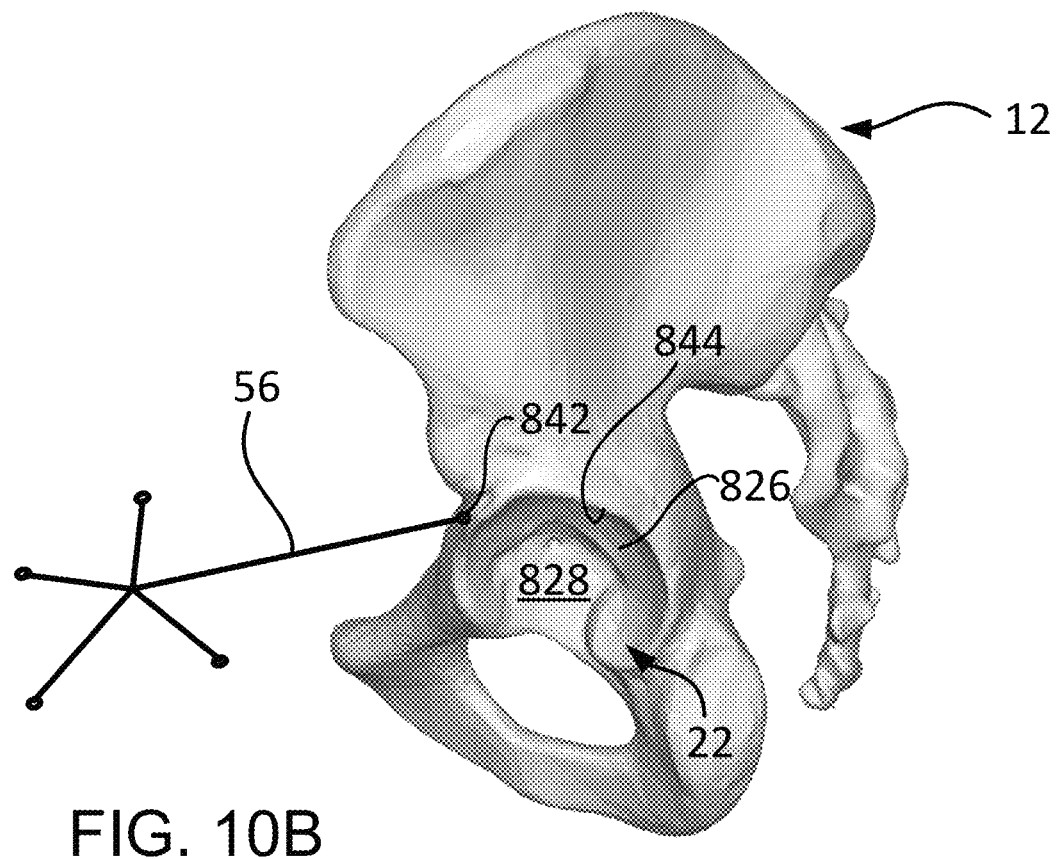
FIG. 10B is a lateral view of the patient pelvis intra-operatively with a distal tip of a navigational probe contacting a point on the anterior acetabular rim.

Reference is made to FIGS. 10A and 10B, which are, respectively, an antero-lateral view of the three dimensional bone model 512 of the patient pelvis 12 (image space) and a lateral view of the patient pelvis 12 (physical space). As seen in FIG. 10A, the system 5 may identify (e.g., highlight) one or more points 842 on the anterior aspect of the acetabular rim 844 that forms the outer edge of the acetabulum 22 on the three dimensional bone model 512 of the patient pelvis (image space). The system 5 may then query the surgeon, as seen in FIG. 10B, to capture the corresponding point(s) 842 on the patient pelvis 12 (physical space) by touching the distal end of the navigational probe 56 against the point 842 and logging, collecting, or capturing the position of the point 842 as patient data within the system 5. As seen in FIG. 10B, the point 842 on the anterior aspect of the acetabular rim 844 is accessible by the surgeon from a direct anterior approach or an antero-lateral approach.

For each point 842 identified by the system 5 and captured by the surgeon, the system 5 may then compare the distance between the identified point 842 and the center of rotation point 836 (image space), as seen in FIGS. 9D and 10A, with the intra-operatively gathered distance between the captured point 842 and the center point 840 of the sphere 832, of FIGS. 9C and 10B.

In certain embodiments, the system 5 may identify and query the surgeon to capture a single point 842 on the anterior aspect of the acetabular rim 844. In certain embodiments, the system 5 may identify and query the surgeon to capture two points 842 on the anterior aspect of the acetabular rim 844. In certain embodiments, the system 5 may identify and query the surgeon to capture five points 842 on the anterior aspect of the acetabular rim 844. In certain embodiments, the system 5 may identify and query the surgeon to capture ten points 842 on the anterior aspect of the acetabular rim 844. In certain embodiments, the system 5 may identify and query the surgeon to capture fifteen points 842 on the anterior aspect of the acetabular rim 844. In certain embodiments, the system 5 may identify and query the surgeon to capture another number of points 842 on the anterior aspect of the acetabular rim 844.

In certain embodiments, the system 5 may display one point 842 at a time on the three dimensional bone model 512 and require the surgeon to capture the corresponding point 842 on the patient pelvis 12 (physical space) before the system 5 displays another point 842 on the three dimensional bone model 512. In other embodiments, the system 5 may display all points 842 (e.g., 1, 2, 5, 10, 15) on the three dimensional bone model 512 of the pelvis and allow the surgeon to capture the corresponding points in any order he or she chooses.

Figure 10C:
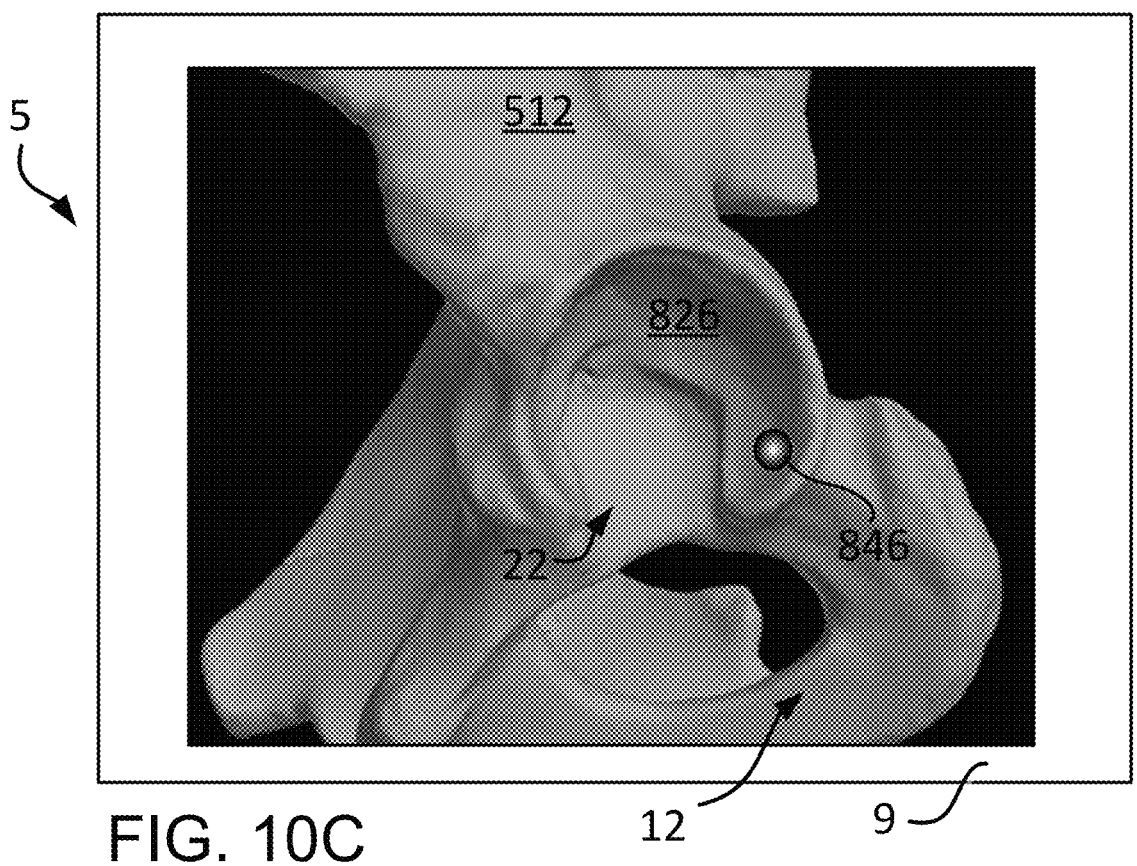
FIG. 10C is an antero-lateral view of the three dimensional bone model with a point highlighted on the posterior articular surface of the acetabulum.
Figure 10D:
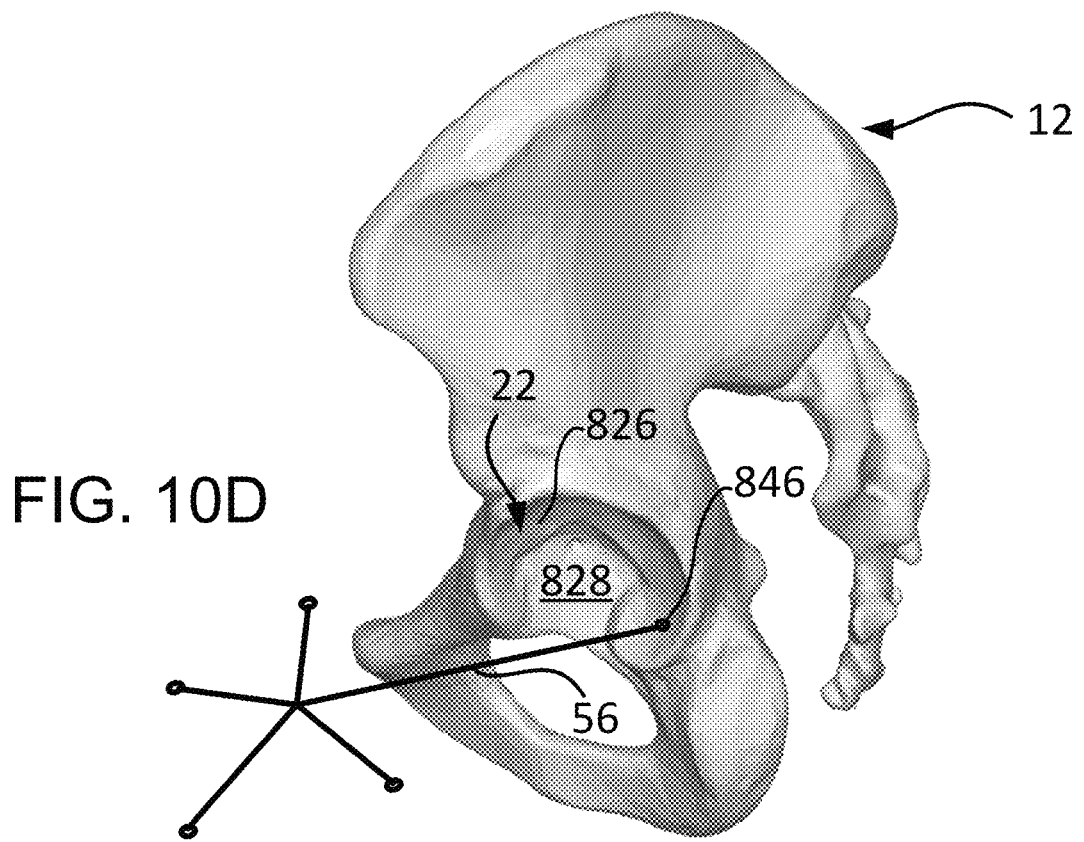
FIG. 10D is a lateral view of the patient pelvis intra-operatively with a distal tip of a navigational probe contacting a point on the posterior articular surface of the acetabulum.

Continuing on with capturing the acetabular landmarks, the surgeon may also capture one or more points on the acetabular articular surface, at step 812 of FIG. 8. As seen in FIG. 10C, which is an antero-lateral view of the three dimensional bone model 512 of the patient pelvis 12 (image space), one or more points 846 may be identified (e.g., highlighted) on a posterior aspect of the articular surface 826 of the acetabulum 22 of the three dimensional bone model 512 of the patient pelvis (image space). The system 5 may query the surgeon, as seen in FIG. 10D, which is a lateral view of the patient pelvis 12 (physical space), to capture the corresponding point(s) 846 on the posterior aspect of the patient pelvis 12 (physical space) by touching the distal end of the navigational probe 56 against the point(s) 846 and logging, collecting, or capturing the position of the point(s) 846 as patient data within the system 5. As seen in FIG. 10D, the point 846 on the posterior aspect of the acetabulum 22 is accessible by the surgeon from a direct anterior approach or an antero-lateral approach.

For each point 846 identified by the system 5 and captured by the surgeon, the system 5 may then compare the distance between the identified point 846 and the center of rotation point 836 (image space), as seen in FIGS. 9D and 10C, with the intra-operatively gathered distance between the captured point 846 and the center point 840 of the sphere 832, of FIGS. 9C and 10D.

In certain embodiments, the system 5 may identify and query the surgeon to capture a single point 846 on the posterior aspect of the acetabulum 22. In certain embodiments, the system 5 may identify and query the surgeon to capture two points 846 on the posterior aspect of the acetabulum 22. In certain embodiments, the system 5 may identify and query the surgeon to capture five points 846 on the posterior aspect of the acetabulum 22. In certain embodiments, the system 5 may identify and query the surgeon to capture ten points 846 on the posterior aspect of the acetabulum 22. In certain embodiments, the system 5 may identify and query the surgeon to capture fifteen points 846 on the posterior aspect of the acetabulum 22. In certain embodiments, the system 5 may identify and query the surgeon to capture another number of points 846 on the posterior aspect of the acetabulum 22.

In certain embodiments, the system 5 may display one point 846 at a time on the three dimensional bone model 512 and require the surgeon to capture the corresponding point 846 on the patient pelvis 12 (physical space) before the system 5 displays another point 846 on the three dimensional bone model 512. In other embodiments, the system 5 may display all points 846 (e.g., 1, 2, 5, 10, 15) on the three dimensional bone model 512 of the pelvis and allow the surgeon to capture the corresponding points in any order he or she chooses.

Figure 10E:
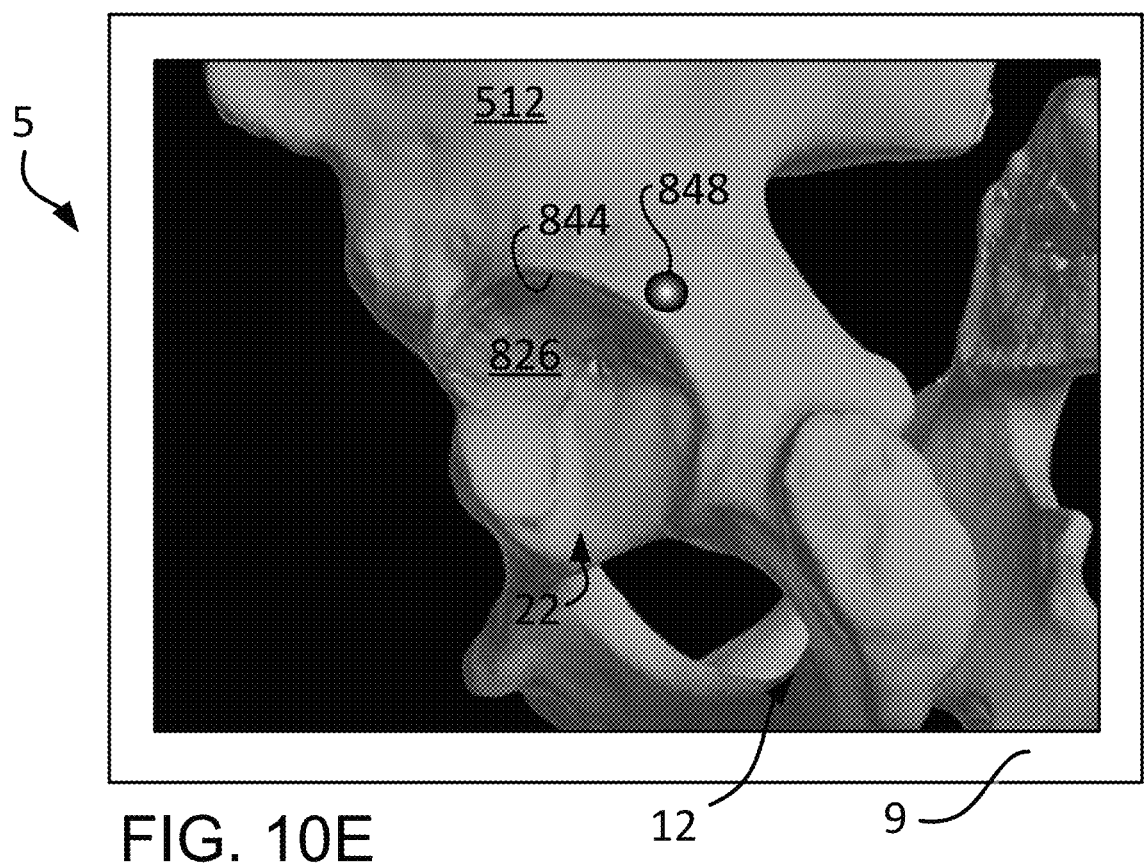
FIG. 10E is a postero-lateral view of the three dimensional bone model with a point highlighted on the posterior acetabular rim.
Figure 10F:
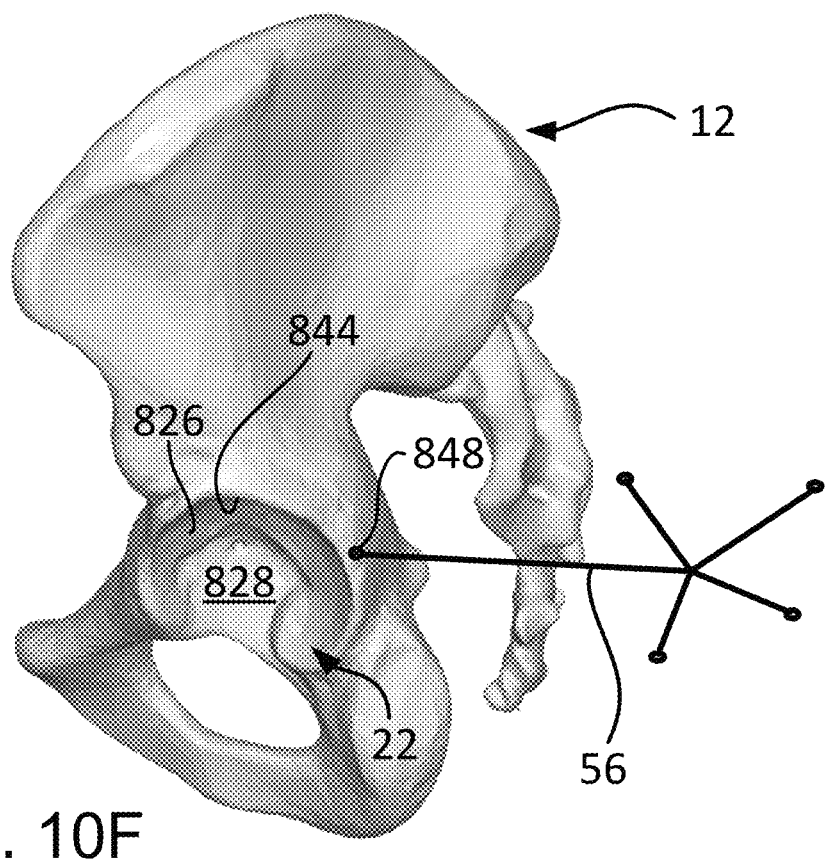
FIG. 10F is a lateral view of the patient pelvis intra-operatively with a distal tip of a navigational probe contacting a point on the posterior acetabular rim.

The following is a discussion of postero-lateral approaches for capturing points on the acetabulum rim and articular surfaces at steps 810 and 812. Reference is made to FIGS. 10E-10F for capturing points on the acetabular rim 844 and to FIGS. 10G-10H for capturing points on the articular surface 826 of the acetabulum 22.

As seen in FIG. 10E, which is a postero-lateral view of the three dimensional bone model 512 of the pelvis 12 (image space) displayed on a display screen 9, one or more points 848 may be identified (e.g., highlighted) on a posterior aspect of the acetabular rim 844 of the acetabulum 22 of the three dimensional bone model 512 of the patient pelvis (image space). The system 5 may query the surgeon, as seen in FIG. 10F, which is a lateral view of the patient pelvis 12 (physical space), to capture the corresponding point(s) 848 on the posterior aspect of the acetabular rim 844 of the patient pelvis 12 (physical space) by touching the distal end of the navigational probe 56 against the point(s) 848 and logging, collecting, or capturing the position of the point(s) 848 as patient data within the system 5. As seen in FIG. 10F, the point 848 on the posterior aspect of the acetabulum rim 844 is accessible by the surgeon from a postero-lateral approach.

For each point 848 identified by the system 5 and captured by the surgeon, the system 5 may then compare the distance between the identified point 848 and the center of rotation point 836 (image space), as seen in FIGS. 9D and 10E, with the intra-operatively gathered distance between the captured point 848 and the center point 840 of the sphere 832, of FIGS. 9C and 10F.

In certain embodiments, the system 5 may identify and query the surgeon to capture a single point 848 on a posterior aspect of the acetabular rim 844. In certain embodiments, the system 5 may identify and query the surgeon to capture two points 848 on a posterior aspect of the acetabular rim 844. In certain embodiments, the system 5 may identify and query the surgeon to capture five points 848 on a posterior aspect of the acetabular rim 844. In certain embodiments, the system 5 may identify and query the surgeon to capture ten points 848 on a posterior aspect of the acetabular rim 844. In certain embodiments, the system 5 may identify and query the surgeon to capture fifteen points 848 on a posterior aspect of the acetabular rim 844. In certain embodiments, the system 5 may identify and query the surgeon to capture another number of points 848 on a posterior aspect of the acetabular rim 844.

In certain embodiments, the system 5 may display one point 848 at a time on the three dimensional bone model 512 and require the surgeon to capture the corresponding point 848 on the patient pelvis 12 (physical space) before the system 5 displays another point 848 on the three dimensional bone model 512. In other embodiments, the system 5 may display all points 848 (e.g., 1, 2, 5, 10, 15) on the three dimensional bone model 512 of the pelvis and allow the surgeon to capture the corresponding points in any order he or she chooses.

Figure 10G:
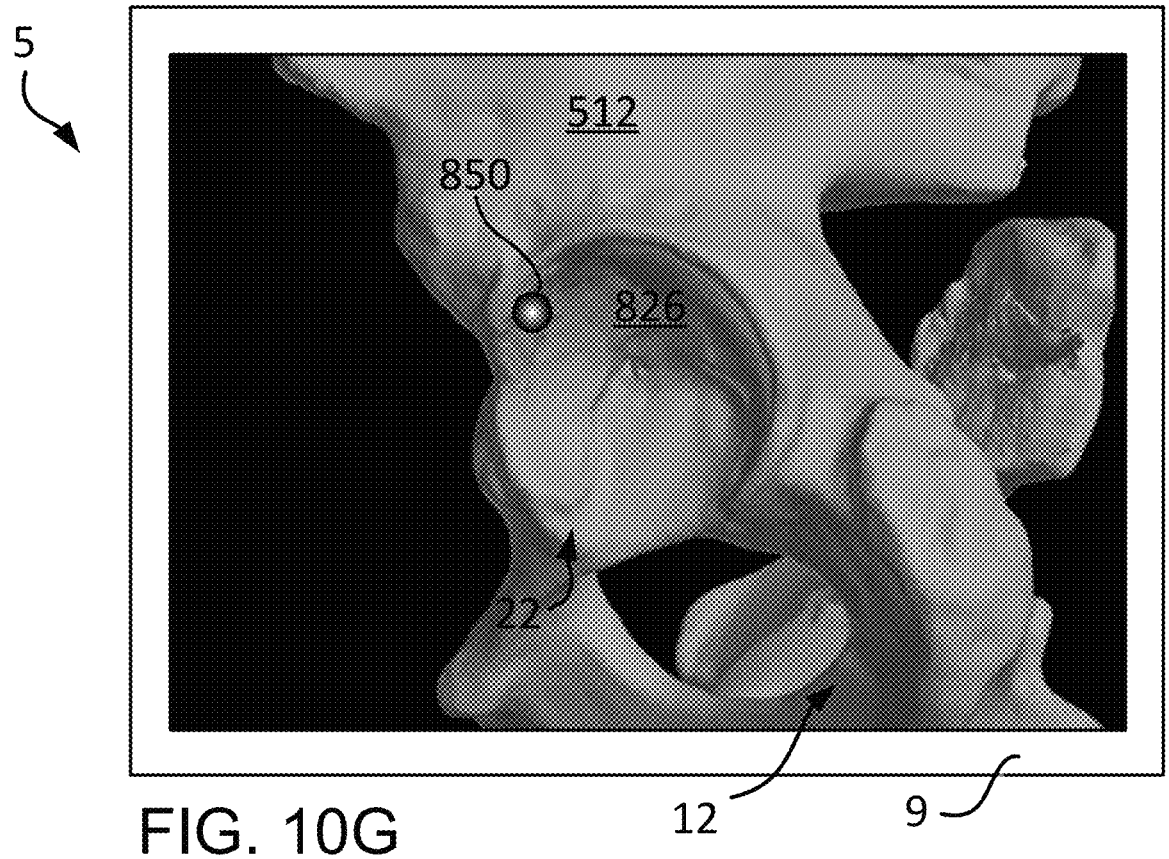
FIG. 10G is a postero-lateral view of the three dimensional bone model with a point highlighted on the anterior articular surface of the acetabulum.
Figure 10H:
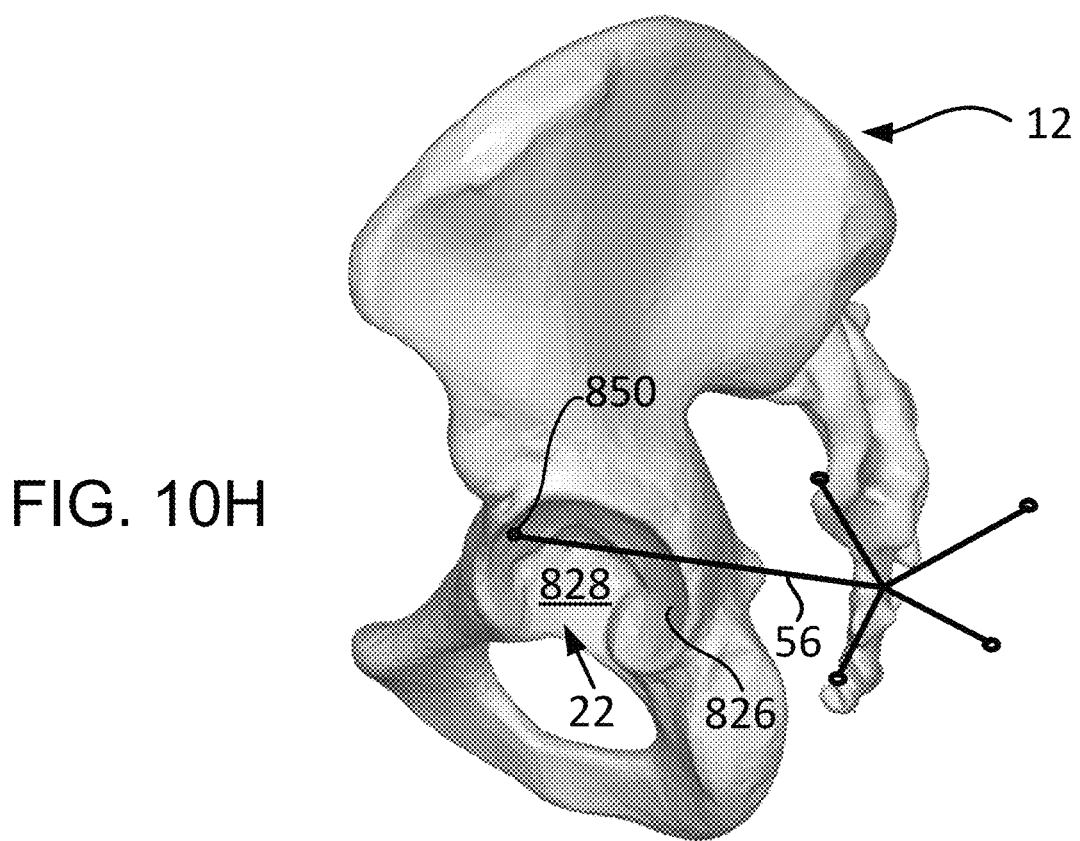
FIG. 10H is a lateral view of the patient pelvis intra-operatively with a distal tip of a navigational probe contacting a point on the anterior articular surface of the acetabulum.

Now the discussion will focus on capturing anterior acetabular landmarks, at step 812 of FIG. 8. As seen in FIG. 10G, which is a postero-lateral view of the three dimensional bone model 512 of the pelvis 12 (image space) displayed on a display screen 9, one or more points 850 may be identified (e.g., highlighted) on an anterior aspect of the articular surface 826 of the acetabulum 22 of the three dimensional bone model 512 of the patient pelvis 12 (image space). The system 5 may query the surgeon, as seen in FIG. 10H, which is a lateral view of the patient pelvis 12 (physical space), to capture the corresponding point(s) 850 on the anterior aspect of the articular surface 826 of the acetabulum 22 of the patient pelvis 12 (physical space) by touching the distal end of the navigational probe 56 against the point(s) 850 and logging, collecting, or capturing the position of the point(s) 850 as patient data within the system 5. As seen in FIG. 10H, the point 850 on the anterior aspect of the articular surface 826 of the acetabulum 22 is accessible by the surgeon from a postero-lateral approach.

For each point 850 identified by the system 5 and captured by the surgeon, the system 5 may then compare the distance between the identified point 850 and the center of rotation point 836 (image space), as seen in FIGS. 9D and 10G, with the intra-operatively gathered distance between the captured point 850 and the center point 840 of the sphere 832, of FIGS. 9C and 10H.

In certain embodiments, the system 5 may identify and query the surgeon to capture a single point 850 on an anterior aspect of the articular surface 826. In certain embodiments, the system 5 may identify and query the surgeon to capture two points 850 on an anterior aspect of the articular surface 826. In certain embodiments, the system 5 may identify and query the surgeon to capture five points 850 on an anterior aspect of the articular surface 826. In certain embodiments, the system 5 may identify and query the surgeon to capture ten points 850 on an anterior aspect of the articular surface 826. In certain embodiments, the system 5 may identify and query the surgeon to capture fifteen points 850 on an anterior aspect of the articular surface 826. In certain embodiments, the system 5 may identify and query the surgeon to capture another number of points 850 on an anterior aspect of the articular surface 826.

In certain embodiments, the system 5 may display one point 850 at a time on the three dimensional bone model 512 and require the surgeon to capture the corresponding point 850 on the patient pelvis 12 (physical space) before the system 5 displays another point 850 on the three dimensional bone model 512. In other embodiments, the system 5 may display all points 850 (e.g., 1, 2, 5, 10, 15) on the three dimensional bone model 512 of the pelvis and allow the surgeon to capture the corresponding points in any order he or she chooses.

It is noted that the surgeon may select the type of surgical approach within the system 5 so that the steps of capturing acetabular landmarks, at step 808 in FIG. 8, are only displayed for the selected surgical approach. In this way, for a direct anterior or an antero-lateral surgical approach, as seen in FIGS. 10A-D, the system 5 may only display anterior acetabular rim 844 points 842 and posterior articular surface 826 points 846 on the acetabulum 22. Similarly, for a postero-lateral approach, as seen in FIGS. 10E-10H, the system 5 may only display posterior acetabular rim 844 points 848 and anterior articular surface 826 points 850 on the acetabulum 22.

Figure 11A:
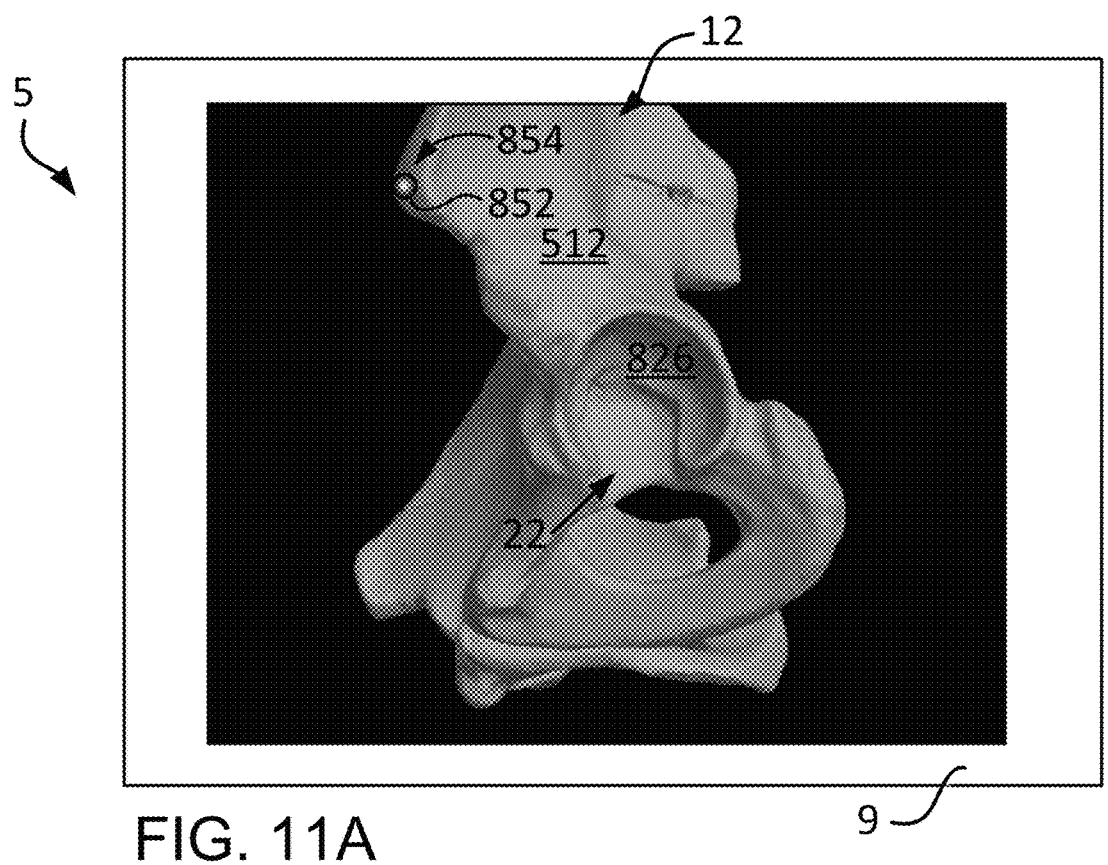
FIG. 11A is an antero-lateral view of the three dimensional bone model with a point highlighted on the anterior superior iliac spine.

The next step in the initial registration 802, according to FIG. 8, is to capture a distant reference point 814. For this step 814, reference is made to FIGS. 11A-11C. As seen in FIG. 11A, which is an antero-lateral view of the three dimensional bone model 512 of the patient pelvis 12 (image space) as displayed on a display screen 9, a point 852 may be identified (e.g., highlighted) on a distant reference point or marker such as the anterior superior iliac spine ("ASIS") 854. In certain embodiments, the distant reference point may be the iliac spine crest or other landmarks that are spaced apart from the acetabulum 22. In certain embodiments, the distant reference point may be another landmark within the incision. In certain embodiments, the distant reference point may be the ASIS on the non-operative side of the pelvis 12, or another landmark on the non-operative side of the patient.

Figure 11B:
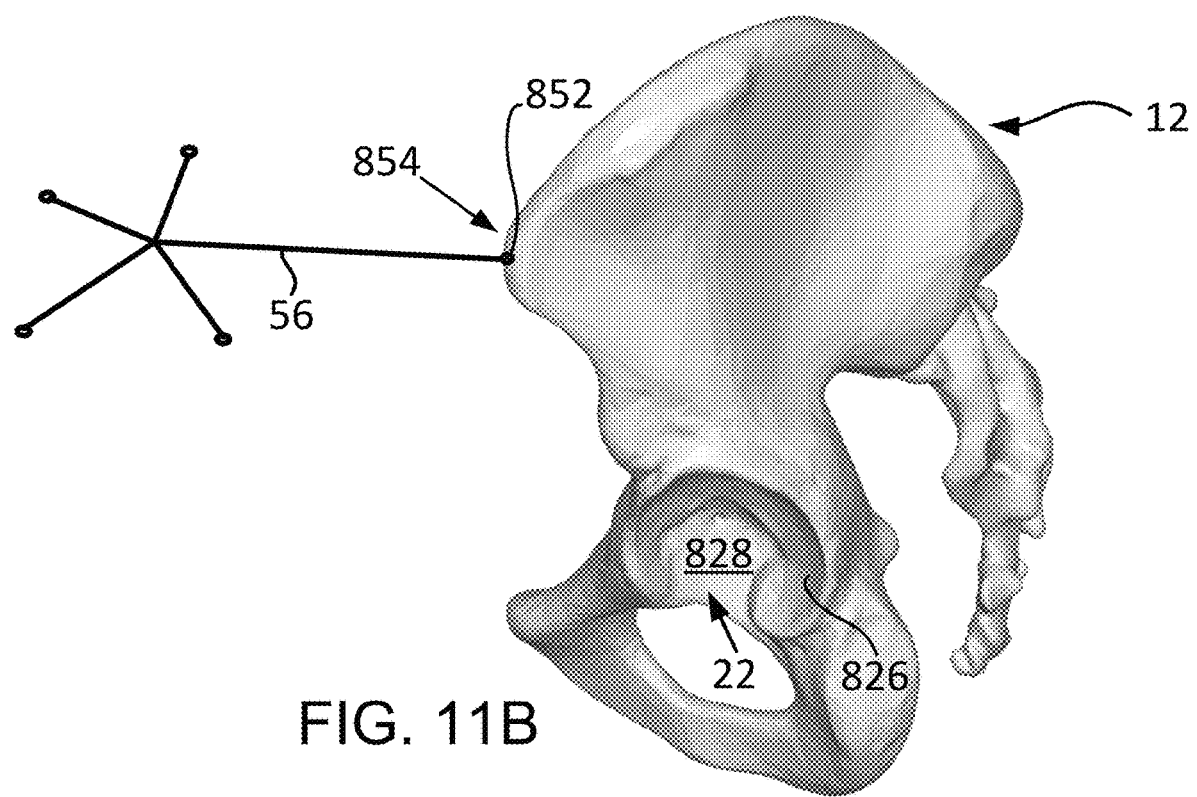
FIG. 11B is a lateral view of the patient pelvis intra-operatively with a distal tip of a navigational probe contacting a point on the ASIS.

As seen in FIG. 11B, which is a lateral view of the patient pelvis 12 (physical space), the system 5 may query the surgeon to capture the corresponding point 852 on the ASIS 854 of the patient pelvis 12 (physical space) by touching the distal end of the navigational probe 56 against the point(s) 852 and logging, collecting, or capturing the position of the point(s) 852 as patient data within the system 5. As seen in FIG. 11B, the point 852 on the ASIS 854 of the acetabulum 22 is accessible by the surgeon from a multitude of surgical approaches since the ASIS may be identified (e.g., palpated) without an incision into the patient body. In the case of the system 5 using the iliac spine crest, a bone pin incision may be made in order to capture the point 852 on the iliac spine crest.

In certain embodiments, the system 5 may identify and query the surgeon to capture a single point 852 (e.g., ASIS). In certain embodiments, the system 5 may identify and query the surgeon to capture two points 852 (e.g., ASIS, iliac spine crest). In certain embodiments, the system 5 may identify and query the surgeon to capture five points 852. In certain embodiments, the system 5 may identify and query the surgeon to capture ten points 852. In certain embodiments, the system 5 may identify and query the surgeon to capture fifteen points 852. In certain embodiments, the system 5 may identify and query the surgeon to capture another number of points 852.

In certain embodiments, the system 5 may display one point 852 at a time on the three dimensional bone model 512 and require the surgeon to capture the corresponding point 852 on the patient pelvis 12 (physical space) before the system 5 displays another point 850 on the three dimensional bone model 512. In other embodiments, the system 5 may display all points 852 (e.g., 1, 2, 5, 10, 15) on the three dimensional bone model 512 of the pelvis and allow the surgeon to capture the corresponding points in any order he or she chooses.

For each point 852 identified by the system 5 and captured by the surgeon, the system 5 may then compare the distance between the identified point 852 and the center of rotation point 836 (image space), as seen in FIG. 9D AND 11A, with the intra-operatively gathered distance between the captured point 852 and the center point 840 of the sphere 832, of FIGS. 9C and 11B.

Figure 11C:
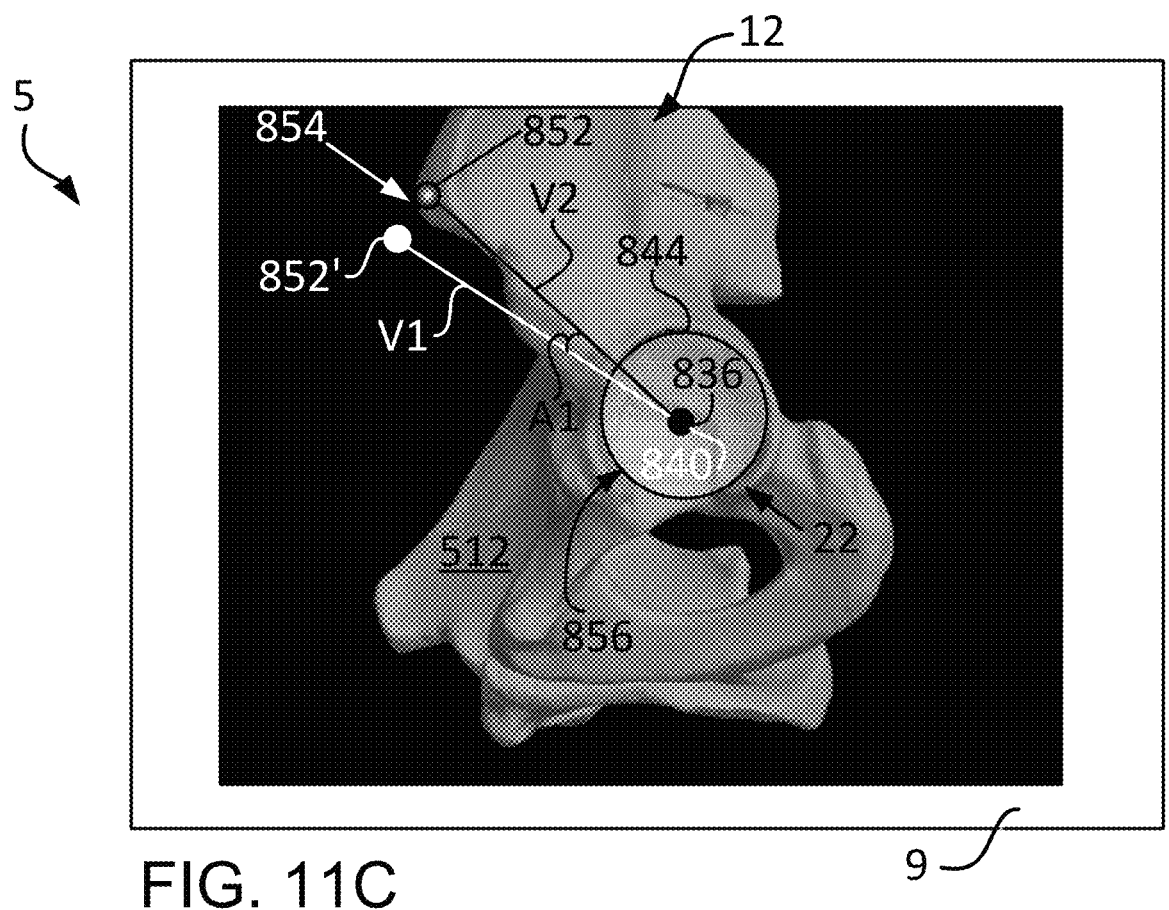
FIG. 11C is a lateral view of the three dimensional bone model depicting a pair of vectors in order to measure angular orientation relative to an acetabular plane.

As seen in FIG. 11C, which is an antero-lateral view of the three dimensional bone model 512 of the patient pelvis 12 (image space) as displayed on a display screen 9, an intra-operatively determined vector V1 is compared with a pre-operatively determined vector V2. The intra-operatively determined vector V1 may extend from the center point 840, which is coextensive with the center of rotation point 836, to the intra-operatively captured point 852', which corresponds to the ASIS 854 of the patient pelvis (physical space). The pre-operatively determined vector V2 may extend from the center of rotation point 836 to the point 852 on the ASIS 854 as determined from the pre-operative image scans (e.g., CT, MRI) of the pelvis 12 (image space).

The vectors V1, V2 may extend from an acetabular plane 856 which is coextensive with the acetabular rim 844. From this plane 856, a normal line centered at the center of rotation 836 may be identified. The angular difference A1 between the vectors V1, V2 may be used to lock the rotational alignment or orientation of the intra-operatively captured points (physical space) with the three dimensional bone model 512 (image space).

The system 5 may use the corresponding pre-operatively captured landmark points (image space), stored as patient data, as reference and give guidance to the user for capturing the intra-operatively captured landmark points (physical space). In certain embodiments, the system 5 may provide guidance based on the three dimensional geometry of pre-operatively captured landmark points (image space), and expect the same three dimensional geometry for the corresponding intra-operatively captured landmark points (physical space). In certain embodiments, the system 5 may use the Euclidean distance of landmark points to provide guidance. In certain embodiments, the system 5 may use the three dimensional angle between the vectors calculated from the landmark points to provide guidance. In certain embodiments, the system 5 may use the paired-point registration algorithm to best fit the pre-operatively captured landmark points (image space) and the corresponding intra-operatively captured landmark points (physical space), and use a fitting error to provide guidance. The guidance may be visual, audio, or tactile feedback or a combination of each.

Upon the completion of intra-operatively captured landmark points, the system 5 may use an algorithm to calculate the initial registration 802 transform using the intra-operatively captured landmark points (physical space) and the corresponding pre-operatively captured landmark points (image space). In certain embodiments, the system 5 may use a paired-point registration algorithm to compute the initial registration 802 transform. In certain embodiments, the system 5 may use intra-operatively captured landmark points 836, 842, 846, 848, 850, 852 (physical space), stored as patient data, and the corresponding pre-operatively captured landmark points (image space) to compute the initial registration 802 transform. In certain embodiments, the system 5 may only use a subset of the intra-operatively captured landmark points and the corresponding pre-operatively captured landmark points to find the best initial registration 802 transform.

ii. Fine Registration

Figure 12A:
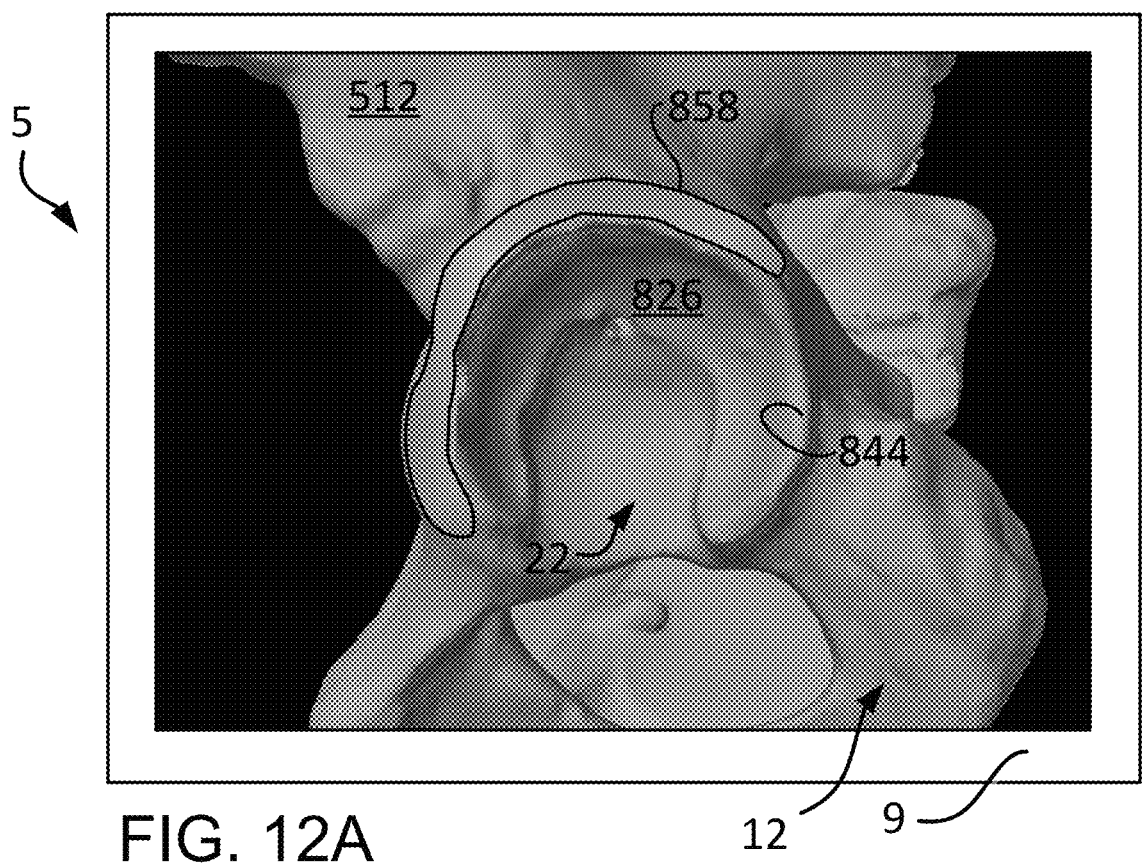
FIG. 12A is lateral view of the three dimensional bone model of the patient pelvis with a highlighted band on the anterior and superior aspect of the acetabular rim.
Figure 12B:
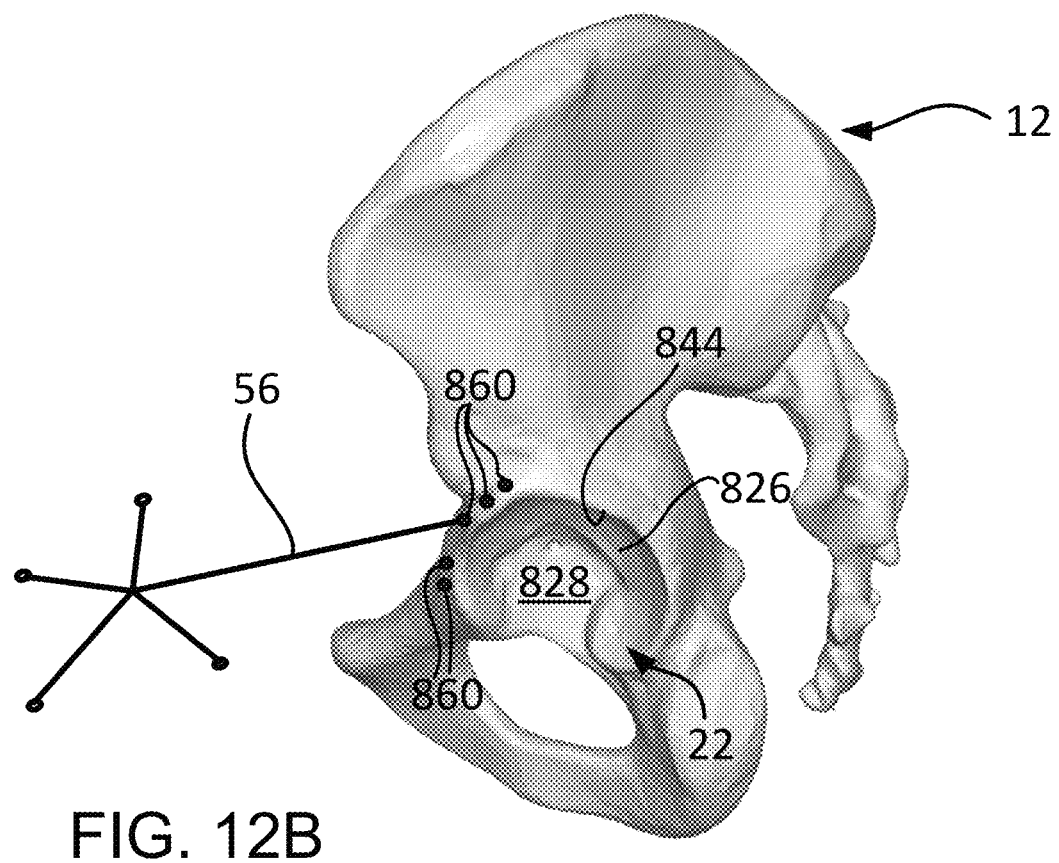
FIG. 12B is a lateral view of the patient pelvis intra-operatively with a distal tip of a navigational probe contacting a point on the anterior aspect of the acetabular rim.
Figure 12C:
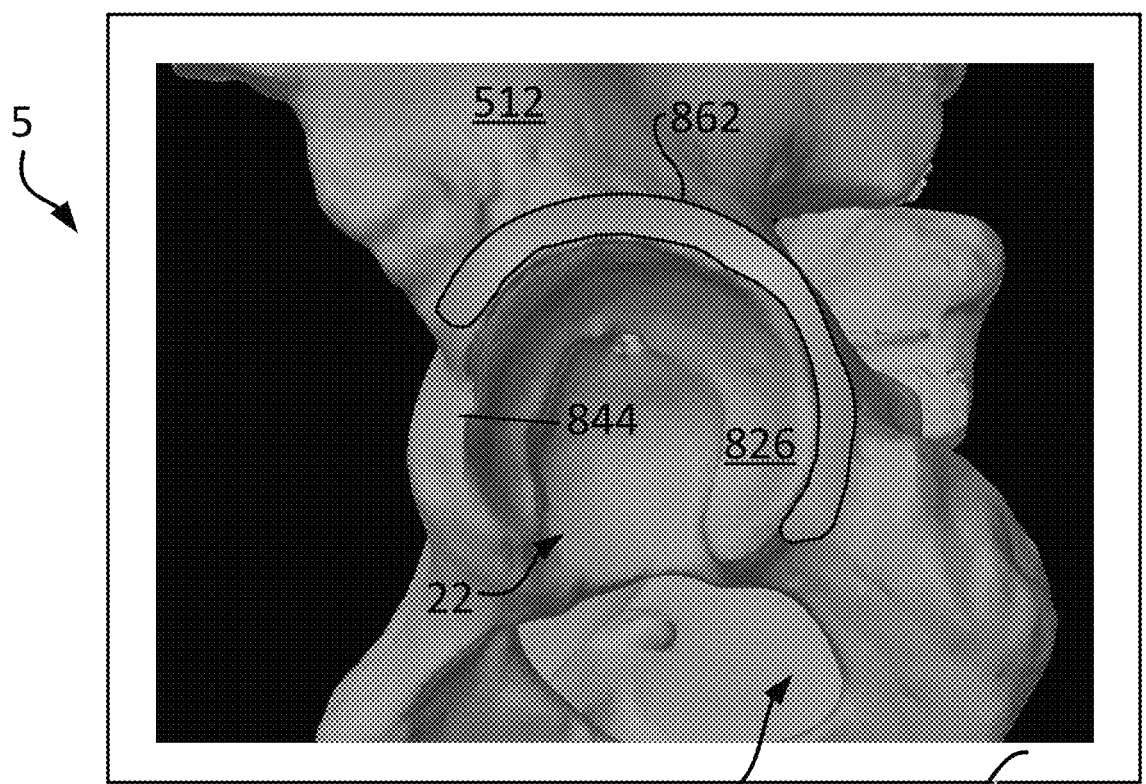
FIG. 12C is lateral view of the three dimensional bone model of the patient pelvis with a highlighted band on the posterior and superior aspect of the acetabular rim.
Figure 12D:
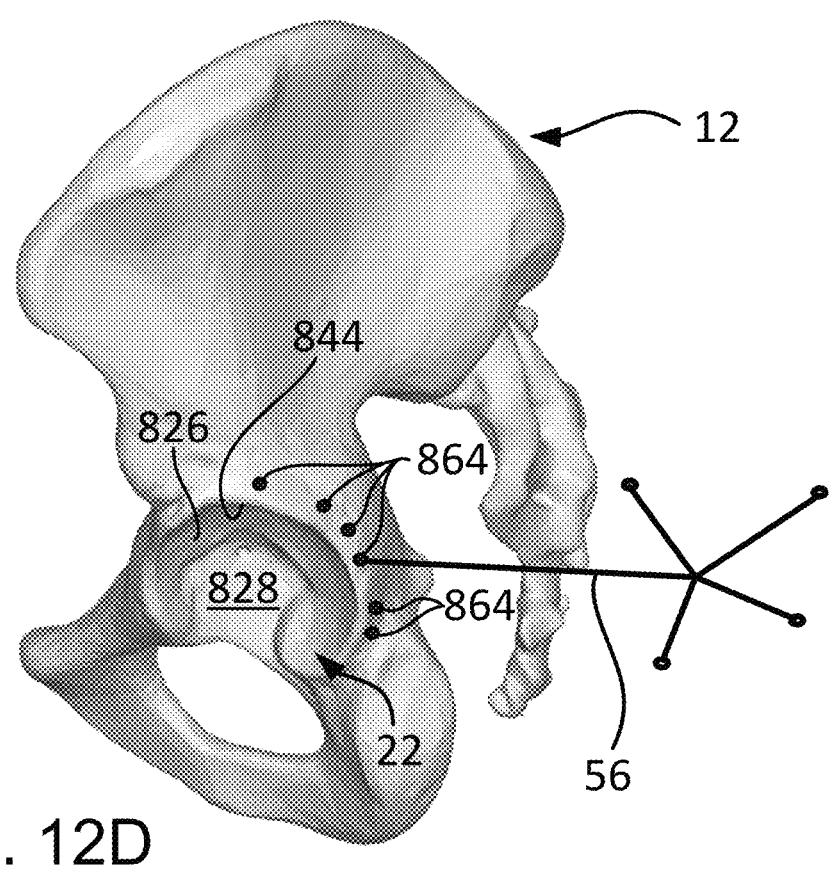
FIG. 12D is a lateral view of the patient pelvis intra-operatively with a distal tip of a navigational probe contacting a point on the posterior aspect of the acetabular rim.

Referring back to FIG. 8A, fine registration 816 includes a region-based point collection or capture of acetabular landmarks 818. Within this step, points are captured at the acetabular rim 820 and at the articular surface of the acetabulum 822. As seen in FIG. 8B, the region-based capture in the fine registration is approach dependent. FIGS. 12A-12B illustrate an antero-lateral and direct anterior approach to point capture on the acetabular rim 844, and FIGS. 12C-12D illustrate a postero-lateral approach to point capture on the acetabular rim 844. In certain embodiments, registration may be complete without the fine registration 816.

To begin, reference is made to FIGS. 12A and 12B, which are, respectively, a lateral view of the three dimensional bone model 512 of the patient pelvis 12 (image space) and a lateral view of the patient pelvis 12 (physical space). As seen in FIG. 12A, the system 5 may identify a band 858, which may be highlighted, on the anterior and superior aspect of the acetabular rim 844 that forms the outer edge of the acetabulum 22 on the three dimensional bone model 512 of the patient pelvis (image space). The band 858 may extend outward a certain amount from the acetabular rim 844. The band 858 may indicate an allowable location for a region-based point collection or capture for a direct anterior or antero-lateral surgical approach.

As seen in FIG. 12B, the system 5 may query the surgeon to capture points 860 on the patient pelvis 12 (physical space), using the navigational probe 56, that correspond with the location of the band 858 on the three dimensional bone model 512 of the pelvis 12 (image space). Accordingly, the surgeon may contact the distal tip of the navigational probe 56 against various points 860 on the anterior and superior aspect of the acetabular rim 844 and capture, log, collect, or store data associated with the location of each point 860 as patient data within the system 5 (e.g., computer).

For fine registration of the acetabular rim 844 via a postero-lateral approach, as seen in FIG. 12C, which is a lateral view of the three dimensional bone model 512 of the patient pelvis 12 (image space), the system may identify a band 862, which may be highlighted, on the posterior and superior aspect of the acetabular rim 844 that forms the outer edge of the acetabulum 22 on the three dimensional bone model 512 of the patient pelvis 12 (image space). The band 862 may indicate an allowable location for a region-based point collection or capture for a postero-lateral surgical approach.

As seen in FIG. 12D, the system 5 may query the surgeon to capture points 864 on the patient pelvis 12 (physical space), using the navigational probe 56, that correspond with the location of the band 862 on the three dimensional bone model 512 of the pelvis 12 (image space). Accordingly, the surgeon may contact the distal tip of the navigational probe 56 against various points 864 on the posterior and superior aspect of the acetabular rim 844 and capture, log, collect, or store data associated with the location of each point 864 as patient data within the system 5 (e.g., computer).

During the step 820 of collecting points along the acetabular rim 844, the system 5 may require the distance between any two captured points 860 (for anterior and antero-lateral approaches), 864 (for postero-lateral approaches) to be a minimum distance apart from each other. In certain embodiments, the system 5 may require a minimum spacing between two captured points 860, 864 to be at least 1 mm. In certain embodiments, the system 5 may require a minimum spacing between two captured points 860, 864 to be at least 2 mm. In certain embodiments, the system 5 may require a minimum spacing between two captured points 860, 864 to be at least 3 mm. In certain embodiments, the system 5 may require a minimum spacing between two captured points 860, 864 to be at least 4 mm. In certain embodiments, the system 5 may require a minimum spacing between two captured points 860, 864 to be at least 5 mm. In certain embodiments, the system 5 may require a minimum spacing between two captured points 860, 864 to be at least 6 mm. In certain embodiments, the system 5 may require a minimum spacing between two captured points 860, 864 to be at least 7 mm. In certain embodiments, the system 5 may require a different minimum spacing between two captured points 860, 864. In certain embodiments, the system 5 may have an algorithm that defines a required distance between any two points 860, 864 based on other inputs (e.g. acetabulum 22 or acetabular component 28). In certain embodiments, the system 5 may vary the distance between any two points 860, 864 during point capture. Such a requirement may facilitate the dispersion of captured points 860, 864 so that all points 860, 864 are not captured in one region of the acetabular rim 844, for example. In certain embodiments, the system 5 may not require a defined distance spacing between points 860, 864. In certain embodiments, the collected point 860, 864 that is not satisfied the minimum spacing requirement may be rejected as an outlier or still be used for the point-to-model surface matching in fine registration 816.

In certain embodiments, the system 5 may require the surgeon to capture a maximum and/or a minimum number of points 860, 864 for a given surgical approach before proceeding to a subsequent step of the registration process. For example, in certain embodiments the system 5 may require a minimum of twenty points be captured. In certain embodiments the system 5 may require a minimum of fifteen points be captured. In certain embodiments the system 5 may require a minimum of ten points be captured. In certain embodiments the system 5 may require a minimum of five points be captured. In certain embodiments the system 5 may require between ten and twenty points be captured.

In a certain embodiment, the system 5 may optimize the number of points 860, 864 by stopping point 860, 864 collection when points 860, 864 are more than the minimum number of points 860, 864 but less than the maximum number of points 860, 864. The system 5 may use an algorithm such as convergence metrics to determine the stopping criterion/criteria. In a certain embodiment, a convergence metric can be the difference between 1) the root-mean-square error of point-to-model surface matching calculated using N collected acetabular rim points 860, 864 plus the articular surface points 830 and landmark points 842, 846, 848, 850, and 2) the root-mean-square error of point-to-model surface matching calculated using a subset of collected acetabular rim points 860, 864 such as N−1 collected points 860, 864 plus the articular surface points 830 and landmark points 842, 846, 848, 850. If the difference between the two root-mean-square errors is smaller than a predefined threshold, the system 5 ends the point 860, 864 collection early before the points 860, 864 reach the maximum number of points 860, 864. In a certain embodiment, the convergence metrics can be calculated every time when a new point 860, 864 is collected.

Referring back the fine registration 816 of FIG. 8A, the acetabulum articular surface is captured 822 and stored as patient data. This step 822 is similar to the methods described in reference to FIGS. 9A and 9B and, thus, the following discussion will be made with reference to those figures. Also, the discussion in reference to FIGS. 9A and 9B is also applicable to the discussion of step 822. For example, while the minimum distance between the points 830 was discussed in reference to FIGS. 9A and 9B, the system 5 may use the same parameters in the fine registration of the acetabulum articular surface capture 822. For the fine registration at step 822, as seen in FIG. 9A, the system 5 may display on a display screen 9 a highlighted band 824 on the articular surface 826 of the acetabulum 22 on the three dimensional bone model 512 of the patient pelvis 12 (image space). As discussed previously, this is a region-based point capture where the surgeon may capture points 830 on the patient pelvis 12 (physical space) on any area of the pelvis 12 that corresponds with the highlighted band 824 (i.e., articular surface 826).

As with the methods described in reference to FIGS. 9A-9B, the system 5 may require a certain number of points 830 be captured before moving on to other steps in the registration 800. In certain embodiments, the system 5 may require a minimum of twenty points be captured. In certain embodiments the system 5 may require a minimum of fifteen points be captured. In certain embodiments the system 5 may require a minimum of ten points be captured. In certain embodiments the system 5 may require a minimum of five points be captured. In certain embodiments the system 5 may require between ten and twenty points be captured.

Once all the acetabular rim points 860, 864 are collected, an algorithm may be used to determine the registration transform for fine registration 816. In a certain embodiment, the system 5 may use Iterative Closest Point (ICP) (P. J. Besl, H. D. McKay, A method for registration of 3-D shapes, IEEE Transactions on Pattern Analysis and Machine Intelligence, 1992), a point-to-surface matching algorithm that best fits the intra-operatively captured points (physical space) with the three dimensional bone model 512 (image space). In certain embodiments, the intra-operatively captured points might be a collection of previously mentioned articular surface points 830, acetabular rim points 860, 864, and landmark points 842, 846, 848, 850. In certain embodiments, the intra-operatively captured points might be a collection of articular surface points 830, acetabular rim points 860, 864, and landmark points 842, 846, 848, 850 with certain points removed (e.g., statistical outliers). In certain embodiments, the intra-operatively captured points might be used for both initial registration 802 and fine registration 816. In certain embodiments, the ICP algorithm may use the initial registration 802 transform as the initial guess to improve fine registration 816.

Using the information from the fine registration 816, quality metrics may be employed to determine the accuracy of registration.

Within the fine registration 816, quality metrics may be employed for checking and verifying the accuracy of the rotational orientation around the acetabular normal, as similarly described with reference to FIG. 11C. As seen in FIG. 11C, an intra-operatively determined vector V1 is compared with a pre-operatively determined vector V2 to determine the difference in rotational orientation between the intra-operatively captured points and the pre-operatively determined points. The intra-operatively determined vector V1 may extend from the center point 840, which is coextensive with the center of rotation point 836, to the intra-operatively captured point 852', which corresponds to the ASIS 854 of the patient pelvis (physical space). The pre-operatively determined vector V2 may extend from the center of rotation point 836 to the point 852 on the ASIS 854 as determined from the pre-operative image scans (e.g., CT, MRI) of the pelvis 12.

The vectors V1, V2 may extend from an acetabular plane 856, defined in a lateral view, which is coextensive with the acetabular rim 844. From this plane 856, a normal line centered at the center of rotation 836 may be identified. The angular difference A1 between the vectors V1, V2 may be used to lock the rotational alignment or orientation of the intra-operatively captured points (physical space) with the three dimensional bone model 512 (image space).

Figure 13A:
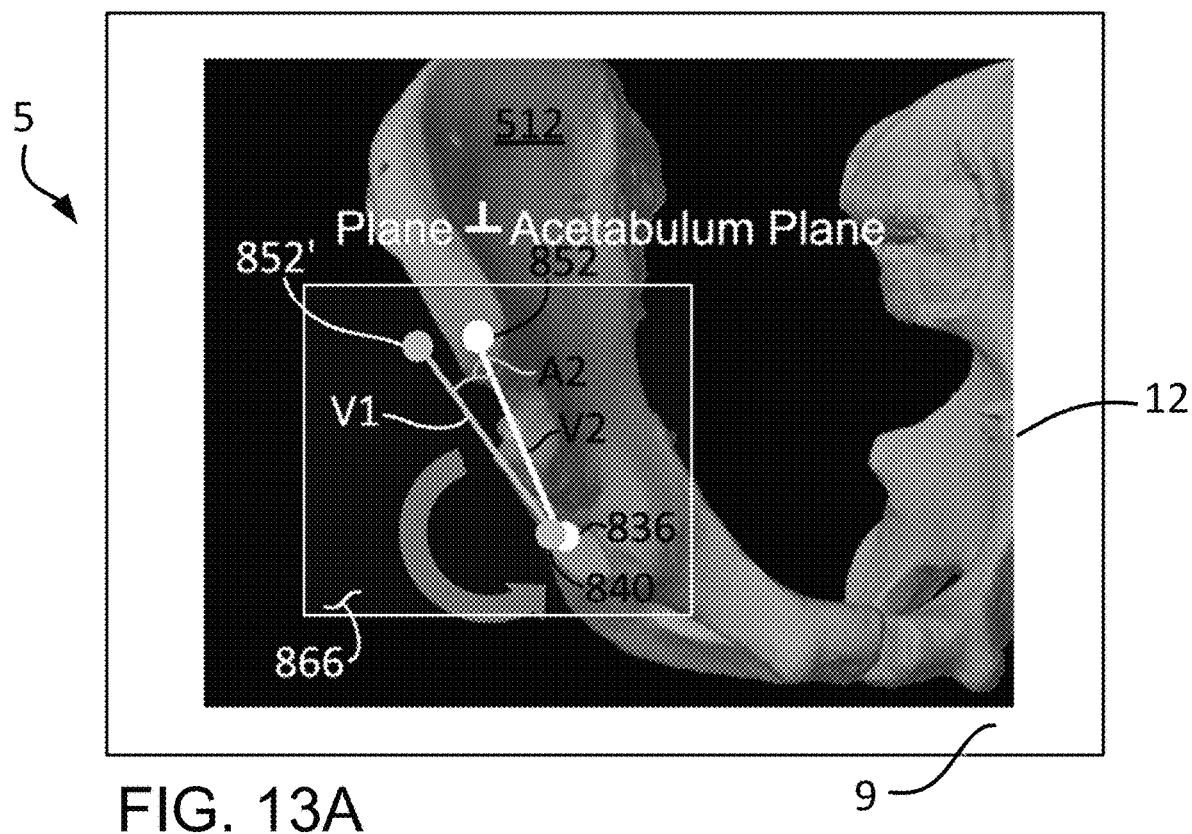
FIG. 13A is an anterior view of the three dimensional bone model depicting a pair of vectors in order to measure inclination about a plane that is perpendicular to the acetabular plane.

Another quality metric, as seen in FIG. 13A, which is an antero-lateral view of the three dimensional bone model 512 of the patient pelvis 12 (image space) displayed on a display screen 9 of the system 5, may be employed for checking inclination or rotation about a plane 866 perpendicular to the acetabular plane 856 as described in reference to FIG. 11C. As seen in FIG. 13A, vectors V1, V2 are the same vectors as shown and described in reference to FIG. 11C. FIG. 13A simply displays the vectors V1, V2 with respect to a plane 866 that is perpendicular to the acetabular plane 856 so as to measure an angular difference A2 between the vectors V1, V2 in the plane 866. The angle A2 may be used to measure an inclination or angular difference between the three dimensional bone model 512 of the pelvis 12 (image space) and the patient pelvis 12 (physical space).

Additionally or alternatively, the system 5 may include a quality metric by instructing the user to collect additional points on the patient's anatomy at different locations, and then the system 5 measures the distance between the captured point and the corresponding surface of the three dimensional bone model 512 to ensure registration accuracy is acceptable. In certain instances, the system 5 may queue the user to collect one verification point. In certain instances, the system 5 may queue the user to collect two verification points. In certain instances, the system 5 may queue the user to collect three verification points. In certain instances, the system 5 may queue the user to collect six verification points. In certain instances, the system 5 may queue the user to collect eight verification points. In certain instances, the system 5 may queue the user to collect up to ten verification points.

The location of the verification points may be locations corresponding to low confidence of registration (e.g., point-to-surface mapping is above a certain threshold). This way, areas of low confidence can identified and additional points can be captured in these areas to determine if registration can result in a higher confidence in the area. Once the user captures the verification points, the captured points may be added to the original point cloud, and all points may be used in the registration algorithm to refine the registration transform.

In certain instances, the location of the verification points may be approach dependent (e.g., direct anterior) so that the points are within the opening of the incision. In certain instances, the location of the verification points may be spaced apart from previously captured points so as to ensure a minimum distance between each of the captured points, or to ensure a balanced distribution of the captured points.

Upon completion of the fine registration 816, the system 5 may indicate that the registration process 800 is complete, and the surgical procedure may commence.

The following discussion focuses on a graphical user interface ("GUI") 1000 associated with guiding the capture of landmarks on the patient's anatomy during a registration procedure of a robotic surgery. Such guidance may be useful for the surgeon as he or she may be attempting to locate a physical point on the patient's pelvis 12 while also looking at a corresponding virtual point on the three dimensional bone model 512 displayed on a display screen 9. In this way, the GUI 1000 may provide guidance to the surgeon that he or she is nearing the physical point on the pelvis 12 that corresponds to the virtual point on the bone model 512.

Figure 13B:
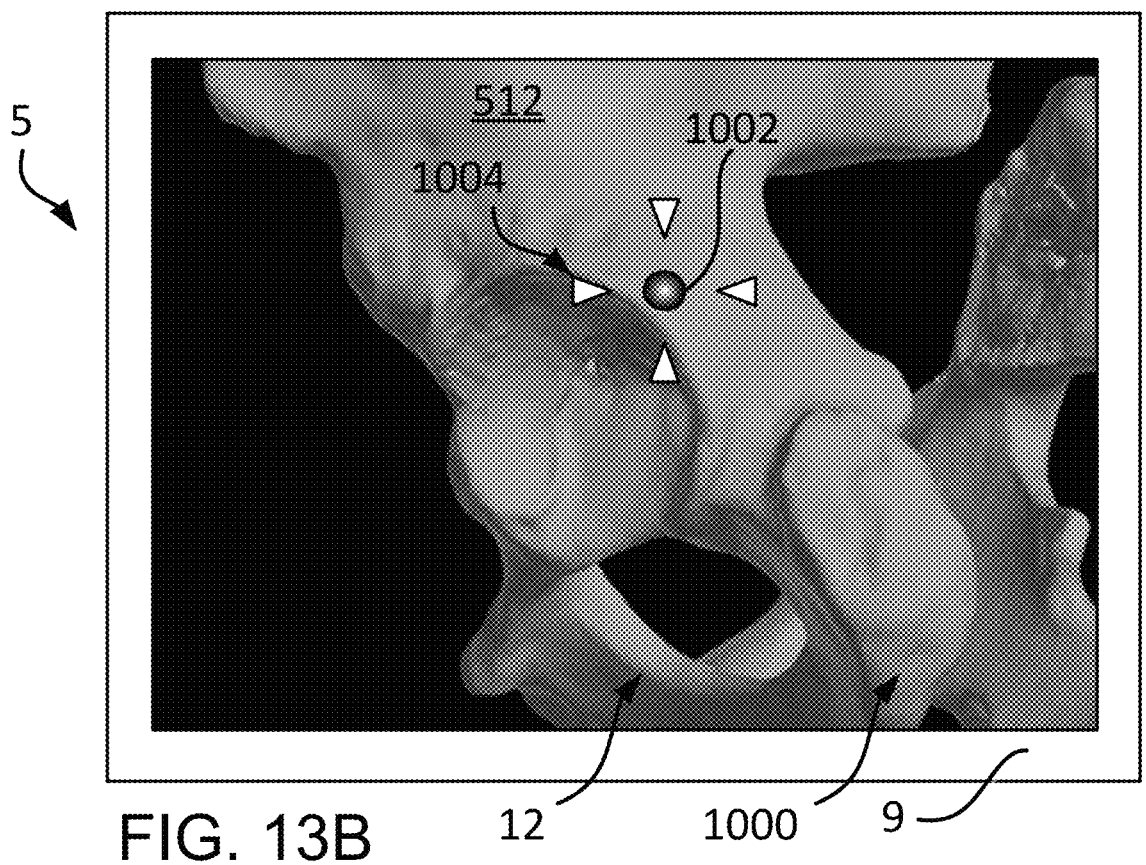
FIG. 13B is a postero-lateral view of the three dimensional bone model with a point highlighted on the posterior acetabular rim, and a first embodiment of graphic surrounding the point, where the graphic is spaced apart from the point by a first radius.
Figure 13C:
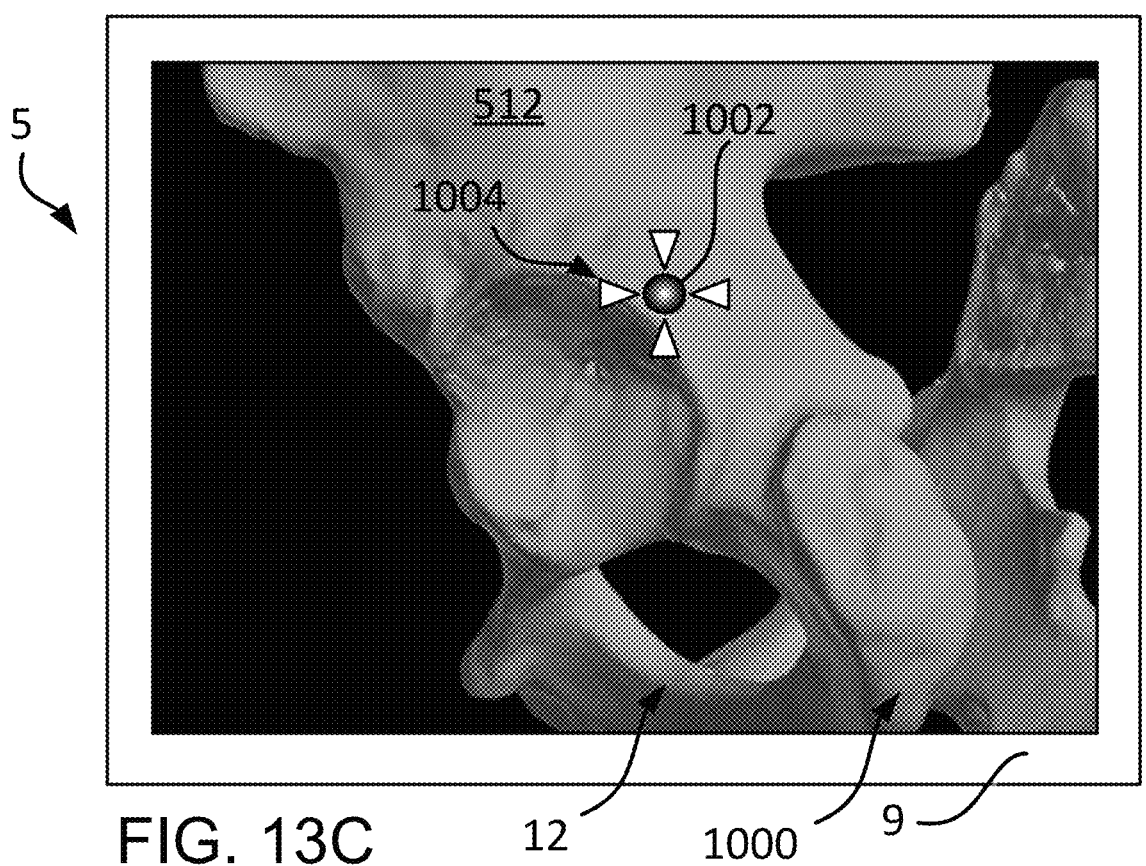
FIG. 13C is a postero-lateral view of the three dimensional bone model with a point highlighted on the posterior acetabular rim, and a first embodiment of graphic surrounding the point, where the graphic is spaced apart from the point by a second radius.
Figure 13D:
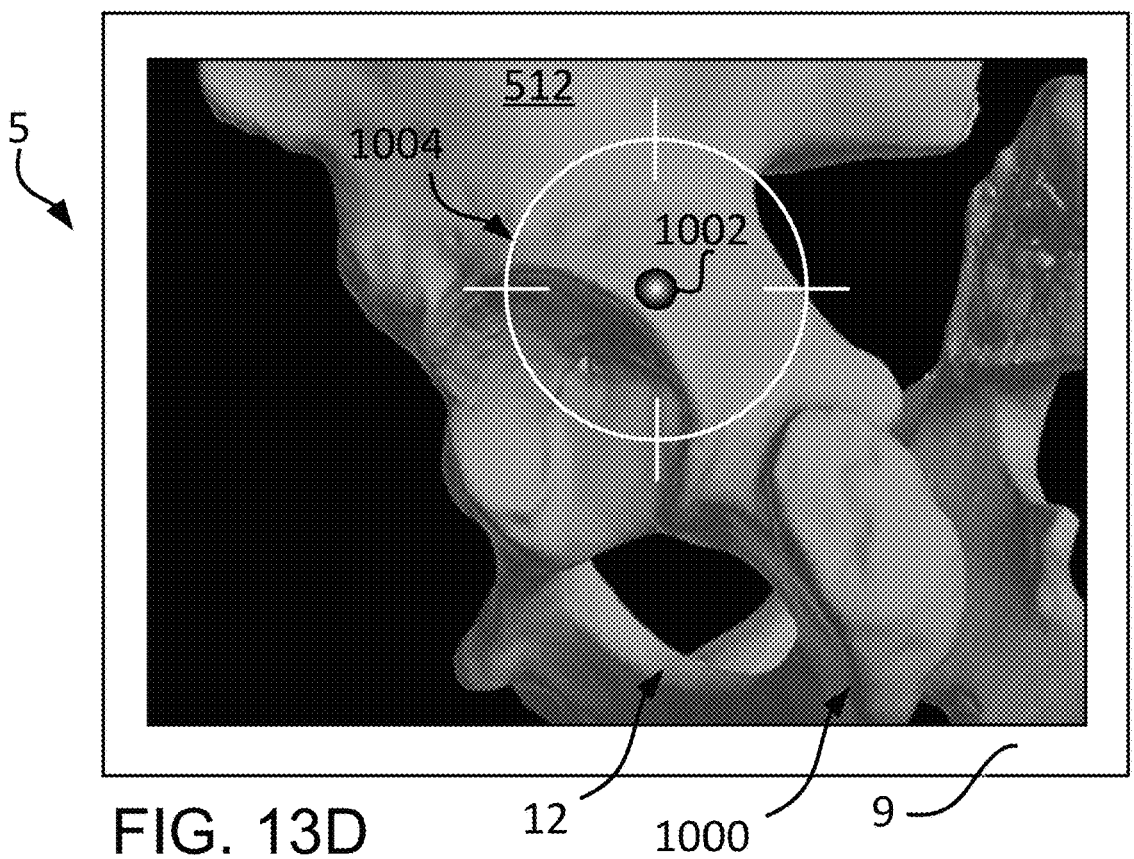
FIG. 13D is a postero-lateral view of the three dimensional bone model with a point highlighted on the posterior acetabular rim, and a second embodiment of graphic surrounding the point, where the graphic is spaced apart from the point by a first radius.
Figure 13E:
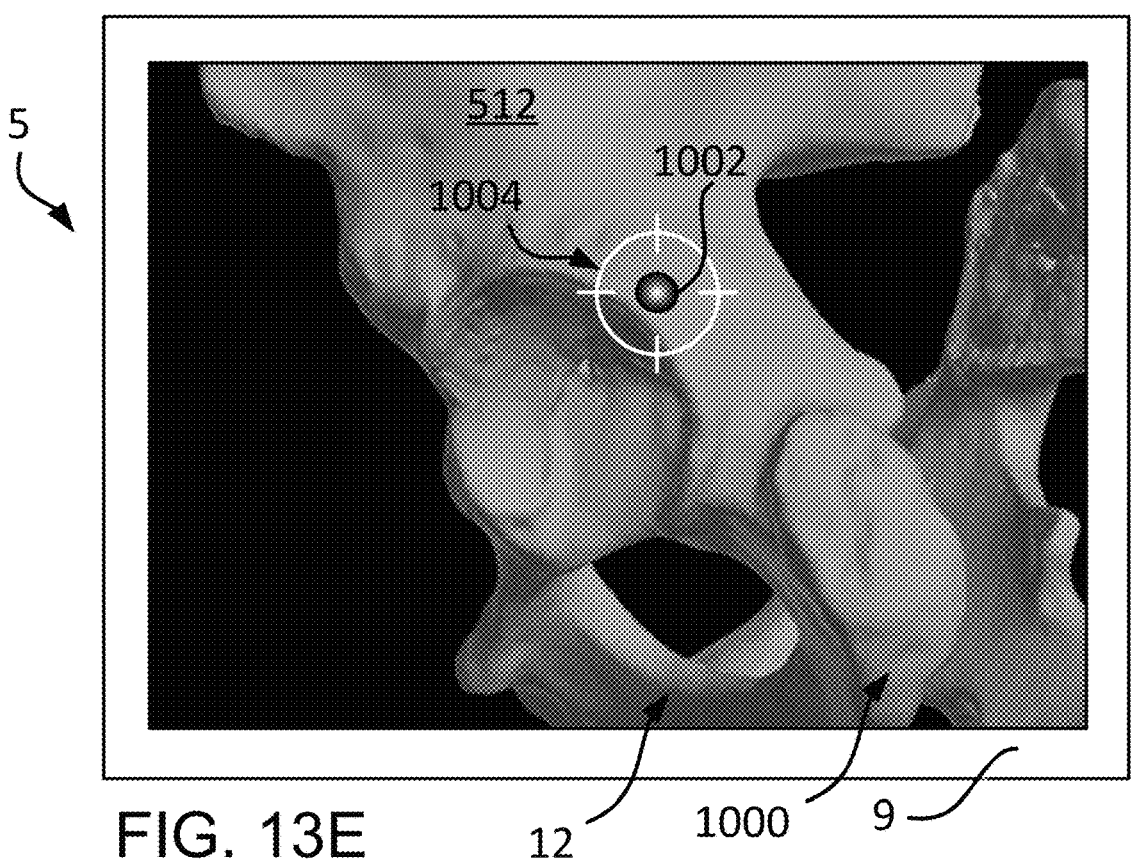
FIG. 13E is a postero-lateral view of the three dimensional bone model with a point highlighted on the posterior acetabular rim, and a second embodiment of graphic surrounding the point, where the graphic is spaced apart from the point by a second radius.

FIGS. 13B-13C depict a first embodiment of a GUI 1000 that guides a user in capturing a point 1002. FIGS. 13D-13E depict a second embodiment of a GUI 1000 that guides a user in capturing a point 1002.

Referring to FIG. 13B, the GUI 1000 is displayed on a display screen 9, which shows the three dimensional bone model 512 of the patient pelvis 12 on a portion of the screen 9. A virtual point 1002 is displayed on the bone model 512 for which the user is instructed to capture or collect with the system 5 on the patient's pelvis (physical space) with the navigation probe or other tracked tool (not shown). In certain instances, a radius of the virtual point 1002 (being relative to the patient's anatomy as replicated in the bone model 512) may be about 4 millimeters (mm). In certain instances, the radius of the virtual point 1002 may be other distances such as, for example, 2 mm, 6 mm, or 10 mm, among others.

In the first embodiment, directional arrows or triangles 1004 will appear and surround point 1002 in a generally circular fashion when the tip of the navigation probe or other tracked tool is within a certain radius or distance to the physical point on the patient's pelvis 12 that corresponds with the location of the virtual point 1002 on the bone model 512. In certain instances, the directional arrows 1004 will not be displayed until the tip of the navigation probe is within a 100 mm radius of the physical point that corresponds with the virtual point 1002. In this way, the arrows 1004 may appear and disappear, respectively, as the tip of the navigation probe moves within the 100 mm radius, and moves outside of the 100 mm radius. The radius of 100 mm is exemplary, and may be other distances such as, for example, 50 mm, 150 mm, or 200 mm, among others.

When the tip of the probe approaches and enters a certain radius or distance away from the point on the patient's pelvis 12 corresponding to the point 1002 on the bone model 512 (e.g., 100 mm), the arrows 1004 may appear and be spaced apart from the point 1002 a first radius. As the user moves the tip of the probe closer to the point on the patient's pelvis 12 corresponding to the point 1002 on the bone model 512, the arrows 1004 may move closer to the point 1002, as seen in FIG. 13C. Stated differently, as the user moves the tip of the probe closer to the point on the patient's pelvis 12 corresponding to the point 1002 on the bone model 512, the first radius decreases to a second radius. In certain instances, as the tip of the probe gets progressively closer to the physical point on the patient's pelvis 12 corresponding to the point 1002 on the bone model 512, the arrows 1004 corresponding move progressively closer to the point 1002, and the radius of the arrows 1004 progressively decreases indicating the tip of the probe is near the point 1002 to be captured. In certain instances, the point 1002 and/or the arrows 1004 may change color when the point is captured and/or when the tip of the probe is in a location accurately corresponding to the point 1002.

In this way, the GUI 1000 includes the directional arrows 1004 sequentially transitioning from a first state, as seen in FIG. 13B, where the arrows 1004 are further away from the point 1002, to a second state, as seen in FIG. 13C, where the arrows 1004 are closer to the point 1002. In certain instances, the color of the arrows and/or point 1002 may change when sequentially transitioning from the first state to the second state. For example, the colors may change from red, to yellow, and to green as the tip of the navigation probe progressively moves closer to the point 1002.

Referring to FIG. 13D, the graphical user interface ("GUI") 1000 is displayed on a display screen 9, which shows the three dimensional bone model 512 of the patient pelvis 12 on a portion of the screen 9. A virtual point 1002 is displayed on the bone model 512 for which the user is instructed to capture with the system 5 on the patient's pelvis (physical space) with the navigation probe or other tracked tool (not shown). In certain instances, a radius of the virtual point 1002 (being relative to the patient's anatomy as replicated in the bone model 512) may be about 4 mm. In certain instances, the radius of the virtual point 1002 may be other distances such as, for example, 2 mm, 6 mm, or 10 mm, among others.

In the second embodiment, a reticle 1004 having a circle with partial vertical and horizontal alignment indicators may appear and surround point 1002 when the tip of the navigation probe or other tracked tool is within a certain radius or distance to the physical point on the patient's pelvis 12 that corresponds with the location of the virtual point 1002 on the bone model 512. In certain instances, the reticle 1004 will not be displayed until the tip of the navigation probe is within a 100 mm radius of the physical point that corresponds with the virtual point 1002. In this way, the reticle 1004 may appear and disappear, respectively, as the tip of the navigation probe moves within the 100 mm radius, and moves outside of the 100 mm radius. The radius of 100 mm is exemplary, and may be other distances such as, for example, 50 mm, 150 mm, or 200 mm, among others.

When the tip of the probe approaches and enters a certain radius or distance away from the physical point on the patient's pelvis 12 corresponding to the virtual point 1002 on the bone model 512, the circle of the reticle 1004 may appear and be spaced apart from the point 1002 a first radius. As the user moves the tip of the probe closer to the point on the patient's pelvis 12 corresponding to the point 1002 on the bone model 512, the radius gets smaller such that the circle of the reticle 1004 moves closer to the point 1002, as seen in FIG. 13E. Stated differently, as the user moves the tip of the probe closer to the point on the patient's pelvis 12 corresponding to the point 1002 on the bone model 512, the first radius decreases to a second radius. In certain instances, as the tip of the probe gets progressively closer to the point on the patient's pelvis 12 corresponding to the point 1002 on the bone model 512, the size of the circle (e.g., the radius) of the reticle 1004 corresponding gets progressively smaller and closer to the point 1002 indicating that the tip of the probe is near the point 1002 to be captured. In certain instances, the point 1002 and/or the circle of the reticle 1004 may change color when the point is captured and/or when the tip of the probe is in a location accurately corresponding to the point 1002.

In this way, the GUI 1000 includes the a reticle 1004 sequentially transitioning from a first state, as seen in FIG. 13D, where a perimeter of the circle of the reticle 1004 is farther away from the point 1002, to a second state, as seen in FIG. 13E, where the perimeter of the circle of the reticle 1004 is closer to the point 1002. In certain instances, the color of the reticle 1004 and/or point 1002 may change when sequentially transitioning from the first state to the second state. For example, the colors may change from red, to yellow, and to green as the tip of the navigation probe progressively moves closer to the point 1002.

The directional arrows and reticle 1004 may be substituted for other graphics including, but not limited to a bulls eye, a pointer, a transparent circle or sphere, or destination pin, among others. Additionally, or alternatively, the graphic may blink, rotate, enlarge, or shrink to indicate a change in distance of the tip of the probe to the point 1002. In certain instances, any graphic may be used that generally identifies the point 1002 on the bone model 512 in a first way when the tip of the probe is a first distance from the point on the patient's pelvis 12 that corresponds with the point 1002, and generally identifies the point 1002 on the bone model 512 in a second way when the tip of the probe is a second distance from the patient's pelvis 12 that corresponds with the point 1002. In this example, the first distance may be further away from the point 1002 than the second distance, and the first way may be the graphic with a first diameter that is larger than a second diameter of the graphic in the second way.

It is noted that the GUI described in reference to FIGS. 13B-E may be utilized at any step in the methods described herein without limitation (e.g., initial registration, fine registration, verification).

While the former sections of this application focus on registration of the pelvis 12, the systems and methods described herein are applicable to intra-operative registration of other bones and joints. FIGS. 15A-15D depict example joints for intra-operative registration including a knee joint 600, a shoulder joint 700, an elbow joint 800, and an ankle joint 900, respectively.

Figure 15A:
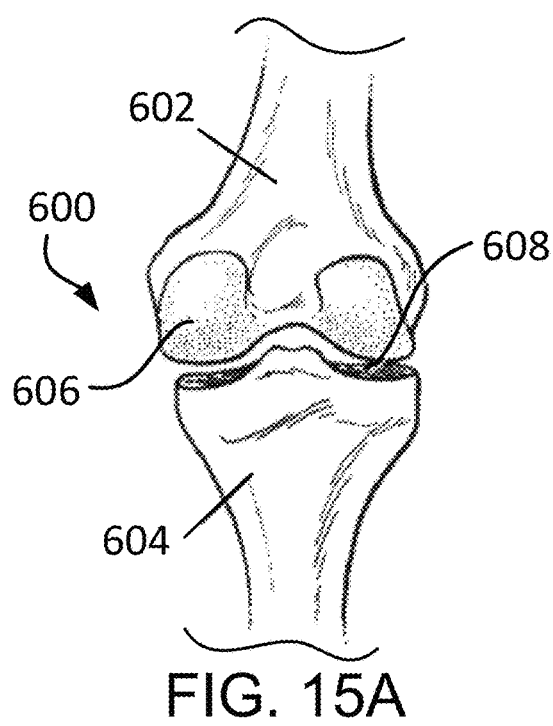
FIG. 15A is a posterior view of a knee joint.

As seen in FIG. 15A, the knee joint 600 includes a distal end of a femur 602 and a proximal end of a tibia 604. The distal end of the femur 602 includes medial and lateral condyles 606. The proximal end of the tibia 604 includes a tibial plateau 608 including medial and lateral portions configured to mate with the corresponding condyles 606 of the femur 602. As the knee joint 600 is articulated, the condyles 606 rotate relative to the tibial plateau 608. A thin layer of cartilage may be positioned between the condyles 606 and the tibial plateau 608. As seen in the figure, the condyles 606 may include a rounded or convex profile, whereas the tibial plateau 608 includes a concave profile. A total knee replacement may replace the distal end of the femur 602 including the condyles 606 with a femoral component of an implant, as well as a tibial component of an implant to replace the tibial plateau 608. During surgical registration of the tibia 604 and femur 602 for the knee arthroplasty, as with the systems and methods described with reference to the pelvis 12, a center of rotation could be calculated for the knee joint 600 based, for example, on a shape of the tibial plateau 608, or otherwise. Similarly, portions of the tibia 604 or femur 602 surrounding the tibial plateau 608 and condyles 606 may be registered, as well as a long point on one or both bones.

Figure 15B:
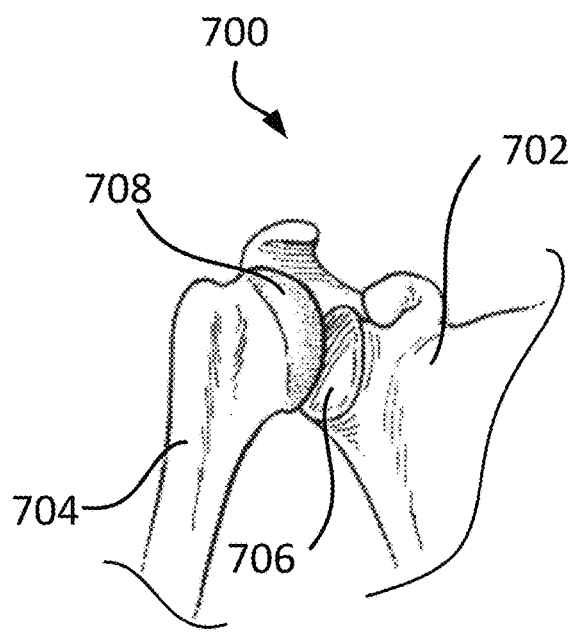
FIG. 15B is an anterolateral view of a shoulder joint.

As seen in FIG. 15B, the shoulder joint 700 includes a lateral portion of a scapula 702 and a proximal end of a humerus 704. The scapula 702 includes a glenoid cavity 706 which is a shallow pyriform articular surface on a lateral end of the scapula 702. A humeral head 708, which is nearly hemispherical in shape, articulates within the glenoid cavity 706. A conventional total shoulder replacement surgery may replace the humeral head 708 and glenoid cavity 706 with an implant having a stem that fits within the humerus 704 and an implant ball that fits within a glenoid socket component that is fitted to the scapula in place of the glenoid cavity 706. Generally, the humeral head 708 may be considered to include a convex bone portion, while the scapula 702 may be considered to include a concave bone portion. During surgical registration of the scapula 702 and humerus 704 in preparation for a shoulder arthroplasty, as with the systems and methods described with reference to the pelvis 12, a center of rotation could be calculated for the shoulder joint 700 based, for example, on a shape of the glenoid cavity 706, or otherwise. Similarly, portions of the scapula 702 surrounding the glenoid cavity 706 (e.g., a rim of the glenoid cavity 706) may be registered, as well as a long point (e.g., posterior spine of scapula 702, clavicle, acromion).

Figure 15C:
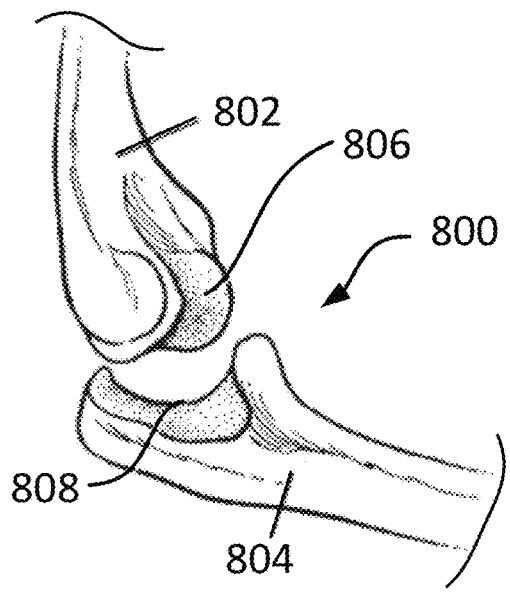
FIG. 15C is an anterolateral view of an elbow joint.

As seen in FIG. 15C, the elbow joint 800 includes a distal end of a humerus 802, and a proximal end of an ulna 804. The distal end of the humerus 802 includes a trochlea 806 that articulates with a trochlear notch 808 of the ulna 804. The trochlea 806 is convex from anterior to posterior, and concave medial to lateral. The trochlear notch 808 of the ulna 804 is concave anterior to posterior, and convex medial to lateral. The distal end of the humerus 802 also includes a capitulum that articulates with a head of a radius (not shown). Generally, the distal end of the humerus 802 may be considered to include a convex bone portion, while the ulna 804 may be considered to include a concave bone portion. A conventional elbow replacement includes replacing the distal end of the humerus 802 and the proximal end of the ulna 804 with an implant component having a humeral metal stem component, a fixed hinge, and an ulna metal stem component. During surgical registration of the humerus 802 and the ulna 804, as with the systems and methods described with reference to the pelvis 12, a center of rotation could be calculated for the elbow joint 800 based, for example, on a shape of the trochlear notch 808, or otherwise. Similarly, portions of the trochlear notch 808 (e.g., surrounding the notch 808, radial notch) may be registered, as well a long point on the ulna 804.

Figure 15D:
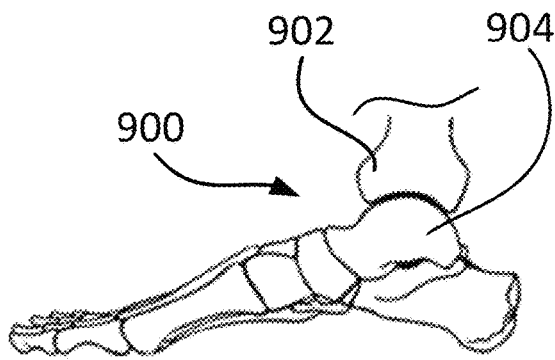
FIG. 15D is a medial view of an ankle joint.

As seen in FIG. 15D, the ankle joint 900 includes a distal end of the tibia 902 and a talus 904. The fibula is not shown. The distal end of the tibia 902 includes an inferior articular surface or plafond. A superior surface of the talus 904 includes an articular surface or trochlea tali, which is semi-cylindrical, and which mates with the distal end of the tibia 902. Generally, the distal end of the tibia 902 may be considered to include a concave bone portion, while the talus may be considered to include a convex bone portion. In a conventional ankle replacement surgery, the distal end of the tibia 902 and a proximal portion of the talus 904 are replaced with a tibial component and a talar component, respectively. The talar component is typically convex, and mates with the tibial component, which is concave. During surgical registration of an ankle replacement surgery, as with the system and methods described with reference to the pelvis 12, a center of rotation could be calculated for the ankle joint 900 based, for example, on a shape of the distal end of the tibia 902 or plafond, or otherwise. Similarly portions of the distal end of the tibia 902 or plafond (e.g., surrounding area) may be registered, as well as a long point on the tibia 902 (e.g., tibial tuberosity).

Figure 16A:
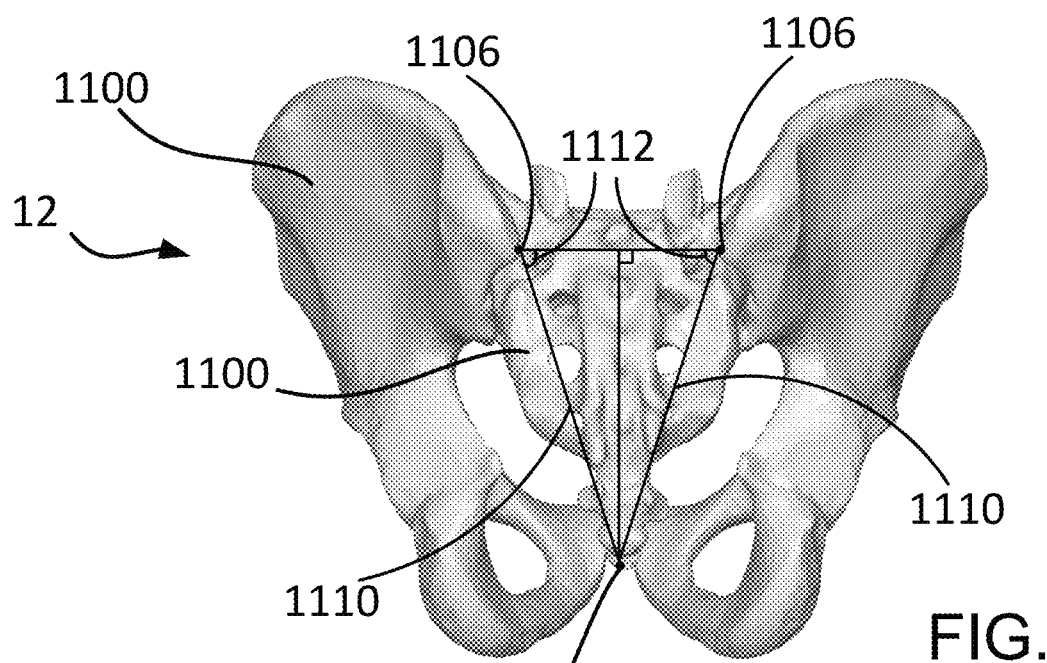
FIG. 16A is a posterior view of the pelvis showing the geometric relationship between the posterior superior iiiac spines and a distal sacrum.
Figure 16B:
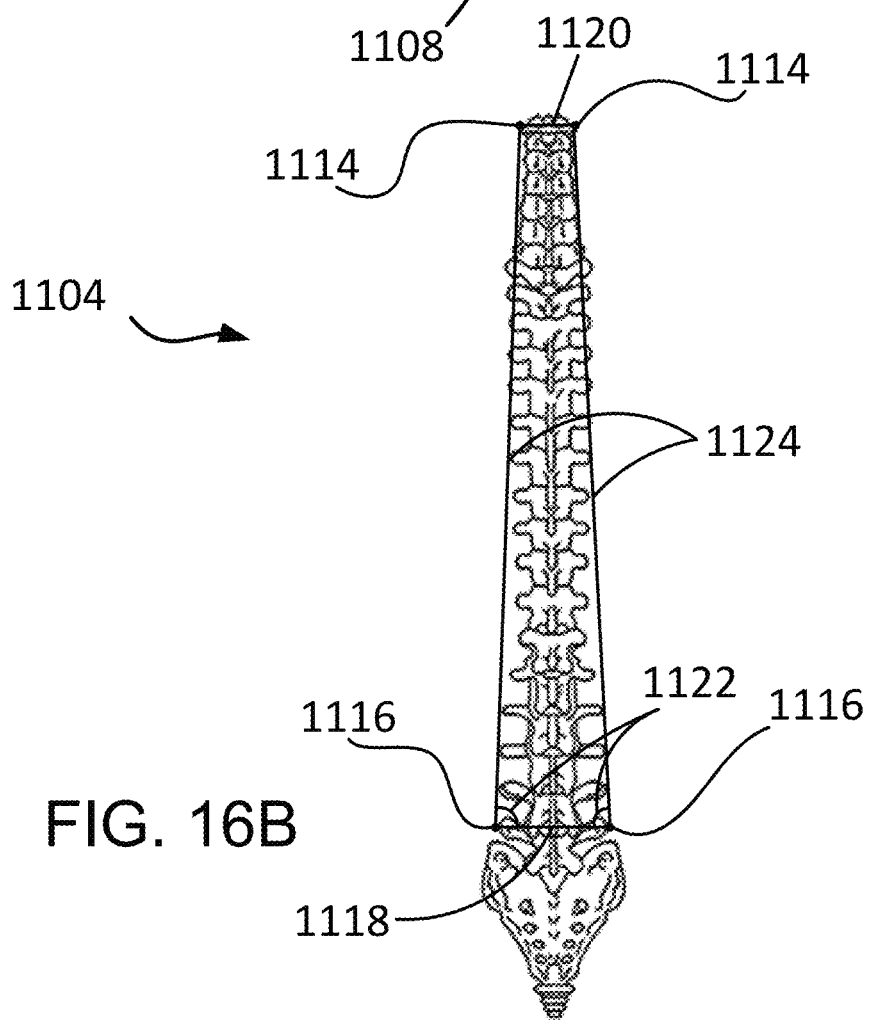
FIG. 16B is a posterior view of the spinal column showing the geometric relationship between the distal most joints and the proximal most joints.

FIGS. 16A and 16B depict additional or alternative registration methods for other portions of the body that utilizes pattern geometry to reduce the number of registrations points needed for an accurate registration process. FIG. 16A depicts a posterior view of a pelvis 12 including a left and right ilium 1100, and a sacrum 1102 between the left and right ilium 1100. FIG. 16B depicts a posterior view of a spinal column 1104.

As seen in FIG. 16A, there is a geometric relationship between the right and left posterior superior iliac spine ("PSIS") 1106 and the distal sacrum 1108. The distal sacrum 1108 may be any point at a medial-lateral midline of the sacrum 110 including, but not limited to, the apex of the sacrum at its connection with the base of the coccyx. The right and left PSIS 1106 and the distal sacrum 1108 define an isosceles triangle with two equal length sides 1110 and two equal angles 1112. Thus, the geometric information can be used in the registration process in a similar manner as the center of rotation calculation described previously. For example, a surgeon may capture the location of the right and left PSIS 1106 and the system 5 may guide the surgeon in capturing the location of the distal sacrum 1108 given that the lengths 1110 to the distal sacrum 1108 from each of the PSIS 1106 must be equal. Knowing the geometric relationship between the boney landmarks may provide guidance to the surgeon by ensuring the location for capturing of the distal sacrum 1108 is taken when the lengths 1110 are equal.

As seen in FIG. 16B, there is a geometric relationship between the most proximal joints 1114 of the spine 1104 and the most distal joints 1116 of the spine 1104. More particularly, the proximal joints 1114 and the distal joints 1116 may define an isosceles trapezoid with parallel bases 1118, 1120 and equal angles 1122 between the distal base 1118 and the legs 1124. Thus, the geometric information can be used in the registration process in a similar manner as the center of rotation calculation described previously to ensure that the surgeon captures accurate points.

C. Registering of Robotic Arm

Referring back to FIG. 5, after registering the pelvis at step S6, the robotic arm 30 may be registered at step S7. In this step, the robotic arm 30 is registered to correlate the pose of the robotic arm 30 (physical space) with the navigation system 7 (image space). The robotic arm 30 can be registered, for example, as described in U.S. patent application Ser. No. 11/357,197 (Pub. No. US 2006/0142657), filed Feb. 21, 2006, and hereby incorporated by reference herein in its entirety.

D. Preparation of the Acetabulum and Performance of the Surgical Procedure

In operation, the surgeon can use the robotic arm 30 of FIG. 3B to facilitate a joint replacement procedure, such as reaming bone and implanting an acetabular cup for a total hip replacement or hip resurfacing procedure. As explained above, the robotic arm 30 includes a surgical tool configured to be coupled to a cutting element (for reaming) and to engage a prosthetic component (for impacting). For example, as seen in FIG. 3B, for reaming, the end effector 40 can couple to the operating member 100, which couples to a cutting element. Similarly, for impacting, the end effector 40 can couple to another operating member, which engages the prosthetic component. The robotic arm 30 can be used to ensure proper positioning during reaming and impacting.

In step S8 of FIG. 5, the surgeon resurfaces the acetabulum 22 using a reamer, such as the operating member 100, coupled to the robotic arm 30 of FIG. 3B. As described above in connection with the operating member 100, the surgeon couples the appropriate operating member (e.g., a straight or offset reamer) to the end effector 40, connects the cutting element to the received operating member, and manually manipulates the robotic arm 30 to ream the acetabulum 22. During reaming, the robotic arm 30 provides haptic (force feedback) guidance to the surgeon. The haptic guidance constrains the surgeon's ability to manually move the surgical tool to ensure that the actual bone cuts correspond in shape and location to planned bone cuts (i.e., cuts consistent with the surgical plan).

In step S9 of FIG. 5, the surgeon verifies that the registration (i.e., the geometric relationship) between the acetabular tracking array and the pelvis 12 is still valid by contacting the pelvis checkpoint with a tracked probe as described, for example, in U.S. patent application Ser. No. 11/750,807 (Pub. No. US 2008/0004633), filed May 18, 2007, and hereby incorporated by reference herein in its entirety. If registration has degraded (e.g., because the acetabular tracking array was bumped during reaming), the pelvis 12 is re-registered. Registration verification can be performed any time the surgeon wants to check the integrity of the acetabular registration.

In step S10 of FIG. 5, the prosthetic component 316 is implanted on the reamed acetabulum 22 using an impactor tool. In a manner identical to that described above in connection with step S8 (reaming), during the impaction step S10, the display device 9 can show the planned pose 500, the activation region 510, the representations 512, 514 of the anatomy, and a representation of the surgical tool, as seen in FIG. 4. Also as described above in connection with step S8, if the surgeon moves the end effector 40 to override the haptic feedback, the controller can initiate automatic control of the surgical tool to substantially align at least one aspect of the actual pose with the corresponding desired aspect of the target pose.

In step S11 of FIG. 5, the surgeon installs the femoral component on the femur 14, and in step S12, the surgeon determines leg length and femoral offset. At any time during the surgical procedure, the display device 9 can show data related to progress and/or outcome. For example, after reaming in step S8 and/or impacting in step S10), data relating to the actual position of the reamed acetabulum 22 (or the implanted acetabular cup) can include, for example, numerical data representing error between the actual and planned locations in the three orthogonal planes of the patient's anatomy (i.e., medial/lateral, superior/inferior, and anterior/posterior).

V. Example Computing System

Figure 14:
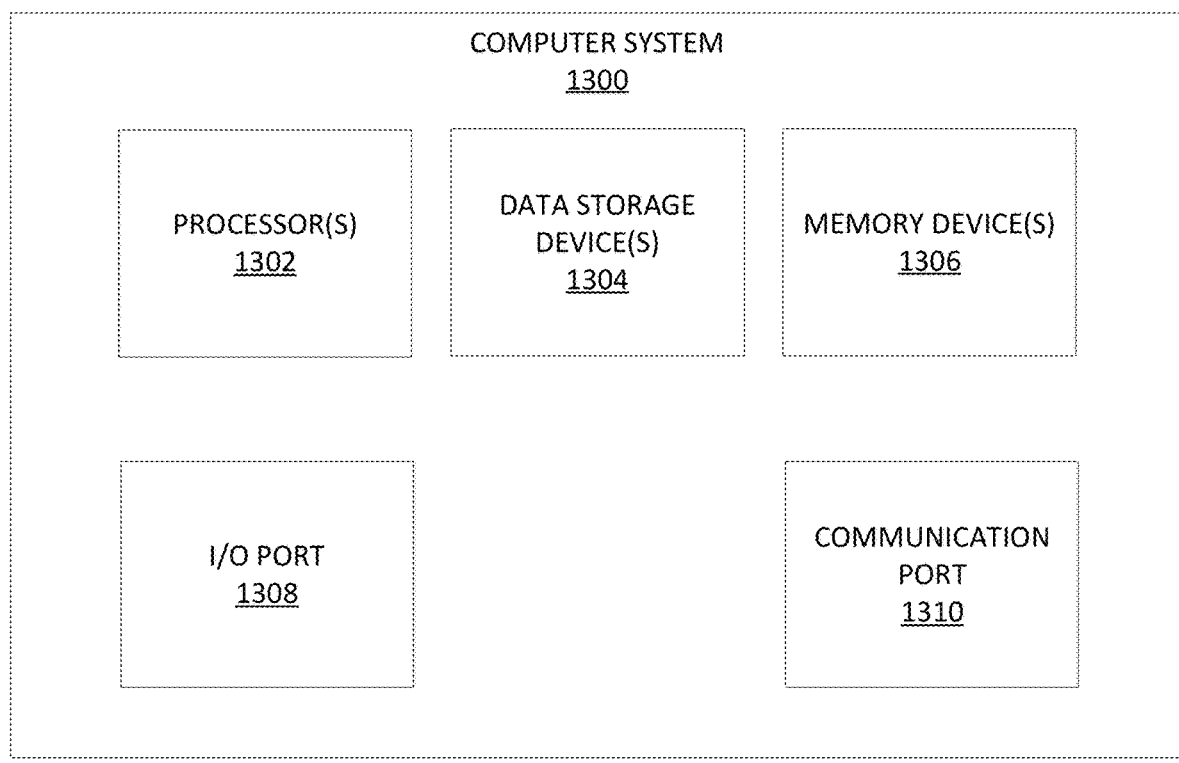
FIG. 14 is an example computing system having one or more computing units that may implement various systems and methods discussed herein is provided.

Referring to FIG. 14, a detailed description of an example computing system 1300 having one or more computing units that may implement various systems and methods discussed herein is provided. The computing system 1300 may be applicable to any of the computers or systems utilized in the preoperative or intra-operative planning of the arthroplasty procedure (e.g., registration), and other computing or network devices. It will be appreciated that specific implementations of these devices may be of differing possible specific computing architectures not all of which are specifically discussed herein but will be understood by those of ordinary skill in the art.

The computer system 1300 may be a computing system that is capable of executing a computer program product to execute a computer process. Data and program files may be input to the computer system 1300, which reads the files and executes the programs therein. Some of the elements of the computer system 1300 are shown in FIG. 14, including one or more hardware processors 1302, one or more data storage devices 1304, one or more memory devices 1308, and/or one or more ports 1308-1310. Additionally, other elements that will be recognized by those skilled in the art may be included in the computing system 1300 but are not explicitly depicted in FIG. 14 or discussed further herein. Various elements of the computer system 1300 may communicate with one another by way of one or more communication buses, point-to-point communication paths, or other communication means not explicitly depicted in FIG. 14.

The processor 1302 may include, for example, a central processing unit (CPU), a microprocessor, a microcontroller, a digital signal processor (DSP), and/or one or more internal levels of cache. There may be one or more processors 1302, such that the processor 1302 comprises a single central-processing unit, or a plurality of processing units capable of executing instructions and performing operations in parallel with each other, commonly referred to as a parallel processing environment.

The computer system 1300 may be a conventional computer, a distributed computer, or any other type of computer, such as one or more external computers made available via a cloud computing architecture. The presently described technology is optionally implemented in software stored on the data stored device(s) 1304, stored on the memory device(s) 1306, and/or communicated via one or more of the ports 1308-1310, thereby transforming the computer system 1300 in FIG. 14 to a special purpose machine for implementing the operations described herein. Examples of the computer system 1300 include personal computers, terminals, workstations, mobile phones, tablets, laptops, personal computers, multimedia consoles, gaming consoles, set top boxes, and the like.

The one or more data storage devices 1304 may include any non-volatile data storage device capable of storing data generated or employed within the computing system 1300, such as computer executable instructions for performing a computer process, which may include instructions of both application programs and an operating system (OS) that manages the various components of the computing system 1300. The data storage devices 1304 may include, without limitation, magnetic disk drives, optical disk drives, solid state drives (SSDs), flash drives, and the like. The data storage devices 1304 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 1306 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 1304 and/or the memory devices 1306, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 1300 includes one or more ports, such as an input/output (I/O) port 1308 and a communication port 1310, for communicating with other computing, network, navigation, or robotic devices. It will be appreciated that the ports 1308-1310 may be combined or separate and that more or fewer ports may be included in the computer system 1300.

The I/O port 1308 may be connected to an I/O device, or other device, by which information is input to or output from the computing system 1300. Such I/O devices may include, without limitation, one or more input devices, or output devices, such as, for example, robotic arms, and navigation and tracking systems.

In one implementation, the input devices convert a human-generated signal, such as, human voice, physical movement, physical touch or pressure, and/or the like, into electrical signals as input data into the computing system 1300 via the I/O port 1308. Similarly, the output devices may convert electrical signals received from computing system 1300 via the I/O port 1308 into signals that may be sensed as output by a human, such as sound, light, and/or touch. The input device may be an alphanumeric input device, including alphanumeric and other keys for communicating information and/or command selections to the processor 1302 via the I/O port 1308. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"), and/or tracking/probe devices associated with the navigation and tracking systems. The output devices may include, without limitation, a display, a touchscreen, a speaker, a tactile and/or haptic output device, and/or the like. In some implementations, the input device and the output device may be the same device, for example, in the case of a touchscreen.

In one implementation, a communication port 1310 is connected to a network by way of which the computer system 1300 may receive network data useful in executing the methods and systems set out herein as well as transmitting information and network configuration changes determined thereby. Stated differently, the communication port 1310 connects the computer system 1300 to one or more communication interface devices configured to transmit and/or receive information between the computing system 1300 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 1310 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 1310 may communicate with an antenna or other link for electromagnetic signal transmission and/or reception.

In an example implementation, patient data, bone models (e.g., generic, patient specific), transformation software, tracking and navigation software, registration software, and other software and other modules and services may be embodied by instructions stored on the data storage devices 1304 and/or the memory devices 1306 and executed by the processor 1302. The computer system 1300 may be integrated with or otherwise form part of the surgical system 100. The system may be configured for registering patient data gathered intra-operatively from a first bone with a computer model of the first bone in a common coordinate system. The first bone may joint a second bone to form a joint such as, for example, a hip joint, a knee joint, a shoulder joint, an elbow joint, or ankle joint, among others. The system may include a surgical navigation system including a tracking device and a tool (e.g., navigation probe, end of a surgical robotic arm) to be tracked in its movement by the tracking device. Additionally, the system may include a computing device (one or more) in communication with the navigation system. The computing device may perform the following steps: 1) receive first data points of the patient data from first intra-operatively collected points on an articular surface of the concave portion of the bone. The first data points may be collected using the at least one tool. The first data points may correspond in location to a first articular region on the computer model. 2) receive a second data point from a second intra-operatively collected point on the first bone. The second data point may be collected using the at least one tool. The second data point may correspond in location to a second virtual data point on the computer model. 3) determine an intra-operative center of rotation from the first data points. The intra-operative center of rotation may correspond to a physical center of rotation of the second bone relative to the first bone. 4) compare a first distance between the virtual center of rotation and the second virtual data point and a second distance between the intra-operative center of rotation and the second data point. And, 5) run a transformation with the patient data and the computer model so as to have them correspond with respect to position and orientation.

The system set forth in FIG. 14 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed herein, for example, those shown in FIGS. 5 and 8A-8B, among others, may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure including any of the methods described herein may be provided as a computer program product, software, or computerized method that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow. For example, while the description discusses methods involving the hip, the disclosure is similarly applicable to other joints including the shoulder, ankle, and spine, among others.

In general, while the embodiments described herein have been described with reference to particular embodiments, modifications can be made thereto without departing from the spirit and scope of the disclosure. Note also that the term "including" as used herein is intended to be inclusive, i.e. "including but not limited to."

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The invention claimed is:

1. A system for registering patient data gathered intra-operatively of a first bone with a computer model of the first bone in a coordinate system, the first bone comprising a concave portion and forming a joint with a second bone comprising a convex portion, the system comprising:
   a) a surgical navigation system comprising a tracking device and at least one tool configured to be tracked in its movement by the tracking device;
   b) at least one computing device in communication the surgical navigation system, the computer model of the first bone accessible to the at least one computing device, the at least one computing device:
      i) computing an intra-operative center of rotation from first data points of patient data captured on an articular surface of the concave portion of the first bone, the first data points corresponding in location to a first articular region on the computer model;
      ii) identifying a registration zone for capturing one or more second data points of patient data on the first bone based on a selected surgical approach of a direct anterior approach, an antero-lateral approach, or a postero-lateral approach, the registration zone being located at a surgically accessible region on the first bone for the selected surgical approach, the registration zone for the selected surgical approach defining a permissible area for capturing of the one or more second data points, the registration zone for the selected surgical approach corresponding in location to a virtual registration zone on the computer model;
      iii) receiving the one or more second data points of patient data captured within the registration zone on the first bone based on the selected surgical approach; and
      iv) running a transformation with the patient data and the computer model so as to have them correspond with respect to position and orientation.

2. The system of claim 1, wherein first bone comprises an ilium, the concave portion comprises an acetabulum, and the second bone comprises a femur, and wherein the registration zone is located on a rim of the acetabulum.

3. The system of claim 2, wherein, for the direct anterior approach and the antero-lateral approach, the registration zone is located on an anterior and superior portion of the rim of the acetabulum.

4. The system of claim 3, further comprising: aligning the intra-operative center of rotation with a virtual center of rotation of the computer model in the coordinate system; and comparing a first distance between the virtual center of rotation and a second virtual data point on the computer model corresponding to the one or more second data points and a second distance between the intra-operative center of rotation and at least one of the one or more second data points.

5. The system of claim 4, further comprising: receiving a third data point of the patient data captured on the first bone, the third data point being in a different location on the first bone than the one or more second data points and corresponding in location to a third virtual data point on the computer model; and comparing a third distance between the virtual center of rotation and the third virtual data point and a fourth distance between the intra-operative center of rotation and the third data point.

6. The system of claim 5, wherein the third data point is located on an anterior-superior iliac spine.

7. The system of claim 2, wherein, for the postero-lateral approach, the registration zone is located on a posterior and superior portion of the rim of the acetabulum.

8. The system of claim 7, further comprising: aligning the intra-operative center of rotation with a virtual center of rotation of the computer model in the coordinate system; and comparing a first distance between the virtual center of rotation and a second virtual data point on the computer model corresponding to the one or more second data points and a second distance between the intra-operative center of rotation and at least one of the one or more second data points.

9. The system of claim 8, further comprising: receiving a third data point of the patient data captured on the first bone, the third data point being in a different location on the first bone than the one or more second data points and corresponding in location to a third virtual data point on the computer model; and comparing a third distance between the virtual center of rotation and the third virtual data point and a fourth distance between the intra-operative center of rotation and the third data point.

10. The system of claim 9, wherein the third data point is located on an anterio-superior iliac spine.

11. The system of claim 2, wherein surgically inaccessible regions are excluded from the registration zone.

12. The system of claim 2, wherein the at least one computing device is in communication with a display screen, and the registration zone is displayed on the display screen relative to an image of the first bone.

13. The system of claim 2, wherein the at least one tool comprises at least one of a free-hand navigation probe and an arm of a surgical robot.

14. The system of claim 1, wherein the joint comprises one of a hip joint, a shoulder joint, a knee joint, an elbow joint, and an ankle joint.

15. The system of claim 2, wherein the registration zone is also located on the articular surface of the acetabulum.

16. The system of claim 1, wherein the one or more second data points comprises a plurality of points, and wherein the registration zone is sized to permit the plurality of points to be spaced apart from each other.

17. The system of claim 16, wherein the plurality of points are required to be spaced apart from each other by a minimum distance within the registration zone.

* * * * *